US 8,586,542 B2

(12) United States Patent
Hanson et al.

(10) Patent No.: US 8,586,542 B2
(45) Date of Patent: *Nov. 19, 2013

(54) SMALL MOLECULE APOPTOSIS PROMOTERS

(75) Inventors: Gunnar J. Hanson, Dallas, TX (US); David Thomas, Dallas, TX (US); Nizal Chandrakumar, North Grafton, MA (US); Susan Harran, Dallas, TX (US)

(73) Assignee: Joyant Pharmaceuticals, Inc., Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/536,974

(22) Filed: Jun. 28, 2012

(65) Prior Publication Data

US 2013/0281385 A1   Oct. 24, 2013

Related U.S. Application Data

(63) Continuation of application No. 12/897,760, filed on Oct. 4, 2010, now Pat. No. 8,222,291, which is a continuation of application No. 11/726,602, filed on Mar. 21, 2007, now Pat. No. 7,807,699.

(60) Provisional application No. 60/784,612, filed on Mar. 12, 2006, provisional application No. 60/854,975, filed on Oct. 27, 2006.

(51) Int. Cl.
*A61K 38/00* (2006.01)

(52) U.S. Cl.
USPC .......................................... 514/18.9; 314/19.2

(58) Field of Classification Search
None
See application file for complete search history.

(56) References Cited

U.S. PATENT DOCUMENTS

| | | | |
|---|---|---|---|
| 7,807,699 B2 * | 10/2010 | Hanson et al. | 514/359 |
| 8,222,291 B2 * | 7/2012 | Hanson et al. | 514/422 |
| 2008/0051389 A1 * | 2/2008 | Hanson et al. | 514/220 |

* cited by examiner

*Primary Examiner* — Cecilia J Tsang
*Assistant Examiner* — Fred Reynolds
(74) *Attorney, Agent, or Firm* — Richard Aron Osman

(57) ABSTRACT

The invention provides small molecule mimics of the Smac peptide that are dimer- or dimer-like compounds having two amide-containing domains connected by a linker. These compounds are useful to promote apoptosis. The invention includes pharmaceutical compositions comprising such compounds and methods to use them to treat conditions including cancer and autoimmune disorders.

20 Claims, No Drawings

SMALL MOLECULE APOPTOSIS PROMOTERS

CROSS-REFERENCE TO RELATED APPLICATIONS

This application is a continuation of U.S. application Ser. No. 12/897,760, filed 4 Oct. 2010 (U.S. Pat. No. 8,222,291), which is a continuation of U.S. application Ser. No. 11/726,602, filed 21 Mar. 2007 (U.S. Pat. No. 7,807,699), which claims priority to U.S. Provisional Application Ser. No. 60/784,612, filed 12 Mar. 2006; and to U.S. Provisional Application Ser. No. 60/854,975, filed 27 Oct. 2006. The content of each of these documents is incorporated by reference herein in its entirety.

TECHNICAL FIELD

The field of the invention is dimer-like small molecule promoters of apoptosis. The compounds of the invention have a linking group that connects two binding domains, each of which contains two essential amide groups and at least one ring. These compounds mimic the activity of the protein known as Smac, and are thereby able to promote the initiation of apoptosis. The compounds are therefore useful in treating conditions where initiating apoptosis is desirable, such as in pathological cells or tissues.

BACKGROUND ART

Apoptosis plays a central role in the development and homeostasis of all multi-cellular organisms. Abnormal inhibition of apoptosis is a hallmark of cancer and autoimmune diseases, whereas excessive activation of cell death is implicated in neuro-degenerative disorders such as Alzheimer's disease. Pro-apoptotic chemotherapeutic drugs provide a recent approach to overcoming the clinical problem of drug resistance; see, e.g. Makin et al., *Cell Tissue Res.* 2000 July; 301(1): 143-52 ("Apoptosis and cancer chemotherapy").

The mechanism of apoptosis is conserved across species and executed with a cascade of sequential activation of proteases called caspases. Once activated, these caspases are responsible for proteolytic cleavage of a broad spectrum of cellular targets that ultimately lead to cell death. IAPs (inhibitor-of-apoptosis proteins) regulate apoptosis by inhibiting caspases; and a protein called Smac ('Smac' stands for second mitochondria-derived activator of caspases, and is a mitochondrial protein) binds to and inhibits IAPs, and thereby promotes caspase activation.

The protein Smac has been shown to inhibit a wide variety of IAPs, and is believed to be a key regulator of apoptosis in mammals. See Du, et al., *Cell* 102:33-43 (2000); Verhagen et al., *Cell* 102:43-53 (2000); and Vucic et al., *Biochem. J.* 385(1):11-20 (2005). N-terminal Smac-derived peptides and mimetics have been shown to similarly inhibit IAPB, and promote caspase activation. IAPB are components of TNFR (tumor necrosis factor receptor), so IAP inhibitors can divert TNFR signalling from an NfkB-mediated pro-inflammatory signal, to an anti-inflammatory apoptotic signal.

Defective apoptosis regulation can confer resistance to many current treatment protocols, leading to tumor growth. This may occur as a result of overexpression of IAPB, which inhibit the caspases that would otherwise initiate apoptosis. Alternatively, deregulation can occur as a result of underproduction of the Smac peptides that act to inhibit IAP activity. Deficiency of Smac can thus allow IAP to prevent apoptosis from occurring when it should, and a Smac mimetic like the present compounds can replace the activity of Smac and thus promote desired apoptosis.

Debatin, et al., WO 03/086470, describes Smac-peptides as therapeutic agents useful against cancer and autoimmune diseases; they are reported to act by sensitizing the cells toward TRAIL-induced or anticancer drug-induced apoptosis. (TRAIL stands for TNF related apoptosis-inducing ligand). See also Li, et al., *Science,* 305 (3 Sep. 2004), 1471-4. Debatin provides in vivo evidence that Smac induces the eradication of certain tumors such as glioblastoma tumor models in animals when administered in combination with TRAIL. According to Debatin, aggressive cancer phenotypes, which result from deregulation of signaling pathways, commonly fail to undergo apoptosis when they otherwise would, allowing rapid and abnormal tissue growth. Bockbrader, et al., disclose efficacy of Smac mimic compounds on breast cancer cell lines when used in conjunction with TRAIL or etoposide, or when used in cells that express TRAIL at relatively high levels. *Oncogene* vol. 24, 7381-88 (2005).

Similarly, according to Debatin, defects in apoptosis regulation play a key role in the pathogenesis of autoimmune disorders, including lupus erythematodes disseminatus and rheumatoid arthritis. Accordingly, compounds that mimic the activity of Smac can treat some of the effects of such conditions.

A recent U.S. Patent Application, US 2005/0197403, describes dimeric compounds with good activity as promoters of apoptosis. The compounds have two amide-containing groups linked by a linker that is broadly described. Another U.S. Patent Application, US 2006/0025347, describes small molecule compounds having activity related to promotion of apoptosis. However, while the latter reference mentions that dimeric compounds can be used, none of the compounds it discloses have a dimeric structure, nor is there any indication of what type of dimers to explore.

DISCLOSURE OF THE INVENTION

The present invention relates to novel compounds having apoptosis promoting effects that, without being bound by theory, appear to originate in their ability to mimic Smac. These compounds are believed to bind to two separate domains in the baculovirus inhibitory repeat (BIR) domain within the proteins referred to as IAP (inhibitor-of-apoptosis) proteins, which regulate apoptosis by inhibiting caspases. The compounds are dimers or dimer-like, in that they possess two structurally similar binding domains, each of which includes a ring that is substituted by at least one aryl-containing group —W—X. These two domains are linked by a linking group, and while similar, the domains need not be identical. In certain embodiments, the two binding domains are the same, so the molecule is symmetric about its linking group.

The invention also provides "monomeric" structures, as further described below, and methods of using these to make dimeric compounds of, e.g., formula (1), (8), (11) and (15). These monomers (e.g., compounds of formula (4), (7), (10) or (14)) are useful for making the apoptosis-promoters described herein.

The invention provides a compound of formula (I):

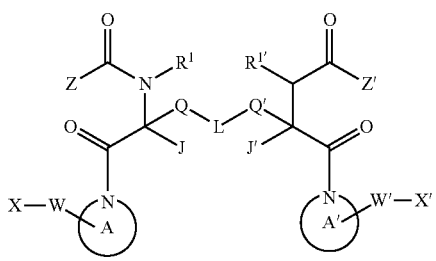

(I)

or a pharmaceutically acceptable salt or hydrate form thereof; and including any stereoisomeric forms thereof;

wherein each of ring A and ring A' independently represents an azacyclic ring core which is selected from a saturated 3-8 membered monocyclic azacyclic ring and a saturated 8-12 membered fused polycyclic azacyclic ring, each of which may contain 0-2 additional heteroatoms selected from N, O, S as ring members; and wherein ring A is substituted with a group represented as —W—X, and ring A' is substituted with a group represented as —W'—X', and each of ring A and ring A' may be optionally substituted with from 1-4 additional substituents suitable for its structure;

each J and J' is independently H, CN, C1-C4 alkyl or C1-C4 alkyloxycarbonyl;

each W and W' independently represents C=O, C=S, or an optionally substituted $C_2$-$C_6$ alkylene or $C_2$-$C_6$ heteroalkylene; or W can be a bond where X comprises an optionally substituted C5-C6 aryl or heteroaryl ring, and/or W' can be a bond where X' comprises an optionally substituted C5-C6 aryl or heteroaryl ring;

each X and X' independently represents an optionally substituted C5-C20 ring system comprising at least one aromatic ring and up to four heteroatoms selected from N, O and S as a ring member, and can represent either a single 5-15 membered cyclic group or two 5-10 membered cyclic groups that are both attached to the same atom of W or W', provided that each X and X' comprises at least one aryl or heteroaryl ring;

each Q and Q' independently represents —$CH_2$—, —CH(OR)—, —CH(R)—, —($CH_2$)$_r$D-, —CH(R)D-, or —CR=CR— or —C≡C—, wherein r is 1-4, each D is independently O, NR, or S, and wherein each R is independently H, or optionally substituted $C_1$-$C_8$ alkyl or optionally substituted $C_1$-$C_8$ heteroalkyl; or one or both of Q and Q' can be a bond where L comprises a ring;

each $R^1$ and $R^{1'}$ is independently H or optionally substituted C1-C4 alkyl;

each Z and Z' is independently an optionally substituted C1-C6 aminoalkyl; and

L represents a linker that is a C2-C20 hydrocarbyl group, optionally containing from 1-6 heteroatoms selected from N, O and S, which linker is 2 to 10 atoms in length when counted along the shortest path between Q and Q', and which may be optionally substituted;

with the proviso that L does not comprise a disulfide bond.

In another aspect, the invention provides a monomer of formula (II), and methods of using them for the preparation of compounds of formula (I):

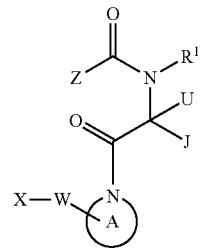

(II)

or a pharmaceutically acceptable salt or hydrate form thereof; and including any stereoisomeric forms thereof;

wherein ring A represents an azacyclic ring core which is selected from a saturated 3-8 membered monocyclic azacyclic ring and a saturated 8-12 membered fused polycyclic azacyclic ring, each of which may contain 0-2 additional heteroatoms selected from N, O, S as ring members; and wherein ring A is substituted with a group represented as —W—X, and ring A may be optionally substituted with from 1-4 additional substituents suitable for its structure;

J is H, CN, C1-C4 alkyl or C1-C4 alkyloxycarbonyl;

W represents C=O, C=S, or an optionally substituted $C_2$-$C_6$ alkylene or $C_2$-$C_6$ heteroalkylene; or W can be a bond where X comprises an optionally substituted 5-membered or 6-membered aryl or heteroaryl ring;

X represents an optionally substituted C5-C20 ring system comprising at least one aromatic ring and up to four heteroatoms selected from N, O and S, and can represent either a single 5-15 membered cyclic group or two 5-10 membered cyclic groups that are both attached to the same atom of W, provided that each X comprises at least one aryl or heteroaryl ring;

U represents C1-C8 alkyl, C1-C8 heteroalkyl, C2-C8 alkenyl, C2-C8 heteroalkenyl, C2-C8 alkynyl, C2-C8 heteroalkynyl, C5-C12 aryl, C5-C12 heteroaryl, C5-C20 arylalkyl or C5-C20 heteroarylalkyl, each of which may be optionally substituted;

$R^1$ is H or optionally substituted C1-C4 alkyl; and

Z is an optionally substituted C1-C6 aminoalkyl wherein the amine may be in a protected or unprotected form.

The invention further provides a compound of formula (1):

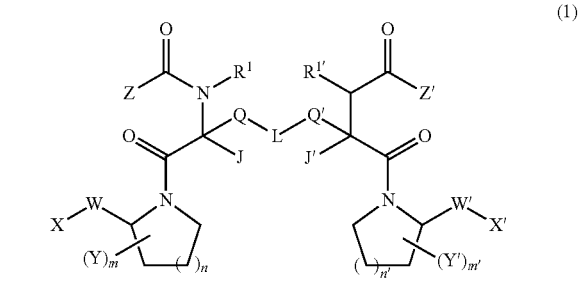

(1)

or a pharmaceutically acceptable salt or hydrate form thereof; and including any stereoisomeric forms thereof;

wherein each J and J' is independently H, CN, C1-C4 alkyl or C1-C4 alkyloxycarbonyl;

each Y and Y' independently represents optionally substituted C1-C8 alkyl, C5-C12 aryl, C5-C20 arylalkyl, or a heteroform of one of these; or is =O, OR, SR, S(O)R, $SO_2$R, $SO_2NR_2$, $NR_2$, OC(O)R, NRC(O)R, NRCOOR, NRC(O)$NR_2$, $NRSO_2$R, CN, C(O)$NR_2$, C(O)R, COOR, $NO_2$ or halo, wherein each R is independently H, $C_1$-$C_8$ alkyl, C5-C12 aryl or C5-C20 arylalkyl, or a heteroform of one of these; or is any other substituent suitable for an alkyl group;

and wherein two Y or Y' groups on the same ring can cyclize to form a 3-6 membered ring that can be saturated, unsaturated or aromatic, and which ring may include a heteroatom selected from O, S and N as a ring member and may be substituted;

each W and W' independently represents C=O, C=S, or an optionally substituted $C_2$-$C_6$ alkylene or $C_2$-$C_6$ heteroalkylene; or W can be a bond where X comprises an optionally substituted C5-C6 aryl or heteroaryl ring, and/or W' can be a bond where X' comprises an optionally substituted C5-C6 aryl or heteroaryl ring;

each X and X' independently represents an optionally substituted C5-C20 ring system comprising at least one aromatic ring and up to four heteroatoms selected from N, O and S as a ring member, and can represent either a single 5-15 membered cyclic group or two 5-10 membered cyclic groups that are both attached to the same atom of W or W', provided that each X and X' comprises at least one aryl or heteroaryl ring;

each Q and Q' independently represents —$CH_2$—, —CH(OR)—, —CH(R)—, —$(CH_2)_r$D-, —CH(R)D-, or —CR=CR— or —C≡C—, wherein r is 1-4, each D is independently O, NR, or S, and wherein each R is independently H, optionally substituted $C_1$-$C_8$ alkyl or optionally substituted $C_1$-$C_8$ heteroalkyl; or one or both of Q and Q' can be a bond where L comprises a ring;

each n and n' is independently 0-3;

each m and m' is independently 0-4;

each $R^1$ and $R^{1'}$ is independently H or optionally substituted C1-C4 alkyl;

each Z and Z' is independently an optionally substituted C1-C6 aminoalkyl; and

L represents a linker that is a C2-C20 hydrocarbyl group, optionally containing from 1-6 heteroatoms selected from N, O and S, which linker is 2 to 10 atoms in length when counted along the shortest path between Q and Q', and which may be optionally substituted;

with the proviso that L does not comprise a disulfide bond.

In another aspect, the invention provides a compound of formula (2):

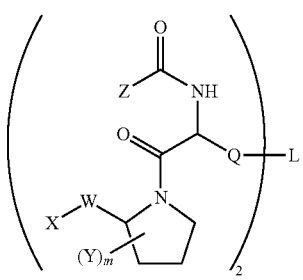

(2)

or a pharmaceutically acceptable salt or hydrate form thereof; and including any stereoisomeric forms thereof;

W represents C=O, C=S, or an optionally substituted $C_2$-$C_6$ alkylene or optionally substituted $C_2$-$C_6$ heteroalkylene; or W can be a bond where X comprises an optionally substituted 5-membered or 6-membered aryl or heteroaryl ring;

X represents an optionally substituted C5-C20 ring system comprising at least one aromatic ring and up to four heteroatoms selected from N, O and S, and can represent either a single 5-15 membered cyclic group or two 5-10 membered cyclic groups that are both attached to the same atom of W, provided that X comprises at least one aryl or heteroaryl ring;

Q represents —$CH_2$—, —CH(OR)—, —CH(R)—, —$CH_2$O—, —CH(R)O—, or —$(CH_2)_4$NH—, wherein R is H, or $C_1$-$C_4$ alkyl or $C_1$-$C_4$ heteroalkyl; or Q can be a bond where L comprises a ring;

m is 0-4;

Z represents an optionally substituted C1-C6 aminoalkyl group; and

L represents a C2-C8 alkylene, C5-C12 arylene, or C5-C20 arylalkylene linker, or a heteroform of one of these, each of which may be optionally substituted and may be saturated or unsaturated;

with the proviso that L does not comprise a disulfide bond.

In yet another aspect, the invention provides a compound of formula (3):

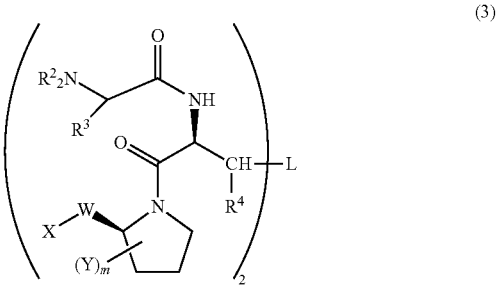

(3)

or a pharmaceutically acceptable salt or hydrate form thereof;

wherein each $R^2$ is independently H, or an optionally substituted $C_1$-$C_8$ alkyl or optionally substituted $C_1$-$C_8$ heteroalkyl group, and the two $R^2$ groups on one nitrogen can cyclize to form an optionally substituted azacyclic group having 3-8 ring members, which azacyclic group may be saturated, unsaturated or aromatic, and may contain 1-2 additional heteroatoms selected from N, O and S as ring members;

each $R^3$ is H, or an optionally substituted $C_1$-$C_8$ alkyl or optionally substituted $C_1$-$C_8$ heteroalkyl group, and $R^3$ can cyclize with $R^2$ on an adjacent nitrogen atom to form an optionally substituted azacyclic group having 3-8 ring members, which azacyclic group may be saturated, unsaturated or aromatic, and may contain 1-2 additional heteroatoms selected from N, O and S as ring members;

each $R^4$ is H, OH, or an optionally substituted $C_1$-$C_8$ alkyl or optionally substituted $C_1$-$C_8$ heteroalkyl group;

each W represents a group of the form —C(O)NR(CHR)$_p$—, where p is 0-2, and each R is independently H, $C_1$-$C_4$ alkyl or $C_1$-$C_4$ heteroalkyl; or W can be a bond where X comprises an optionally substituted 5-membered or 6-membered aryl or heteroaryl ring;

m is 0-4; and

X, Y, and L are as defined for formula (2);

with the proviso that L does not comprise a disulfide bond.

In another aspect, the invention provides a monomer of formula (4), and methods of using them for the preparation of compounds of formula (1)-(3), (8), (11) or (15):

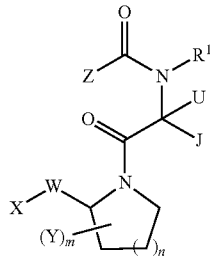

or a pharmaceutically acceptable salt or hydrate form thereof; and including any stereoisomeric forms thereof;

wherein J is H, CN, C1-C4 alkyl or C1-C4 alkyloxycarbonyl;

each Y represents optionally substituted C1-C8 alkyl, C5-C12 aryl, C5-C20 arylalkyl, or a heteroform of one of these; or is =O, OR, SR, S(O)R, $SO_2R$, $SO_2NR_2$, $NR_2$, OC(O)R, NRC(O)R, NRCOOR, NRC(O)$NR_2$, $NRSO_2R$, CN, C(O)$NR_2$, C(O)R, COOR, $NO_2$ or halo, wherein each R is independently H, $C_1$-$C_8$ alkyl, C5-C12 aryl or C5-C20 arylalkyl, or a heteroform of one of these; or is any other substituent suitable for an alkyl group;

and wherein two Y groups can cyclize to form a 3-6 membered ring that can be saturated, unsaturated or aromatic, and which ring may include a heteroatom selected from O, S and N as a ring member and may be substituted;

W represents C=O, C=S, or an optionally substituted $C_2$-$C_6$ alkylene or $C_2$-$C_6$ heteroalkylene; or W can be a bond where X comprises an optionally substituted 5-membered or 6-membered aryl or heteroaryl ring;

X represents an optionally substituted C5-C20 ring system comprising at least one aromatic ring and up to four heteroatoms selected from N, O and S, and can represent either a single 5-15 membered cyclic group or two 5-10 membered cyclic groups that are both attached to the same atom of W, provided that each X comprises at least one aryl or heteroaryl ring;

U represents C1-C8 alkyl, C1-C8 heteroalkyl, C2-C8 alkenyl, C2-C8 heteroalkenyl, C2-C8 alkynyl, C2-C8 heteroalkynyl, C5-C12 aryl, C5-C12 heteroaryl, C5-C20 arylalkyl or C5-C20 heteroarylalkyl, each of which may be optionally substituted; with the proviso that U is not isopropyl;

n is 0-3;

m is 0-4;

$R^1$ is H or optionally substituted C1-C4 alkyl; and

Z is an optionally substituted C1-C6 aminoalkyl wherein the amine may be in a protected or unprotected form.

In another aspect, the invention provides a compound of formula (5):

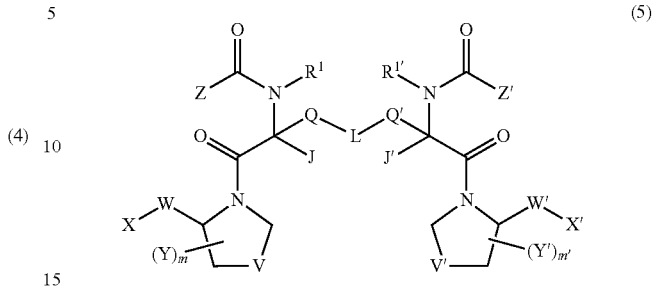

or a pharmaceutically acceptable salt or hydrate form thereof; and including any stereoisomeric forms thereof;

wherein each J and J' is independently H, CN, C1-C4 alkyl or C1-C4 alkyloxycarbonyl;

each V and V' is independently O or S;

each Y and Y' independently represents optionally substituted C1-C8 alkyl, C5-C12 aryl, C5-C20 arylalkyl, or a heteroform of one of these; or is =O, OR, SR, S(O)R, $SO_2R$, $SO_2NR_2$, $NR_2$, OC(O)R, NRC(O)R, NRCOOR, NRC(O)$NR_2$, $NRSO_2R$, CN, C(O)$NR_2$, C(O)R, COOR, $NO_2$ or halo, wherein each R is independently H, $C_1$-$C_8$ alkyl, C5-C12 aryl or C5-C20 arylalkyl, or a heteroform of one of these; or is any other substituent suitable for an alkyl group;

and wherein two Y or Y' groups on the same ring can cyclize to form a 3-6 membered ring that can be saturated, unsaturated or aromatic, and which ring may include a heteroatom selected from O, S and N as a ring member and may be substituted;

each W and W' independently represents C=O, C=S, or an optionally substituted $C_2$-$C_6$ alkylene or $C_2$-$C_6$ heteroalkylene; or W can be a bond where X comprises an optionally substituted C5-C6 aryl or heteroaryl ring, and/or W' can be a bond where X' comprises an optionally substituted C5-C6 aryl or heteroaryl ring;

each X and X' independently represents an optionally substituted C5-C20 ring system comprising at least one aromatic ring and up to four heteroatoms selected from N, O and S as a ring member, and can represent either a single 5-15 membered cyclic group or two 5-10 membered cyclic groups that are both attached to the same atom of W or W', provided that each X and X' comprises at least one aryl or heteroaryl ring;

each Q and Q' independently represents —$CH_2$—, —CH(OR)—, —CH(R)—, —($CH_2$)$_r$D-, —CH(R)D-, or —CR=CR— or wherein r is 1-4, each D is independently O, NR, or 5, and wherein each R is independently H, optionally substituted $C_1$-$C_8$ alkyl or optionally substituted $C_1$-$C_8$ heteroalkyl; or one or both of Q and Q' can be a bond where L comprises a ring;

each m and m' is independently 0-4;

each $R^1$ and $R^{1'}$ is independently H or optionally substituted C1-C4 alkyl;

each Z and Z' is independently an optionally substituted C1-C6 aminoalkyl; and

L represents a linker that is a C2-C20 hydrocarbyl group, optionally containing from 1-6 heteroatoms selected from N, O and S, which linker is 2 to 10 atoms in length when counted along the shortest path between Q and Q', and which may be optionally substituted;

with the proviso that L does not comprise a disulfide bond.

In another aspect, the invention provides a compound of formula (6):

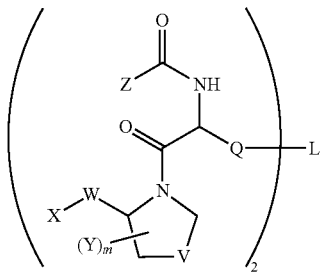

(6)

or a pharmaceutically acceptable salt or hydrate form thereof; and including any stereoisomeric forms thereof;

wherein V is O or S;

Y is optionally substituted C1-C8 alkyl, C5-C12 aryl, C5-C20 arylalkyl, or a heteroform of one of these; or is =O, OR, $NR_2$, $OC(O)R$, $NRC(O)R$, wherein each R is independently H or $C_1$-$C_8$ alkyl, C5-C12 aryl or C5-C20 arylalkyl, or a heteroform of one of these;

W represents C=O, C=S, or an optionally substituted $C_2$-$C_6$ alkylene or optionally substituted $C_2$-$C_6$ heteroalkylene; or W can be a bond where X comprises an optionally substituted 5-membered or 6-membered aryl or heteroaryl ring;

X represents an optionally substituted C5-C20 ring system comprising at least one aromatic ring and up to four heteroatoms selected from N, O and S, and can represent either a single 5-15 membered cyclic group or two 5-10 membered cyclic groups that are both attached to the same atom of W, provided that X comprises at least one aryl or heteroaryl ring;

Q represents —$CH_2$—, —CH(OR)—, —CH(R)—, —$CH_2$O—, —CH(R)O—, or —$(CH_2)_4$NH—, wherein R is H, or $C_1$-$C_4$ alkyl or $C_1$-$C_4$ heteroalkyl; or Q can be a bond where L comprises a ring;

m is 0-4;

Z represents an optionally substituted C1-C6 aminoalkyl group; and

L represents a C2-C8 alkylene, C5-C12 arylene, or C5-C20 arylalkylene linker, or a heteroform of one of these, each of which may be optionally substituted and may be saturated or unsaturated;

with the proviso that L does not comprise a disulfide bond.

In another aspect, the invention provides a monomer of formula (7), and methods of using them for the preparation of compounds of formula (5)-(6), (8), (12) or (16):

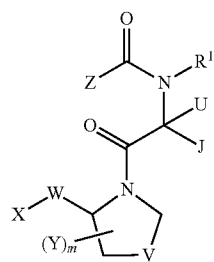

(7)

or a pharmaceutically acceptable salt or hydrate form thereof; and including any stereoisomeric forms thereof;

wherein J is H, CN, C1-C4 alkyl or C1-C4 alkyloxycarbonyl;

V is O or S;

each Y represents optionally substituted C1-C8 alkyl, C5-C12 aryl, C5-C20 arylalkyl, or a heteroform of one of these; or is =O, OR, SR, S(O)R, $SO_2R$, $SO_2NR_2$, $NR_2$, $OC(O)R$, $NRC(O)R$, NRCOOR, $NRC(O)NR_2$, $NRSO_2R$, CN, $C(O)NR_2$, C(O)R, COOR, $NO_2$ or halo, wherein each R is independently H, $C_1$-$C_8$ alkyl, C5-C12 aryl or C5-C20 arylalkyl, or a heteroform of one of these; or is any other substituent suitable for an alkyl group;

and wherein two Y groups on the same ring can cyclize to form a 3-6 membered ring that can be saturated, unsaturated or aromatic, and which ring may include a heteroatom selected from O, S and N as a ring member and may be substituted;

W represents C=O, C=S, or an optionally substituted $C_2$-$C_6$ alkylene or $C_2$-$C_6$ heteroalkylene; or W can be a bond where X comprises an optionally substituted 5-membered or 6-membered aryl or heteroaryl ring;

X represents an optionally substituted C5-C20 ring system comprising at least one aromatic ring and up to four heteroatoms selected from N, O and S, and can represent either a single 5-15 membered cyclic group or two 5-10 membered cyclic groups that are both attached to the same atom of W, provided that each X contains at least one aryl or heteroaryl ring;

U represents C1-C8 alkyl, C1-C8 heteroalkyl, C2-C8 alkenyl, C2-C8 heteroalkenyl, C2-C8 alkynyl, C2-C8 heteroalkynyl, C5-C12 aryl, C5-C12 heteroaryl, C5-C20 arylalkyl or C5-C20 heteroarylalkyl, each of which may be optionally substituted;

m is 0-4;

$R^1$ is H or optionally substituted C1-C4 alkyl; and

Z is an optionally substituted C1-C6 aminoalkyl wherein the amine may be in a protected or unprotected form.

In another aspect, the invention provides a compound of formula (8):

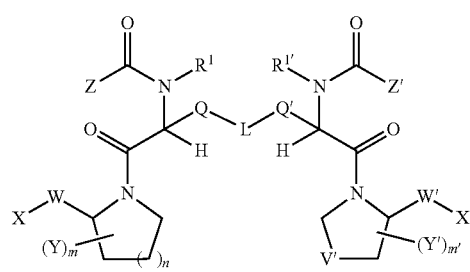

(8)

or a pharmaceutically acceptable salt or hydrate form thereof; and including any stereoisomeric forms thereof;

wherein V' is O or S;

each Y and Y' independently represents optionally substituted C1-C8 alkyl, C5-C12 aryl, C5-C20 arylalkyl, or a heteroform of one of these; or =O, OR, $NR_2$, OC(O)R, NRC(O)R, wherein each R is independently H or $C_1$-$C_8$ alkyl, C5-C12 aryl or C5-C20 arylalkyl, or a heteroform of one of these;

each W and W' independently represents C=O, C=S, or an optionally substituted $C_2$-$C_6$ alkylene or $C_2$-$C_6$ heteroalkylene; or W can be a bond where X comprises an optionally substituted C5-C6 aryl or heteroaryl ring, and/or W' can be a bond where X' comprises an optionally substituted C5-C6 aryl or heteroaryl ring;

each X and X' independently represents an optionally substituted C5-C20 ring system comprising at least one aromatic ring and up to four heteroatoms selected from N, O and S as a ring member, and can represent either a single 5-15 membered cyclic group or two 5-10 membered cyclic groups that are both attached to the same atom of W or W', provided that each X and X' comprises at least one aryl or heteroaryl ring;

each Q and Q' independently represents —CH$_2$—, —CH(OR)—, —CH(R)—, —CH$_2$O—, —CH(R)O—, or —(CH$_2$)$_4$NH— wherein R is H, or C$_1$-C$_4$ alkyl or C$_1$-C$_4$ heteroalkyl; or one or both of Q and Q' can be a bond where L comprises a ring;

n is 0-3;

each m and m' is independently 0-4;

each R$^1$ and R$^{1'}$ is independently H or optionally substituted C1-C4 alkyl;

each Z and Z' is independently an optionally substituted C1-C6 aminoalkyl; and

L represents a C2-C8 alkylene, C5-C12 arylene, or C5-C20 arylalkylene linker, or a heteroform of one of these, each of which may be optionally substituted and may be saturated or unsaturated;

with the proviso that L does not comprise a disulfide bond.

In another aspect, the invention provides a compound of formula (9):

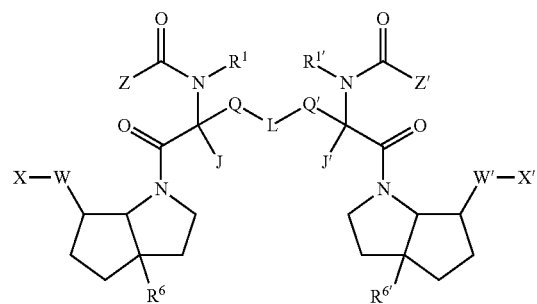

(9)

or a pharmaceutically acceptable salt or hydrate form thereof; and including any stereoisomeric forms thereof;

wherein each J and J' is independently H, CN, C1-C4 alkyl or C1-C4 alkoxycarbonyl;

each R$^6$ and R$^{6'}$ is independently H, C1-C4 alkyl or C1-C4 heteroalkyl;

each W and W' independently represents C=O, C=S, or an optionally substituted C$_2$-C$_6$ alkylene or C$_2$-C$_6$ heteroalkylene; or W can be a bond where X comprises an optionally substituted C5-C6 aryl or heteroaryl ring, and/or W' can be a bond where X' comprises an optionally substituted C5-C6 aryl or heteroaryl ring;

each X and X' independently represents an optionally substituted C5-C20 ring system comprising at least one aromatic ring and up to four heteroatoms selected from N, O and S as a ring member, and can represent either a single 5-15 membered cyclic group or two 5-10 membered cyclic groups that are both attached to the same atom of W or W', provided that each X and X' comprises at least one aryl or heteroaryl ring;

each Q and Q' independently represents —CH$_2$—, —CH(OR)—, —CH(R)—, —(CH$_2$)$_r$D-, —CH(R)D-, or —CR=CR— or —C≡C—, wherein r is 1-4, each D is independently O, NR, or S, and wherein each R is independently H, C$_1$-C$_8$ alkyl or C$_1$-C$_8$ heteroalkyl; or one or both of Q and Q' can be a bond where L comprises a ring;

each R$^1$ and R$^{1'}$ is independently H or optionally substituted C1-C4 alkyl;

each Z and Z' is independently an optionally substituted C1-C6 aminoalkyl; and

L represents a linker that is a C2-C20 hydrocarbyl group, optionally containing from 1-6 heteroatoms selected from N, O and S, which linker is 2 to 10 atoms in length when counted along the shortest path between Q and Q', and which may be optionally substituted;

with the proviso that L does not comprise a disulfide bond.

In another aspect, the invention provides a monomer of formula (10), and methods of using them for the preparation of compounds of formula (9), (11)-(12) or (17):

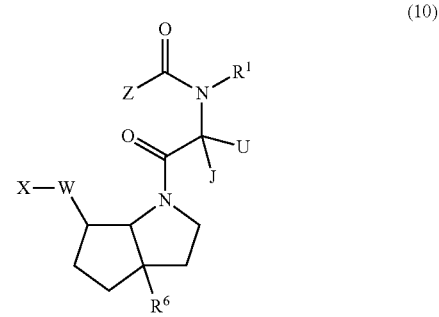

(10)

or a pharmaceutically acceptable salt or hydrate form thereof; and including any stereoisomeric forms thereof;

wherein J is H, CN, C1-C4 alkyl or C1-C4 alkoxycarbonyl;

R$^6$ is H, C1-C4 alkyl or C1-C4 heteroalkyl;

W represents C=O, C=S, or an optionally substituted C$_2$-C$_6$ alkylene or C$_2$-C$_6$ heteroalkylene; or W can be a bond where X comprises an optionally substituted 5-membered or 6-membered aryl or heteroaryl ring;

X represents an optionally substituted C5-C20 ring system comprising at least one aromatic ring and up to four heteroatoms selected from N, O and S, and can represent either a single 5-15 membered cyclic group or two 5-10 membered cyclic groups that are both attached to the same atom of W, provided that each X contains at least one aryl or heteroaryl ring;

U represents C1-C8 alkyl, C1-C8 heteroalkyl, C2-C8 alkenyl, C2-C8 heteroalkenyl, C2-C8 alkynyl, C2-C8 heteroalkynyl, C5-C12 aryl, C5-C12 heteroaryl, C5-C20 arylalkyl or C5-C20 heteroarylalkyl, each of which may be optionally substituted;

R$^1$ is H or optionally substituted C1-C4 alkyl; and

Z is an optionally substituted C1-C6 aminoalkyl wherein the amine may be in a protected or unprotected form.

In another aspect, the invention provides a compound of formula (11):

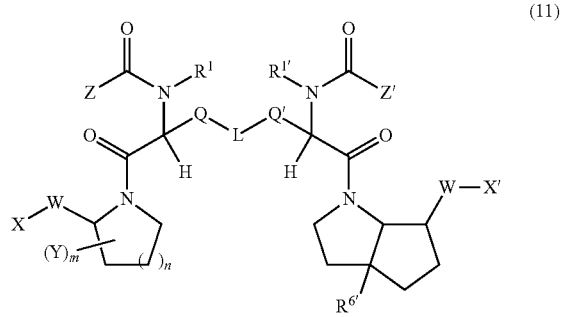

(11)

or a pharmaceutically acceptable salt or hydrate form thereof; and including any stereoisomeric forms thereof;

wherein $R^{6'}$ is H, C1-C4 alkyl or C1-C4 heteroalkyl;

each Y independently represents optionally substituted C1-C8 alkyl, C5-C12 aryl, C5-C20 arylalkyl, or a heteroform of one of these; or is =O, OR, NR$_2$, OC(O)R, NRC(O)R, wherein each R is independently H or $C_1$-$C_8$ alkyl, C5-C12 aryl or C5-C20 arylalkyl, or a heteroform of one of these;

each W and W' independently represents C=O, C=S, or an optionally substituted $C_2$-$C_6$ alkylene or $C_2$-$C_6$ heteroalkylene; or W can be a bond where X comprises an optionally substituted C5-C6 aryl or heteroaryl ring, and/or W' can be a bond where X' comprises an optionally substituted C5-C6 aryl or heteroaryl ring;

each X and X' independently represents an optionally substituted C5-C20 ring system comprising at least one aromatic ring and up to four heteroatoms selected from N, O and S as a ring member, and can represent either a single 5-15 membered cyclic group or two 5-10 membered cyclic groups that are both attached to the same atom of W or W', provided that each X and X' comprises at least one aryl or heteroaryl ring;

each Q and Q' independently represents —CH$_2$—, —CH(OR)—, —CH(R)—, —CH$_2$O—, —CH(R)O—, or —(CH$_2$)$_4$ NH—, wherein R is H, or $C_1$-$C_4$ alkyl or $C_1$-$C_4$ heteroalkyl; or one or both of Q and Q' can be a bond where L comprises a ring;

n is 0-3;

m is 0-4;

each $R^1$ and $R^{1'}$ is independently H or optionally substituted C1-C4 alkyl;

each Z and Z' is independently an optionally substituted C1-C6 aminoalkyl; and

L represents a C2-C8 alkylene, C5-C12 arylene, or C5-C20 arylalkylene linker, or a heteroform of one of these, each of which may be optionally substituted and may be saturated or unsaturated;

with the proviso that L does not comprise a disulfide bond.

In another aspect, the invention provides a compound of formula (12):

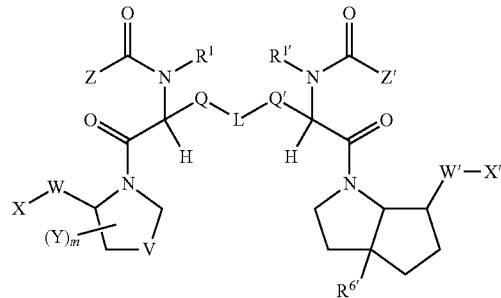

(12)

or a pharmaceutically acceptable salt or hydrate form thereof; and including any stereoisomeric forms thereof;

wherein $R^{6'}$ is H, C1-C4 alkyl or C1-C4 heteroalkyl;

V is O or S;

each Y independently represents optionally substituted C1-C8 alkyl, C5-C12 aryl, C5-C20 arylalkyl, or a heteroform of one of these; or is =O, OR, NR$_2$, OC(O)R, NRC(O)R, wherein each R is independently H or $C_1$-$C_8$ alkyl, C5-C12 aryl or C5-C20 arylalkyl, or a heteroform of one of these;

each W and W' independently represents C=O, C=S, or an optionally substituted $C_2$-$C_6$ alkylene or optionally substituted $C_2$-$C_6$ heteroalkylene; or W can be a bond where X comprises an optionally substituted C5-C6 aryl or heteroaryl ring, and/or W' can be a bond where X' comprises an optionally substituted C5-C6 aryl or heteroaryl ring;

each X and X' independently represents an optionally substituted C5-C20 ring system comprising at least one aromatic ring and up to four heteroatoms selected from N, O and S as a ring member, and can represent either a single 5-15 membered cyclic group or two 5-10 membered cyclic groups that are both attached to the same atom of W or W', provided that each X and X' comprises at least one aryl or heteroaryl ring;

each Q and Q' independently represents —CH$_2$—, —CH(OR)—, —CH(R)—, —CH$_2$O—, —CH(R)O—, or —(CH$_2$)$_4$ NH—, wherein R is H, or $C_1$-$C_4$ alkyl or $C_1$-$C_4$ heteroalkyl; or one or both of Q and Q' can be a bond where L comprises a ring;

m is 0-4;

each $R^1$ and $R^{1'}$ is independently H or optionally substituted C1-C4 alkyl;

each Z and Z' is independently an optionally substituted C1-C6 aminoalkyl; and

L represents a C2-C8 alkylene, C5-C12 arylene, or C5-C20 arylalkylene linker, or a heteroform of one of these, each of which may be optionally substituted and may be saturated or unsaturated;

with the proviso that L does not comprise a disulfide bond.

In another aspect, the invention provides a compound of formula (13):

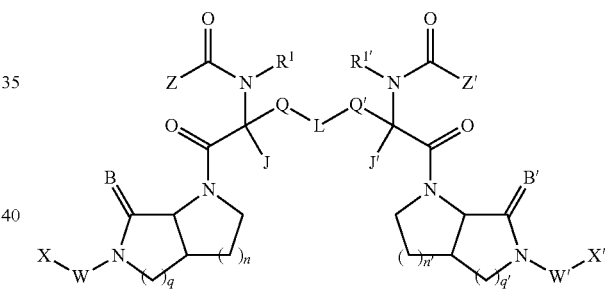

(13)

or a pharmaceutically acceptable salt or hydrate form thereof; and including any stereoisomeric forms thereof;

wherein each J and J' is independently H, CN, C1-C4 alkyl or C1-C4 alkoxycarbonyl;

each =B and =B' independently represents =O, =S, F$_2$ or H$_2$;

each W and W' independently represents C=O, C=S, or an optionally substituted $C_2$-$C_6$ alkylene or $C_2$-$C_6$ heteroalkylene; or W can be a bond where X comprises an optionally substituted C5-C6 aryl or heteroaryl ring, and/or W' can be a bond where X' comprises an optionally substituted C5-C6 aryl or heteroaryl ring;

each X and X' independently represents an optionally substituted C5-C20 ring system comprising at least one aromatic ring and up to four heteroatoms selected from N, O and S as a ring member, and can represent either a single 5-15 membered cyclic group or two 5-10 membered cyclic groups that are both attached to the same atom of W or W', provided that each X and X' comprises at least one aryl or heteroaryl ring;

each Q and Q' independently represents —CH$_2$—, —CH(OR)—, —CH(R)—, —(CH$_2$)$_r$D-, —CH(R)D-, or —CR=CR— or wherein r is 1-4, each D is independently O, NR, or S, and wherein each R is independently H, optionally substituted $C_1$-$C_8$ alkyl or optionally substituted $C_1$-$C_8$ heteroalkyl; or one or both of Q and Q' can be a bond where L comprises a ring;

each n and n' is independently 0-3;

each q and q' is independently 1-4;

each $R^1$ and $R^{1'}$ is independently H or optionally substituted C1-C4 alkyl;

each Z and Z' is independently an optionally substituted C1-C6 aminoalkyl; and

L represents a linker that is a C2-C20 hydrocarbyl group, optionally containing from 1-6 heteroatoms selected from N, O and S, which linker is 2 to 10 atoms in length when counted along the shortest path between Q and Q', and which may be optionally substituted;

with the proviso that L does not comprise a disulfide bond.

In another aspect, the invention provides a monomer of formula (14), and methods of using them for the preparation of compounds of formula (13) or (15)-(17):

(14)

or a pharmaceutically acceptable salt or hydrate form thereof; and including any stereoisomeric forms thereof;

wherein J is H, CN, C1-C4 alkyl or C1-C4 alkoxycarbonyl;

=B represents =O, =S, $F_2$ or $H_2$;

W represents C=O, C=S, or an optionally substituted $C_2$-$C_6$ alkylene or $C_2$-$C_6$ heteroalkylene; or W a can be a bond where X comprises a 5-membered or 6-membered aryl or heteroaryl ring;

X represents an optionally substituted C5-C20 ring system comprising at least one aromatic ring and up to four heteroatoms selected from N, O and S, and can represent either a single 5-15 membered cyclic group or two 5-10 membered cyclic groups that are both attached to the same atom of W, provided that each X comprises at least one aryl or heteroaryl ring;

U represents C1-C8 alkyl, C1-C8 heteroalkyl, C2-C8 alkenyl, C2-C8 heteroalkenyl, C2-C8 alkynyl, C2-C8 heteroalkynyl, C5-C12 aryl, C5-C12 heteroaryl, C5-C20 arylalkyl or C5-C20 heteroarylalkyl, each of which may be optionally substituted;

n is 0-3;

q is 1-4;

$R^1$ is H or optionally substituted C1-C4 alkyl; and

Z is an optionally substituted C1-C6 aminoalkyl wherein the amine may be in a protected or unprotected form.

In another aspect, the invention provides a compound of formula (15):

(15)

or a pharmaceutically acceptable salt or hydrate form thereof; and including any stereoisomeric forms thereof;

wherein =B' represents =O, =S, $F_2$ or $H_2$;

each Y independently represents optionally substituted C1-C8 alkyl, C5-C12 aryl, C5-C20 arylalkyl, or a heteroform of one of these; or is =O, OR, $NR_2$, OC(O)R, NRC(O)R, wherein each R is independently H or $C_1$-$C_8$ alkyl, C5-C12 aryl or C5-C20 arylalkyl, or a heteroform of one of these;

each W and W' independently represents C=O, C=S, or an optionally substituted $C_2$-$C_6$ alkylene or $C_2$-$C_6$ heteroalkylene; or W can be a bond where X comprises an optionally substituted C5-C6 aryl or heteroaryl ring, and/or W' can be a bond where X' comprises an optionally substituted C5-C6 aryl or heteroaryl ring;

each X and X' independently represents an optionally substituted C5-C20 ring system comprising at least one aromatic ring and up to four heteroatoms selected from N, O and S as a ring member, and can represent either a single 5-15 membered cyclic group or two 5-10 membered cyclic groups that are both attached to the same atom of W or W', provided that each X and X' comprises at least one aryl or heteroaryl ring;

each Q and Q' independently represents —$CH_2$—, —CH(OR)—, —CH(R)—, —$CH_2$O—, —CH(R)O—, or —($CH_2$)$_4$ NH—, wherein R is H, or $C_1$-$C_4$ alkyl or $C_1$-$C_4$ heteroalkyl; or one or both of Q and Q' can be a bond where L comprises a ring;

each n and n' is independently 0-3;

m is 0-4;

q' is 1-4;

each $R^1$ and $R^{1'}$ is independently H or optionally substituted C1-C4 alkyl;

each Z and Z' is independently an optionally substituted C1-C6 aminoalkyl; and

L represents a C2-C8 alkylene, C5-C12 arylene, or C5-C20 arylalkylene linker, or a heteroform of one of these, each of which may be optionally substituted and may be saturated or unsaturated;

with the proviso that L does not comprise a disulfide bond.

In another aspect, the invention provides a compound of formula (16):

(16)

or a pharmaceutically acceptable salt or hydrate form thereof; and including any stereoisomeric forms thereof;

wherein =B' represents =O, =S, F$_2$ or H$_2$;

V is O or S;

each Y independently represents optionally substituted C1-C8 alkyl, C5-C12 aryl, C5-C20 arylalkyl, or a heteroform of one of these; or is =O, OR, NR$_2$, OC(O)R, NRC(O)R, wherein each R is independently H or C$_1$-C$_8$ alkyl, C5-C12 aryl or C5-C20 arylalkyl, or a heteroform of one of these;

each W and W' independently represents C=O, C=S, or an optionally substituted C$_2$-C$_6$ alkylene or C$_2$-C$_6$ heteroalkylene; or W can be a bond where X comprises an optionally substituted C5-C6 aryl or heteroaryl ring, and/or W' can be a bond where X' comprises an optionally substituted C5-C6 aryl or heteroaryl ring;

each X and X' independently represents an optionally substituted C5-C20 ring system comprising at least one aromatic ring and up to four heteroatoms selected from N, O and S as a ring member, and can represent either a single 5-15 membered cyclic group or two 5-10 membered cyclic groups that are both attached to the same atom of W or W', provided that each X and X' comprises at least one aryl or heteroaryl ring;

each Q and Q' independently represents —CH$_2$—, —CH(OR)—, —CH(R)—, —CH$_2$O—, —CH(R)O—, or —(CH$_2$)$_4$ NH—, wherein R is H, or C$_1$-C$_4$ alkyl or C$_1$-C$_4$ heteroalkyl; or one or both of Q and Q' can be a bond where L comprises a ring;

n' is 0-3;

m is 0-4;

q' is 1-4;

each R$^1$ and R$^{1'}$ is independently H or optionally substituted C1-C4 alkyl;

each Z and Z' is independently an optionally substituted C1-C6 aminoalkyl; and

L represents a C2-C8 alkylene, C5-C12 arylene, or C5-C20 arylalkylene linker, or a heteroform of one of these, each of which may be optionally substituted and may be saturated or unsaturated;

with the proviso that L does not comprise a disulfide bond.

In another aspect, the invention provides a compound of formula (17):

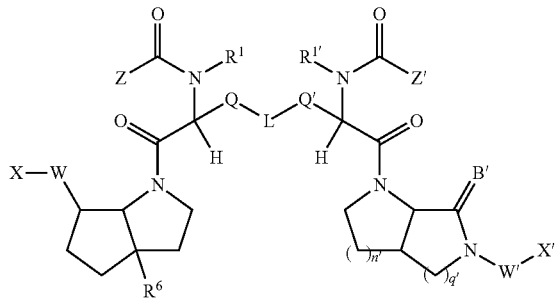

(17)

or a pharmaceutically acceptable salt or hydrate form thereof; and including any stereoisomeric forms thereof;

wherein =B' represents =O, =S, F$_2$ or H$_2$;

R$^6$ is H, C1-C4 alkyl or C1-C4 heteroalkyl;

each W and W' independently represents C=O, C=S, or an optionally substituted C$_2$-C$_6$ alkylene or C$_2$-C$_6$ heteroalkylene; or W can be a bond where X comprises an optionally substituted C5-C6 aryl or heteroaryl ring, and/or W' can be a bond where X' comprises an optionally substituted C5-C6 aryl or heteroaryl ring;

each X and X' independently represents an optionally substituted C5-C20 ring system comprising at least one aromatic ring and up to four heteroatoms selected from N, O and S as a ring member, and can represent either a single 5-15 membered cyclic group or two 5-10 membered cyclic groups that are both attached to the same atom of W or W', provided that each X and X' comprises at least one aryl or heteroaryl ring;

each Q and Q' independently represents —CH$_2$—, —CH(OR)—, —CH(R)—, —CH$_2$O—, —CH(R)O—, or —(CH$_2$)$_4$ NH—, wherein R is H, or C$_1$-C$_4$ alkyl or C$_1$-C$_4$ heteroalkyl; or one or both of Q and Q' can be a bond where L comprises a ring;

n' is 0-3;

q' is 1-4;

each R$^1$ and R$^{1'}$ is independently H or optionally substituted C1-C4 alkyl;

each Z and Z' is independently an optionally substituted C1-C6 aminoalkyl; and

L represents a C2-C8 alkylene, C5-C12 arylene, or C5-C20 arylalkylene linker, or a heteroform of one of these, each of which may be optionally substituted and may be saturated or unsaturated;

with the proviso that L does not comprise a disulfide bond.

The compounds of the invention synergize with TRAIL (TNF-related apoptosis inducing ligand), with etoposide, with TRAIL-related substances including a TRAIL receptor antibody or TNF-α, and with anti-cancer drugs to overcome the apoptosis-inhibiting activity of caspase inhibiting proteins. Without being bound by theory, the present compounds are believed to act by binding to IAP, thus preventing IAP from binding to and inhibiting caspases. This frees the caspases to initiate apoptosis. Accordingly, the compounds of the invention can promote apoptosis in cells that are abnormally resistant to it, which are typically pathogenic cells.

For example, compounds of the invention induce apoptosis in glioblastoma cell culture, typically at picomolar concentrations. The compounds provide new adjuvant chemotherapeutics for cancers, particularly those that resist programmed cell death by over-expressing IAP proteins. The compounds are stable, protease resistant, and freely membrane permeant. The compounds are not by themselves cytotoxic, however, they are believed to operate by overcoming protective mechanisms that some pathogenic cells such as cancer cells use to prevent apoptosis.

Accordingly, the invention also provides methods and compositions for enhancing apoptosis of pathogenic cells using pro-apoptotic dimeric or dimer-like small molecules that are referred to as Smac mimetics. The compositions include at least one compound of any of formulas (I), (1)-(3), (5)-(6), (8)-(9), (11)-(13) or (15)-(17) admixed with at least one pharmaceutically acceptable excipient. In some embodiments, the compositions further include at least one additional cancer therapeutic whose activity is synergized or potentiated by the Smac mimetic activity of the compounds of the invention. Examples of such additional cancer therapeutics include, without limitation, antimetabolites (e.g. cytarabine, fludaragine, 5-fluoro-2'-deoxyuridine, gemcitabine, hydroxyurea and methotrexate), DNA active agents (e.g. bleomycin, chlorambucil, cisplatin and cyclophosphamide), intercalating agents (e.g. adriamycin and mitoxantrone), protein synthesis inhibitors (e.g. L-asparaginase, cycloheximide and puromycin); topoisomerase inhibitors of Type I class (e.g. camptothecin, topotecan and irinotecan) and Type II class (e.g. etoposide, teniposide, anthraquinones, anthracyclines and podophyllotoxin), microtubule inhibitors (e.g. docetaxel, paclitaxel, colcemid, colchicines, vinblastine and vincristine), kinase inhibitors (e.g. flavopiridol, staurosporin and hydroxystaurosporine), drugs that affect Hsp90 (e.g. geldanomycin and geldanomycin derivatives, radicicol, purine derivatives and antibodies or antibody fragments that selectively bind to Hsp90), and/or radiation therapy.

The general method for enhancing or inducing apoptosis comprises the step of contacting a cell with an effective amount of a Smac mimetic compound, optionally followed by the step of detecting, directly, indirectly or inferentially, a resultant increase in apoptosis of the target cells. It may also include a step of identifying or diagnosing a subject in need of such treatment, particularly a subject having one of the conditions described herein as being treated or alleviated by a Smac mimetic.

In preferred embodiments, the cells are in situ in an individual diagnosed as in need of an apoptosis promoting treatment, and the contacting step is effected by administering to the individual a pharmaceutical composition including a therapeutically effective amount of the mimetic, wherein the individual may be subject to concurrent or antecedent radiation or chemotherapy for treatment of a neoproliferative pathology. In particular embodiments, the pathogenic cells are of a tumor, such as glioblastoma, astrocytoma, breast cancer, prostate cancer, lung cancer, pancreatic cancer, gastric cancer, colon cancer, ovarian cancer, renal cancer, hepatoma, melanoma, lymphoma, or sarcoma.

In additional embodiments, the target cells are pro-inflammatory cells or cells of tissue subject to pathogenic inflammation and/or autoimmunity. A wide variety of diseases involve such pathogenic inflammation, including rheumatoid arthritis, diabetes, asthma, lupus, myasthenia gravis, Graves disease, inflammatory bowel disease (e.g. Crohn's disease, ulcerative colitis and related conditions), pelvic inflammatory diseases, chronic obstructive pulmonary disease (COPD), chronic bronchitis, pneumoconiosis, pulmonary emphysema, interstitial lung fibrosis, allergic rhinitis (hay fever), inflammatory cardiovascular diseases (e.g. congestive heart failure and ischemia/reperfusion injuries), atherosclerosis (including coronary artery disease), stroke, neurodegenerative diseases, such as Alzheimer's disease, multiple sclerosis and amyotrophic lateral sclerosis (ALS), neuroinflammatory diseases, organ transplant rejection, autoimmune hematological disorders, psoriasis, sclerodoma, chronic active hepatitis, primary biliary cirrhosis, glomerulonephritis, uveitis and keratoconjunctivitis.

The subject compositions encompass pharmaceutical compositions containing a therapeutically effective amount of an active, dimer-like Smac mimetic as described above in dosage form, and a pharmaceutically acceptable excipient, such as a carrier or diluent. In some embodiments, such compositions also contain an additional therapeutic agent, such as an anti-neoproliferative chemotherapeutic agent, in addition to the Smac mimetic.

MODES OF CARRYING OUT THE INVENTION

The present invention may be understood more readily by reference to the following detailed description of the preferred embodiments of the invention and the Examples included herein. It is to be understood that the terminology used herein is for the purpose of describing specific embodiments only and is not intended to be limiting. It is further to be understood that unless specifically defined herein, the terminology used herein is to be given its traditional meaning as known in the relevant art.

As used herein, the singular form "a", "an", and "the" include plural references unless indicated otherwise. For example, "a" dimer includes one of more dimers.

As used herein, a "therapeutically effective amount" is an amount required to produce a desired therapeutic effect in a tissue, system, animal, or human, that is being sought, e.g., by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, "subject" refers to a human or animal subject. In certain preferred embodiments, the subject is human.

As used herein, "hydrocarbyl residue" refers to a residue which contains only carbon and hydrogen, unless otherwise provided. The residue may be aliphatic or aromatic, straight-chain, cyclic, branched, saturated or unsaturated, or any combination of these. The hydrocarbyl residue, when so stated, however, may contain heteroatoms in addition to or instead of the carbon and hydrogen members of the hydrocarbyl group itself. Thus, when specifically noted as containing or optionally containing heteroatoms, the hydrocarbyl group may contain one or more heteroatoms as indicated within the "backbone" of the hydrocarbyl residue, and when optionally substituted, the hydrocarbyl residue may also have one or more carbonyl groups, amino groups, hydroxyl groups and other suitable substituents as further described herein in place of one or more hydrogens of the parent hydrocarbyl residue.

As used herein, the terms "alkyl," "alkenyl" and "alkynyl" include straight-chain, branched-chain and cyclic monovalent hydrocarbyl radicals, and combinations of these, which contain only C and H when they are unsubstituted. Examples include methyl, ethyl, isobutyl, cyclohexyl, cyclopentylethyl, 2-propenyl, 3-butynyl, and the like. The total number of carbon atoms in each such group is sometimes described herein, e.g., when the group can contain up to ten carbon atoms it may be described as 1-10C or as C1-C10 or as C1-10 or as $C_{1-10}$. When heteroatoms (typically N, O and S) are allowed to replace carbon atoms of an alkyl, alkenyl or alkynyl group, as in heteroalkyl groups, for example, the numbers describing the group, though still written as e.g. C1-C6, represent the sum of the number of carbon atoms in the group plus the number of such heteroatoms that are included as replacements for carbon atoms in the ring or chain being described.

Typically, the alkyl, alkenyl and alkynyl substituents of the invention contain 1-10C (alkyl) or 2-10C (alkenyl or alkynyl). Preferably they contain 1-8C (alkyl) or 2-8C (alkenyl or alkynyl). Sometimes they contain 1-4C (alkyl) or 2-4C (alkenyl or alkynyl). A single group can include more than one type of multiple bond, or more than one multiple bond; such groups are included within the definition of the term "alkenyl" when they contain at least one carbon-carbon double bond, and they are included within the term "alkynyl" when they contain at least one carbon-carbon triple bond.

Alkyl, alkenyl and alkynyl groups are often substituted to the extent that such substitution makes sense chemically. Typical substituents include, but are not limited to, halo, =O, =N—CN, =N—OR, =NR, OR, $NR_2$, SR, SOR, $SO_2R$, $SO_2NR_2$, $NRSO_2R$, $NRCONR_2$, NRCOOR, NRCOR, CN, COOR, $CONR_2$, OOCR, COR, and $NO_2$, wherein each R is independently H, C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C5-C12 aryl, C5-C12 heteroaryl, C5-C20 arylalkyl, or C5-C20 heteroarylalkyl, and each R is optionally substituted with one or more groups selected from halo, =O, =N—CN, =N—OR', =NR', OR', NR'$_2$, SR', SOR', SO$_2$R', SO$_2$NR'$_2$, NR'SO$_2$R', NR'CONR'$_2$, NR'COOR', NR'COR', CN, COOR', CONR'$_2$, OOCR', COR', and NO$_2$, wherein each R' is independently H, C1-C8 alkyl, C2-C8 heteroalkyl, C1-C8 acyl, C2-C8 heteroacyl, C5-C12 aryl, C5-C12 heteroaryl, C5-C20 arylalkyl, or C5-C20 heteroarylalkyl. Alkyl, alkenyl and alkynyl groups can also be substituted by C1-C8 acyl, C2-C8 heteroacyl, C5-C12 aryl or C5-C12 heteroaryl, each of which can be substituted by the substituents that are appropriate for the particular group.

"Heteroalkyl", "heteroalkenyl", and "heteroalkynyl" and the like are defined similarly to the corresponding hydrocarbyl (alkyl, alkenyl and alkynyl) groups, but the 'hetero' terms refer to groups that contain one or more heteroatoms selected from O, S and N and combinations thereof, within the backbone residue; thus at least one carbon atom of a corresponding alkyl, alkenyl, or alkynyl group is replaced by one of the specified heteroatoms to form a heteroalkyl, heteroalkenyl, or heteroalkynyl group. Preferably, each heteroalkyl, heteroalkenyl and heteroalkynyl group contains only 1-2 heteroatoms as part of the skeleton of backbone of the heteroalkyl group, i.e., not including substituents that may be present.

The typical and preferred sizes for heteroforms of alkyl, alkenyl and alkynyl groups are generally the same as for the corresponding hydrocarbyl groups, and the substituents that may be present on the heteroforms are the same as those described above for the hydrocarbyl groups. Where such groups contain N, the nitrogen atom may be present as NH or it may be substituted if the heteroalkyl or similar group is described as optionally substituted. Where such groups contain S, the sulfur atom may optionally be oxidized to SO or SO$_2$ unless otherwise indicated. For reasons of chemical stability, it is also understood that, unless otherwise specified, such groups do not include more than two contiguous heteroatoms as part of the heteroalkyl chain, although an oxo group may be present on N or S as in a nitro or sulfonyl group. Thus —C(O)NH$_2$ can be a C2 heteroalkyl group substituted with =O; and —SO$_2$NH— can be a C2 heteroalkylene, where S replaces one carbon, N replaces one carbon, and S is substituted with two =O groups.

While "alkyl" as used herein includes cycloalkyl and cycloalkylalkyl groups, the term "cycloalkyl" may be used herein to specifically describe a carbocyclic non-aromatic group that is connected via a ring carbon atom, and "cycloalkylalkyl" may be used to describe a carbocyclic non-aromatic group that is connected to the base molecule through an alkyl linker. Similarly, "heterocyclyl" may be used to describe a non-aromatic cyclic group that contains at least one heteroatom as a ring member and that is connected to the molecule via a ring atom of the cyclic group, which may be C or N; and "heterocyclylalkyl" may be used to describe such a group that is connected to another molecule through an alkyl linker. The sizes and substituents that are suitable for the cycloalkyl, cycloalkylalkyl, heterocyclyl, and heterocyclylalkyl groups are the same as those described above for alkyl groups. The size of a cycloalkylalkyl or heterocyclylalkyl group describes the total number of carbon atoms or of carbon atoms plus heteroatoms that replace carbon atoms of an alkyl, alkenyl, alkynyl, cycloalkyl, or alkylenyl portion. As used herein, these terms also include rings that contain a double bond or two, as long as the ring is not aromatic.

As used herein, "acyl" encompasses groups comprising an alkyl, alkenyl, alkynyl, aryl or arylalkyl radical attached at one of the two available valence positions of a carbonyl carbon atom, e.g., —C(=O)R where R is an alkyl, alkenyl, alkynyl, aryl, or arylalkyl group, and heteroacyl refers to the corresponding groups wherein at least one carbon other than the carbonyl carbon has been replaced by a heteroatom chosen from N, O and S. Thus heteroacyl includes, for example, —C(=O)OR and —C(=O)NR$_2$ as well as —C(=O)-heteroaryl.

Acyl and heteroacyl groups are bonded to any group or molecule to which they are attached through the open valence of the carbonyl carbon atom. Typically, they are C1-C8 acyl groups, which include formyl, acetyl, pivaloyl, and benzoyl, and C2-C8 heteroacyl groups, which include methoxyacetyl, ethoxycarbonyl, and 4-pyridinoyl. The hydrocarbyl groups, aryl groups, and heteroforms of such groups that comprise an acyl or heteroacyl group can be substituted with the substituents described herein as generally suitable substituents for each of the corresponding component of the acyl or heteroacyl group.

As used herein, the terms "thioacyl" and "heterothioacyl" encompass groups comprising an alkyl, alkenyl, alkynyl, aryl or arylalkyl radical, or a heteroform of one of these, attached at one of the two available valence positions of a thiocarbonyl carbon atom, e.g., —C(=S)R where R is an alkyl, alkenyl, alkynyl, aryl, or arylalkyl group "Aromatic" moiety or "aryl" moiety refers to a monocyclic or fused bicyclic moiety having the well-known characteristics of aromaticity; examples include phenyl and naphthyl. Similarly, "heteroaromatic" and "heteroaryl" refer to such monocyclic or fused bicyclic ring systems which contain as ring members one or more heteroatoms selected from O, S and N. The inclusion of a heteroatom permits aromaticity in 5-membered rings as well as 6-membered rings. Typical heteroaromatic systems include monocyclic C5-C6 aromatic groups such as pyridyl, pyrimidyl, pyrazinyl, pyridazinyl, triazinyl, thienyl, furanyl, pyrrolyl, pyrazolyl, thiazolyl, isothiazolyl, oxazolyl, isoxazolyl, imidazolyl, triazolyl, thiadiazolyl, oxadiazolyl, and tetrazolyl rings, and the fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolinyl, quinolinyl, benzothiazolyl, benzofuranyl, benzothienyl, benzisoxazolyl, pyrazolopyridyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least one ring has the characteristics of aromaticity, even though it may be fused to a nonaromatic ring. Typically, the ring systems contain 5-12 ring member atoms. Preferably the monocyclic heteroaryl groups contain 5-6 ring members, and the bicyclic heteroaryls contain 8-10 ring members.

Aryl and heteroaryl moieties may be substituted with a variety of substituents including C1-C8 alkyl, C2-C8 alkenyl, C2-C8 alkynyl, C5-C12 aryl, C1-C8 acyl, C5-20 arylalkyl, and heteroforms of these, each of which can itself be further substituted; other substituents for aryl and heteroaryl moieties include halo, OR, NR$_2$, SR, SOR, SO$_2$R, SO$_2$NR$_2$, NRSO$_2$R, NRCONR$_2$, NRCOOR, NRCOR, CN, COOR, CONR$_2$, OOCR, C(O)R, and NO$_2$, wherein each R is independently H, C1-C8 alkyl, C2-C8 heteroalkyl, C2-C8 alkenyl, C2-C8 heteroalkenyl, C2-C8 alkynyl, C2-C8 heteroalkynyl, C5-C12 aryl, C5-C12 heteroaryl, C5-C20 arylalkyl, or C5-C20 heteroarylalkyl, and each R is optionally substituted as described above for alkyl groups. The substituent groups on an aryl or heteroaryl group may of course be further substituted with the groups described herein as suitable for each type of group that comprises the substituent. Thus, for example, an arylalkyl substituent may be substituted on the aryl portion with substituents described herein as typical for aryl groups, and it may be further substituted on the alkyl portion with substituents described herein as typical or suitable for alkyl groups.

Similarly, "arylalkyl" and "heteroarylalkyl" refer to aromatic and heteroaromatic ring systems which are bonded to their attachment point through a linking group such as an alkylene, including substituted or unsubstituted, saturated or unsaturated, cyclic or acyclic linkers. Typically the linker is C1-C8 alkyl or a hetero form thereof. These linkers may also include a carbonyl or thiocarbonyl group, thus making them able to provide substituents as an acyl, heteroacyl, thioacyl or heterothioacyl moieties.

An aryl or heteroaryl ring in an arylalkyl or heteroarylalkyl group may be substituted with the same substituents described above for aryl groups. Preferably, an arylalkyl group includes a phenyl ring optionally substituted with the groups defined above for aryl groups and a C1-C4 alkylene that is unsubstituted or is substituted with one or two C1-C4 alkyl groups or C1-C4 heteroalkyl groups, where the alkyl or heteroalkyl groups can optionally cyclize to form a ring such as cyclopropane, dioxolane, or oxacyclopentane, and wherein the alkyl or heteroalkyl groups may be optionally fluorinated.

Similarly, a heteroarylalkyl group preferably includes a C5-C6 monocyclic heteroaryl group that is optionally substituted with the groups described above as substituents typical on aryl groups and a C1-C4 alkylene that is unsubstituted or is substituted with one or two C1-C4 alkyl groups or heteroalkyl groups, or it includes an optionally substituted phenyl ring or C5-C6 monocyclic heteroaryl and a C1-C4 heteroalkylene that is unsubstituted or is substituted with one or two C1-C4 alkyl or heteroalkyl groups, where the alkyl or heteroalkyl groups can optionally cyclize to form a ring such as cyclopropane, dioxolane, or oxacyclopentane.

Where an arylalkyl or heteroarylalkyl group is described as optionally substituted, the substituents may be on either the alkyl or heteroalkyl portion or on the aryl or heteroaryl portion of the group. The substituents optionally present on the alkyl or heteroalkyl portion are the same as those described above for alkyl groups generally; the substituents optionally present on the aryl or heteroaryl portion are the same as those described above for aryl groups generally.

"Arylalkyl" groups as used herein are hydrocarbyl groups if they are unsubstituted, and are described by the total number of carbon atoms in the ring and alkylene or similar linker. Thus a benzyl group is a C7-arylalkyl group, and phenylethyl is a C8-arylalkyl.

"Heteroarylalkyl" as described above refers to a moiety comprising an aryl group that is attached through a linking group, and differs from "arylalkyl" in that at least one ring atom of the aryl moiety or one atom in the linking group is a heteroatom selected from N, O and S. The heteroarylalkyl groups are described herein according to the total number of atoms in the ring and linker combined, and they include aryl groups linked through a heteroalkyl linker; heteroaryl groups linked through a hydrocarbyl linker such as an alkylene; and heteroaryl groups linked through a heteroalkyl linker. Thus, for example, C7-heteroarylalkyl would include pyridylmethyl, phenoxy, and N-pyrrolylmethoxy.

"Alkylene" as used herein refers to a divalent hydrocarbyl group; because it is divalent, it can link two other groups together. Typically it refers to $-(CH_2)_n-$ where n is 1-8 and preferably n is 1-4, though where specified, an alkylene can also be substituted by other groups, and can be of other lengths, and the open valences need not be at opposite ends of a chain. Thus $-CH(Me)-$ and $-C(Me)_2-$ may also be referred to as alkylenes, as can a cyclic group such as cyclopropan-1,1-diyl. However, for clarity, a three-atom linker that is an alkylene group, for example, refers to a divalent group in which the available valences for attachment to other groups are separated by three atoms such as $-(CH_2)_3-$, i.e., the specified length represents the number of atoms linking the attachment points rather than the total number of atoms in the hydrocarbyl group: $-C(Me)_2-$ would thus be a one-atom linker, since the available valences are separated by only one atom. Where an alkylene group is substituted, the substituents include those typically present on alkyl groups as described herein, thus $-C(=O)-$ is an example of a one-carbon substituted alkylene. Where it is described as unsaturated, the alkylene may contain one or more double or triple bonds.

"Heteroalkylene" as used herein is defined similarly to the corresponding alkylene groups, but the 'hetero' terms refer to groups that contain one or more heteroatoms selected from O, S and N and combinations thereof, within the backbone residue; thus at least one carbon atom of a corresponding alkylene group is replaced by one of the specified heteroatoms to form a heteroalkylene group. Thus, $-C(=O)NH-$ is an example of a two-carbon substituted heteroalkylene, where N replaces one carbon, and C is substituted with a $=O$ group.

In general, any alkyl, alkenyl, alkynyl, acyl, aryl or arylalkyl group or any heteroform of one of these groups that is contained in a substituent may itself be optionally substituted by additional substituents. The nature of these substituents is similar to those recited with regard to the primary substituents themselves if the substituents are not otherwise described. Thus, where an embodiment of, for example, $R^7$ is alkyl, this alkyl may optionally be substituted by the remaining substituents listed as embodiments for $R^7$ where this makes chemical sense, and where this does not undermine the size limit provided for the alkyl per se; e.g., alkyl substituted by alkyl or by alkenyl would simply extend the upper limit of carbon atoms for these embodiments, and is not intended to be included. However, alkyl substituted by halo, aryl, amino, alkoxy, $=O$, $=S$, and the like would be included within the scope of the invention, and the atoms of these substituent groups are not counted in the number used to describe the alkyl, alkenyl, etc. group that is being described. Where no number of substituents is specified, each such alkyl, alkenyl, alkynyl, acyl, or aryl group may be substituted with a number of substituents according to its available valences and in accord with known principles of chemical stability; in particular, any of these groups may be substituted with fluorine atoms at any or all of the available valences on carbon atoms, for example.

"Heteroform" as used herein refers to a derivative of a group such as an alkyl, aryl, or acyl, wherein at least one carbon atom of the designated carbocyclic group has been replaced by a heteroatom selected from N, O and S. Thus the heteroforms of alkyl, alkenyl, alkynyl, acyl, aryl, and arylalkyl are heteroalkyl, heteroalkenyl, heteroalkynyl, heteroacyl, heteroaryl, and heteroarylalkyl, respectively. It is understood that no more than two N, O or S atoms are ordinarily connected sequentially, except where an oxo group is attached to N or S to form a nitro or sulfonyl group, or in the case of certain heteroaromatic rings, such as triazine, triazole, tetrazole, oxadiazole, thiadiazole, and the like.

"Optionally substituted" as used herein indicates that the particular group or groups being described may have no non-hydrogen substituents, or the group or groups may have one or more non-hydrogen substituents. If not otherwise specified, the total number of such substituents that may be present is equal to the number of H atoms present on the unsubstituted form of the group being described. Where an optional substituent is attached via a double bond, such as a carbonyl oxygen ($=O$), the group takes up two available valences, so the total number of substituents that may be included is reduced according to the number of available valences.

"Halo", as used herein includes fluoro, chloro, bromo and iodo. Fluoro and chloro are often preferred.

"Amino" as used herein refers to NH$_2$, but where an amino is described as "substituted" or "optionally substituted", the term includes NR$_2$ wherein each R is independently H, or is an alkyl, alkenyl, alkynyl, acyl, thioacyl, aryl, or arylalkyl group or a heteroform of one of these groups, and each of the alkyl, alkenyl, alkynyl, acyl, thioacyl, aryl, or arylalkyl groups or heteroforms of one of these groups is optionally substituted with the substituents described herein as suitable for the corresponding type of group. The term also includes forms wherein the two R groups on one nitrogen atom are linked together to form a 3-8 membered monocyclic azacyclic ring or an 8-12 membered bicyclic fused azacyclic ring system, each of which may be saturated, unsaturated or aromatic and which may contain 1-3 heteroatoms independently selected from N, O and S as ring members, and which may be optionally substituted with the substituents described as suitable for alkyl groups or, if NR$_2$ is an aromatic group, it is optionally substituted with the substituents described as typical for heteroaryl groups.

As used herein, an 'azacyclic' group refers to a heterocyclic group containing at least one nitrogen as a ring atom, wherein the group is attached to the base molecule through a nitrogen atom of the azacyclic ring. Typically these azacyclic groups are 3-8 membered monocyclic rings or 8-12 membered bicyclic fused ring systems. An azacyclic group having more than four ring members can optionally include one additional heteroatom selected from N, O and S, and an azacyclic group having more than six ring members can optionally include one or two additional heteroatoms selected from N, O and S. Typically, an azacyclic group is non-aromatic, and such azacyclic groups can optionally be substituted with substituents that are suitable for alkyl groups. Typical examples of azacyclic groups include pyrrolidine, pyrrolidinone, piperidine, piperidinone, morpholine, thiomorpholine, and piperazine. In certain embodiments, an azacyclic group can be aromatic, provided that at least one ring nitrogen atom is in a five membered ring so the nitrogen can serve as the point of attachment to the base molecule. Non-limiting examples of aromatic systems that can be azacyclic groups include pyrrole, imidazole, pyrazole, triazole, tetrazole, or indole, indazole or benzimidazole.

The invention provides dimer and dimer-like compounds of formula (I) that possess two structurally similar binding domains, each of which includes a monocyclic or fused bicyclic ring system that is substituted by at least one aryl-containing group, —W—X. These two domains are linked by a linking group, and while similar, the domains need not be identical. In certain embodiments of formula (I), the two binding domains are the same, so the molecule is symmetric about its linking group.

The apoptosis-promoting compounds of the invention are sometimes described herein as 'dimers'. These 'dimers' include both symmetric dimers formed containing two identical monomers of, e.g., formula (4), or formula (7), or formula (10), or formula (14), as well as unsymmetrical dimers. The unsymmetrical dimers may contain two non-identical monomers of a single class (e.g., both are compounds of formula (4)), or they may contain monomers selected from different classes, e.g., a monomer of formula (4) with a monomer of formula (7) or (10) or (14).

In compounds of formula (I), the two amide-containing domains are linked together by a linkage depicted as Q-L-Q'. As further described herein for specific embodiments, this linkage can comprise numerous alternatives that can include a chain that may be substituted and may be saturated or unsaturated; it may also include a combination of cyclic and acyclic features. L is often a C2-C20 hydrocarbyl group, which may contain 1-2 heteroatoms in place of carbon atoms. In many embodiments, each Q and Q' represents a one or two atom alkylene or heteroalkylene group, each of which can be substituted, and L represents a C2-C20 hydrocarbyl linker, optionally containing from 1-6 heteroatoms selected from N, O and S, which is 2-10 atoms in length when counted along the shortest path between Q and Q', and wherein L can also be further substituted.

As used herein, an "azacyclic ring core" refers to an azacyclic ring which is selected from a saturated 3-8 membered monocyclic azacyclic ring and a saturated 8-12 membered fused polycyclic azacyclic ring, each of which may contain 0-2 additional heteroatoms selected from N, O, S, as ring members. In certain embodiments of formula (I), the azacyclic ring core comprising ring A and the azacyclic ring core comprising ring A' are different, meaning that their ring structures are different. In other embodiments of formula (I), the azacyclic ring core comprising ring A and the azacyclic ring core comprising ring A' are the same, meaning that their ring structures are the same, although they may be differentially substituted. In further embodiments, ring A and ring A' may comprise identical azacyclic ring cores, bearing identical substituents.

In compounds of formula (I), each of ring A and ring A' independently represents an azacyclic ring core which is selected from a saturated 3-8 membered monocyclic azacyclic ring and a saturated 8-12 membered fused polycyclic azacyclic ring, each of which may contain 0-2 additional heteroatoms selected from N, O, S as ring members; and wherein ring A is substituted with a group represented as —W—X, and ring A' is substituted with a group represented as W'—X', and each of ring A and ring A' may be optionally substituted with from 1-4 additional substituents suitable for its structure.

In compounds of formula (I), each J and J' is independently H, CN, C1-C4 alkyl or C1-C4 alkyloxycarbonyl; each R$^1$ and R$^{1'}$ is independently H or optionally substituted C1-C4 alkyl; and each Z and Z' is independently an optionally substituted C1-C6 aminoalkyl group.

In compounds of formula (I), each W and W' independently represents C=O, C=S, or an optionally substituted C$_2$-C$_6$ alkylene or C$_2$-C$_6$ heteroalkylene; or W can be a bond where X comprises an optionally substituted C5-C6 aryl or heteroaryl ring, and/or W' can be a bond where X' comprises an optionally substituted C5-C6 aryl or heteroaryl ring.

Each X and X' in formula (I) independently represents an optionally substituted C5-C20 ring system comprising at least one aromatic ring and up to four heteroatoms selected from N, O and S, and can represent either a single 5-15 membered cyclic group or two 5-10 membered cyclic groups that are both attached to the same atom of W or W', provided that each X and X' comprises at least one aryl or heteroaryl ring;

In compounds of formula (I), each Q and Q' independently represents —CH$_2$—, —CH(OR)—, —CH(R)—, —(CH$_2$)$_r$-D-, —CH(R)D-, or —CR=CR— or —C=C—, wherein r is 1-4, each D is independently O, NR, or S, and wherein each R is independently H, or optionally substituted C1-C8 alkyl or optionally substituted C1-C8 heteroalkyl; or one or both of Q and Q' can be a bond where L comprises a ring;

In preferred embodiments of formula (I), each of ring A and ring A' is an azacyclic ring core independently selected from the group consisting of:

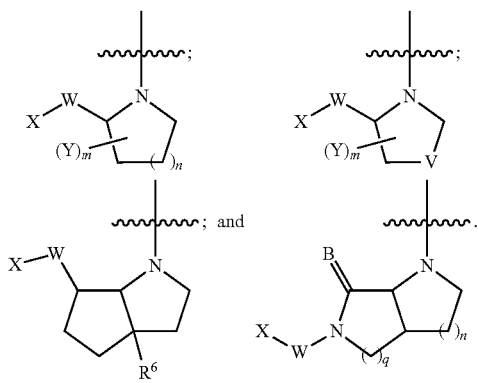

For such embodiments, where present, m is 0-4; n is 0-3; V is O or S; $R^6$ is independently H or C1-C4 alkyl; =B represents =O, =S, $H_2$ or $F_2$; and q is 1-4.

Each Y, where present, independently represents any substituent described herein as suitable for an alkyl group. For example, each Y can be optionally substituted C1-C8 alkyl, C5-C12 aryl, C5-C20 arylalkyl, or a heteroform of one of these; or is =O, OR, SR, S(O)R, $SO_2R$, $SO_2NR_2$, $NR_2$, OC(O)R, NRC(O)R, NRCOOR, $NRC(O)NR_2$, $NRSO_2R$, CN, $C(O)NR_2$, C(O)R, COOR, $NO_2$ or halo, wherein each R is independently H, $C_1$-$C_8$ alkyl, C5-C12 aryl or C5-C20 arylalkyl, or a heteroform of one of these. In further embodiments, two Y groups on the same ring can cyclize to form a 3-6 membered ring that can be saturated, unsaturated or aromatic, and which ring may include a heteroatom selected from O, S and N as a ring member and may be substituted; in certain embodiments, two Y groups on adjacent atoms can cyclize to form a phenyl ring that is fused to the azacyclic ring.

In another aspect, the invention provides a monomer of formula (II), and methods of using them for the preparation of compounds of formula (I), as further described herein.

For compounds of formula (II), each of ring A, and substituents J, $R^1$, W, X and Z are as described for formula (I).

In preferred embodiments of formula (II), ring A is an azacyclic ring core selected from the group consisting of:

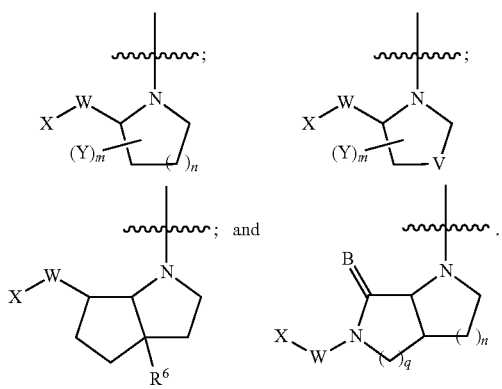

U in compounds of formula (II) represents a C1-C8 alkyl, C1-C8 heteroalkyl, C2-C8 alkenyl, C2-C8 heteroalkenyl, C2-C8 alkynyl, C2-C8 heteroalkynyl, C5-C12 aryl, C5-C12 heteroaryl, C5-C20 arylalkyl or C5-C20 heteroarylalkyl, each of which may be optionally substituted.

In compounds of formula (1), the two amide-containing domains are linked together by a linkage depicted as Q-L-Q'. This linkage can comprise numerous alternatives that can include a chain that may be substituted and/or unsaturated; it may also include a combination of cyclic and acyclic features. In many embodiments, each Q and Q' represents a one or two atom alkylene or heteroalkylene group, each of which can be substituted, and L represents a C2-C20 hydrocarbyl linker, optionally containing from 1-6 heteroatoms selected from N, O and S, which is 2-10 atoms in length when counted along the shortest path between Q and Q', and wherein L can also be further substituted.

In formula (1), L is a linker that connects Q and Q', and the connection between Q and Q' is 2-10 atoms in length when counted along the shortest path between Q and Q'. L is often a C2-C20 hydrocarbyl group, which may contain 1-2 heteroatoms in place of carbon atoms. L can be substituted as described herein with substituents that are suitable for its structure. L can comprise one or more rings as part of the linker connecting Q and Q', which ring or rings may form the linker or may be fused to the linking atoms that form the shortest path between Q and Q'. In many embodiments, L is an acyclic alkylene or an unsaturated alkylene (alkenylene or alkynylene), which may be substituted. In certain embodiments, such alkylene linker is preferably unsaturated, and may be an alkynylene linker. In some embodiments, L is symmetric, and frequently L is 4-6 atoms in length, counting along the shortest path (by atom count) between Q and Q'. L can also include one or two heteroatoms selected from N, O and S, but does not include a disulfide linkage.

L can be substituted by substituents including rings, and it can comprise one or more rings as part of the linkage that connects Q and Q' together. Where L comprises at least one ring that is part of or is fused to the shortest path (by atom count) connecting Q and Q', Q and/or Q' in formula (1) can be a bond as well as any of the other structures described herein for Q and Q'. Where L comprises a ring, the ring(s) may be cycloalkyl, heterocyclyl, aryl, or heteroaryl, and may be further substituted. Such rings can be connected to Q and/or Q' (or, where Q and/or Q' represents a bond, the rings can be connected by the bond Q or Q' directly to the carbon to which J or J' is attached), at any ring position, and may be attached either directly or through an intervening alkylene or heteroalkylene group, provided the shortest path (by atom counting) between Q and Q' consists of 2-10 atoms, and preferably 2-4 atoms or 4-6 atoms. For example, L could be a cyclohexan-1,4-diyl linker, or a 1,3-disubstituted aryl or heteroaryl linker, or a biaryl linker where Q is attached to one ring of the biaryl and Q' is attached to the other ring of the biaryl.

In some embodiments, L comprises a phenyl ring that may be 1,2-disubstituted, or 1,3-disubstituted, or 1,4-disubstituted, by the groups Q and Q', which may be directly attached to the ring or may be separated from the ring by one or more atoms that are included in L. In some such embodiments this phenyl ring is connected directly to Q or Q' and the Q or Q' to which that phenyl is attached is either $CH_2$ or a bond. For example, such compounds can be derived from phenylglycine, phenylalanine or tyrosine derivatives. In some such embodiments, Q-L-Q' represents a structure selected from the following group:

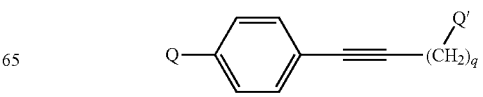

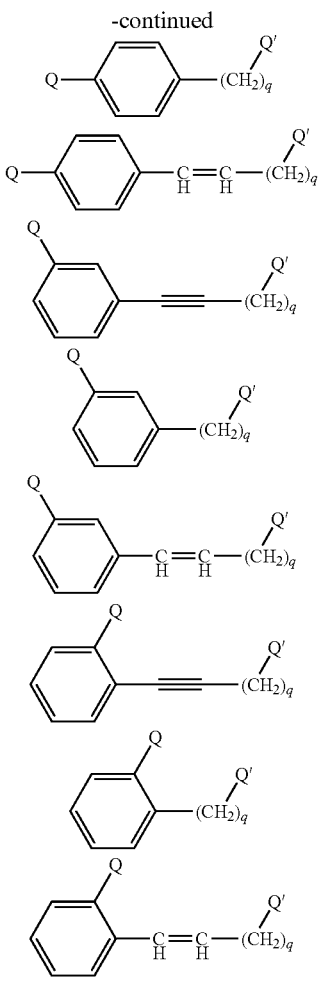

wherein each q is independently 0-4, and each phenyl ring is optionally substituted with 1-2 groups selected from C1-C4 alkyl, C1-C4 alkoxy, CF$_3$, and halo. Q and Q' in these embodiments are as defined for formula (1), and in some preferred embodiments, Q is either a bond or CH$_2$.

In other embodiments, L comprises at least one triazole ring that is part of the linker between Q and Q'. In certain embodiments, each Q and Q' independently represents a bond, —CH$_2$— or —CH(R)O—, where R is H or methyl. In specific embodiments, Q-L-Q' represents a group selected from:

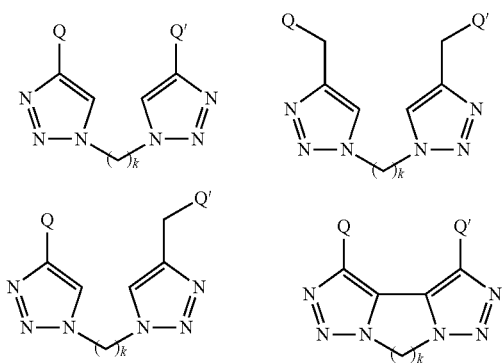

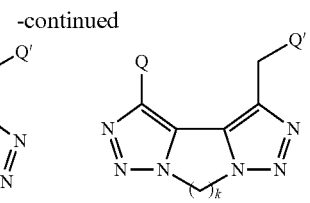

wherein each k is independently 1-4.

In certain embodiments, L is a saturated or unsaturated alkylene group that is 2-8 atoms in length along the shortest path connecting Q and Q', and may be substituted. Some saturated embodiments of L include 1,3-propylene, 1,4-butylene, 1,5-pentylene and 1,6-hexylene, or 1,4-cyclohexylene, each of which can be substituted. When L is unsaturated, it is sometimes 1,4-but-2-enylene (—CH$_2$—CH=CH—CH$_2$—), 1,4-buta-1,3-dienylene (—CH=CH—CH=CH); 1,4-buta-1,3-diynylene (—C≡C—C≡C—); or an optionally substituted version of one of these. Alternatively, L can be an aryl ring such as 1,2- or 1,3- or 1,4-disubstituted phenyl or pyridyl, or it can be an aryl ring and an alkylene group, or an aryl ring and two alkylene groups combined, for example it can be —CH$_2$—Ar— or —CH$_2$—Ar—CH$_2$—, where Ar represents a 5- or 6-membered aromatic or heteroaromatic ring. L can also include one or more heteroatoms, for example, it can be —O—Ar—O— or —S—Ar— or —NH—Ar—CH$_2$— or a substituted version of one of these.

The same groups described here for L in compounds of formula (1) are also suitable for L in compounds of formulas (2)-(3), (5)-(6), (8)-(9), (11)-(13) or (15)-(17).

In compounds of formula (1), each Q and Q' independently represents a one or two carbon alkylene or heteroalkylene group. For example, each Q and Q' can independently be —CH$_2$—, —CH(OR)—, —CH(R)—, —CH(R)D-, wherein r is 1-4 and each D is independently O, NR, or S, or each Q and Q' can independently be an unsaturated two-carbon linker such as —CR=CR— or wherein each R is independently H, or optionally substituted C$_1$-C$_8$ alkyl or optionally substituted C$_1$-C$_8$ heteroalkyl; or one or both of Q and Q' can be a bond where L comprises a ring. A preferred embodiment for each Q and Q' is methylene (—CH$_2$—), or alkyl-substituted methylene, for example —CH(Me)-, or Q and/or Q' can be —CH$_2$O— or —(CH$_2$)$_4$NH—.

In some embodiments of formula (1), each of Q and/or Q' can also represent a bond when L comprises a ring, as described above. In embodiments where L comprises a ring, Q and Q' are often independently a bond or —CH$_2$—, and in some embodiments Q or Q' can be —CH$_2$O— or —CH(Me)O—.

The same groups as described here for Q and Q' in compounds of formula (1) are also suitable for Q and Q' in compounds of formulas (2), (5)-(6), (8)-(9), (11)-(13) or (15)-(17).

In compounds of formula (2) and (3), L is sometimes a 3-8 atom linker that is typically an alkylene or alkenylene or alkynylene, or a heteroform of one of these, each of which may be substituted. Frequently L is symmetric, about its central atom (if the chain connecting the two available valences is an odd number of atoms in length) or its central bond (if the chain connecting the two available valences is an even number of atoms in length).

In compounds of formula (1), n and n' can independently be 0-3, and in some embodiments n and n' are the same. In certain embodiments n and n' are each selected from 1 and 2 and can be the same or different; in specific embodiments, n and n' are both 1.

In compounds of formula (1), J and J' can be H, CN, C1-C4 alkyl or C1-C4 alkyloxycarbonyl. In many embodiments, J and J' are each selected from H and methyl. In certain embodiments both J and J' are the same, and both may be H. The groups described here for J and J' in compounds of formula (1) are also suitable for J and/or J' in compounds of formulas (4), (5), (7), (9), (10), (13) or (14).

In compounds of any of formulas (1) to (17), $(Y)_m$ and $(Y')_{m'}$, and where present, independently represent one or more substituents (up to four substituents) optionally present on the nitrogen-containing ring. Each of m and m' may be 0-4, and in certain embodiments, the two binding domains may be differently substituted. However, in certain embodiments m and m' are the same. In many embodiments, each of m and m' is either 0 or 1. Specific embodiments include m=m'=1 and m=m'=0.

Where m or m' is other than zero, each Y and each Y' present is independently selected from the substituents described herein as suitable for alkyl groups. In some embodiments where m is 1, Y or Y' or both may represent a carbonyl (=O). In other embodiments where m is 1-4, each Y and Y' is C1-C4 alkyl or C1-C4 alkyloxy. In certain embodiments, two Y groups on a single nitrogen-containing ring can cyclize to form a ring having 3-6 ring members and optionally containing one heteroatom (N, O or S) as a ring member, and in one such embodiment two Y groups on adjacent atoms may be cyclized together to form an aryl ring, such as a phenyl ring, that is fused to the nitrogen-containing ring shown. The aryl ring in such embodiments may be substituted with the groups described herein as suitable substituents for aryl rings.

In compounds of any of formulas (I), (II), and (1) to (17), each $R^1$ and $R^{1'}$, where present, is independently selected from H and C1-C4 alkyl; if $R^1$ and $R^{1'}$ represents alkyl, it may optionally be substituted; in some embodiments it is substituted with a carbonyl adjacent to the N to which the $R^1$ and $R^{1'}$ is attached, providing an acyl group. One embodiment of $R^1$ and $R^{1'}$ is thus formyl or acetyl or methoxyacetyl. In preferred embodiments, one or both of $R^1$ and $R^{1'}$ represent H.

Each of Z and/or Z' in compounds of formula (I), (II), (1), (2) and (4) through (17) is an optionally substituted C1-C6 aminoalkyl group. This can be a C1-C6 alkyl group that is substituted with at least one amine group and is optionally substituted with one or more other groups suitable as substituents for an alkyl group. In some embodiments, Z or Z' can be a 1-aminoalkyl group such as a 1-aminomethyl or 1-aminoethyl or 1-aminopropyl, where the amine group is substituted with one or two optionally substituted C1-C8 alkyl groups, and may also be substituted with a C1-C8 acyl or heteroacyl group. Examples of acyl or heteroacyl groups useful on the amine of this aminoalkyl group include —C(O)Me, —C(O)CF$_3$, —C(O)CH(R)NH$_2$, and the like.

A typical embodiment of Z or Z' is 1-aminopropyl, or 1-aminoethyl or aminomethyl, or 1-methylaminopropyl, or 1-methylaminoethyl or methylaminomethyl. Alternatively, Z or Z' can be 1-ethylaminomethyl or 1-ethylaminoethyl. Where Z or Z' has a chiral center adjacent to the carbonyl to which it is connected, the chiral center may have either the (R) or the (S) configuration. For specific embodiments, it is sometimes preferably in the (S) absolute configuration. In certain embodiments, Z and Z' are the same, though they can be different.

In certain embodiments of formulas (II), (4), (7), (10) and (14), Z is often a protected amine. One of skill in the art would appreciate that appropriate amine protecting groups may vary depending on the functionality present in the particular monomer. Suitably protected amines may include, for example, amines protected as carbamates (e.g. tert-butoxycarbonyl, benzlyoxycarbonyl, fluorenylmethyloxy-carbonyl, allyloxycarbonyl or (trialkylsilyl)ethoxycarbonyl), carboxamides (e.g. formyl, acyl or trifluoroacetyl), sulfonamides, phthalimides, Schiff base derivatives, and the like. Where Z is a protected amine, it is sometimes desirable to remove the protecting group after coupling two of the 'monomers' to form a dimeric compound. Thus, the method of making a compound a dimeric compound of formula (I), (1), (2), (3), (5), (6), (8), (9), (11), (12), (13), (15), (16) or (17), as described herein also optionally includes a step of removing any protecting groups on the amine Z (and/or Z').

In compounds of formulas (I), (II) and (1) to (17), each W and W', where present, may independently represent a carbonyl (C=O), a thiocarbonyl (C=S) or an optionally substituted C2-C6 alkylene or C2-C6 heteroalkylene linker to which X or X' is attached. Thus, each —W—X (and/or —W'—X') can represent a group of the form —C(O)NR—(CHR)$_p$—X, where p is 0, 1 or 2 and each R is H or a C1-C4 alkyl or C1-C4 heteroalkyl group. In specific embodiments, each —W—X and —W'—X' independently represents —C(O)NR—(CHR)$_p$—X, where p is 0 or 1 and each R is H or methyl. In some such embodiments, X or X' is an optionally substituted phenyl ring; or two phenyl rings, each of which may be optionally substituted; or is a tetrahydronaphthyl, indanyl or fluorenyl ring system; or is an optionally substituted 5- or 6-membered heteroaromatic ring containing 1-4 heteroatoms selected from N, O or S. In specific embodiments, X and/or X' comprises a phenyl, thiazole or tetrazole ring, optionally substituted by one or more substituents described herein as preferred substituents when present on an aryl or heteroaryl ring that is part of X or X'. In some such embodiments, X and/or X' comprises a thiazole or tetrazole ring substituted with at least one C5-C12 aryl, C5-C12 heteroaryl, C5-C12 arylalkyl or C5-C12 heteroarylalkyl group, each of which may be further substituted. Preferably, the thiazole or tetrazole ring is substituted with an optionally substituted phenyl ring, an optionally substituted naphthyl ring, or a benzyl group.

In other embodiments of formulas (I), (II), and (1) to (17), W and/or W' represents a C2-C6 alkylene or C2-C6 heteroalkylene linker. For example, each of W and/or W' independently represents a group of the form —(CH$_2$)$_p$—, —CH$_2$—O—(CH$_2$)$_p$—, —CH$_2$S(CH$_2$)$_p$—, —CH$_2$S(O)(CH$_2$)$_p$—, —CH$_2$SO$_2$(CH$_2$)$_p$—, —CH$_2$NR(CH$_2$)$_p$—, or —CH$_2$NRSO$_2$(CH$_2$)$_p$—, where p is 0, 1, or 2, and R is H, or is optionally substituted C1-C8 alkyl or C5-C12 arylalkyl. In some such embodiments, X and/or X' represents an optionally substituted phenyl ring, or a tetrahydronaphthyl or indanyl ring system.

In further embodiments of formulas (I), (II), and (1) to (17), W may be a bond where X comprises an optionally substituted C5-C6 aryl or heteroaryl ring and/or W' maybe a bond where X' comprises an optionally substituted C5-C6 aryl or heteroaryl ring. In some such embodiments, each X and/or X' comprises a phenyl, pyridyl, pyrimidyl, pyrazinyl, pyridazinyl, triazinyl, thienyl, furanyl, pyrrolyl, pyrazolyl, thiazolyl, isothiazolyl, oxazolyl, isoxazolyl, imidazolyl, triazolyl, thiadiazolyl, oxadiazolyl, or tetrazolyl ring, each of which may be optionally substituted, as further described herein.

In certain embodiments, W and/or W' is a bond, where X and/or X' comprises a phenyl, pyridyl, pyrimidyl, thiazole or tetrazole ring, each of which may be optionally substituted. In specific embodiments, X and/or X' comprises a phenyl, pyridyl or pyrimidinyl ring, preferably substituted with $CH_2R$, $CF_2R$, $C(O)R$, $OR$, $SR$, $S(O)R$, $SO_2R$, or $NR_2$, where each R is independently H, C1-C4 alkyl, $CF_3$, or an optionally substituted C5-C6 aryl or optionally substituted C5-C6 heteroaryl ring. In other preferred embodiments, X and/or X' comprises a substituted phenyl ring which is a diphenylmethane, phenoxyphenyl, thiophenoxyphenyl, benzophenone, or N-phenyl benzeneamine ring; preferably, the substituent on the phenyl ring is oriented meta to the bond represented as W and/or W'.

In some embodiments, W represents a bond where X comprises an optionally substituted thiazole ring or an optionally substituted tetrazole ring. In other embodiments, W' represents a bond where X' comprises an optionally substituted thiazole ring or an optionally substituted tetrazole ring. In certain embodiments, X and/or X' comprises a triazole or tetrazole ring substituted with at least one C5-C12 aryl, C5-C12 heteroaryl, C5-C12 arylalkyl or C5-C12 heteroarylalkyl group. In preferred embodiments, X and/or X' is substituted with at least one phenyl or naphthyl ring, wherein said phenyl or naphthyl ring may itself be further substituted by substituents described herein as suitable for aryl rings.

Each of W and W' may be independently selected, so they can be the same or different; in some embodiments, W and W' are the same.

Each of X and/or X' in compounds of formulas (I), (II), and (1)-(17), where present, represents a C5-C20 ring system comprising at least one aryl or heteroaryl group and up to four heteroatoms as ring members, and can be a single 5-15 membered cyclic group or it can be two 5-10 membered cyclic groups that are both attached to a single atom of W. Each of these cyclic groups can be a single ring, a fused ring system, or linked rings such as a biaryl group. Optionally, each X and X' can be substituted and can include up to four heteroatoms selected from O, N and S. Thus by way of example, each X and X' can comprise an aryl or heteroaryl ring, which can be monocyclic or bicyclic provided at least one ring of a bicyclic group is aromatic, or it can represent two 5-10 membered cyclic group provided that at least one of them comprises an aryl or heteroaryl ring.

In specific embodiments of compounds of formulas (I), (II), and (1)-(17), each X and/or X', where present, can comprise a phenyl, naphthyl, biphenyl, pyridyl, pyrimidyl, pyrazinyl, pyridazinyl, triazinyl, thienyl, furanyl, pyrrolyl, pyrazolyl, thiazolyl, isothiazolyl, oxazolyl, isoxazolyl, imidazolyl, triazolyl, thiadiazolyl, oxadiazolyl, or tetrazolyl ring, each of which may be optionally substituted; or X and/or X' can comprise the fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolinyl, quinolinyl, benzothiazolyl, benzofuranyl, benzothienyl, benzisoxazolyl, benzoxadiazole, benzthiadiazole, pyrazolopyridyl, quinazolinyl, quinoxalinyl, cinnolinyl, and the like; or X and/or X' can comprise a 5- or 6-membered saturated ring fused to a 5- or 6-membered aryl or heteroaryl ring, such as a tetrahydronaphthyl ring system, an indanyl ring system, a fluorenyl ring system, or similar fused ring system having two aromatic or heteroaromatic rings or having a saturated or partially unsaturated 5- or 6-membered carbocyclic or heterocyclic ring fused to a 5- or 6-membered aryl or heteroaryl ring, each of which can be substituted on either or both rings.

In some preferred embodiments, X and/or X' can be a phenyl ring, which can be substituted; or two phenyl rings on one atom of W or W', which can be substituted on one or both phenyl rings; or X and/or X' can be a tetrahydronaphthyl group or an indanyl group; or X and/or X' can be an optionally substituted 5- or 6-membered heteroaromatic ring containing 1-4 heteroatoms selected from N, O, and S. In certain preferred embodiments, X and/or X' comprises an optionally substituted thiazole ring or an optionally substituted tetrazole ring.

Each of X and X' may be independently selected, and can be the same or different; in some embodiments they are the same.

When X or X' comprises a 5- or 6-membered saturated ring fused to a 5- or 6-membered aryl or heteroaryl ring, in some embodiments, X or X' is attached to W or W' through an atom in the saturated ring. For example, X or X' can represent a tetrahydronaphthyl or indanyl ring system, wherein each X or X' is attached to W or W' through any carbon atom in the saturated 5- or 6-membered ring.

In certain embodiments, X or X' comprises one or two aryl or heteroaryl rings, preferably one or two phenyl rings; and each aryl or heteroaryl ring is attached to W or W' through a terminal carbon atom of W or W'. For example, —W—X or —W'—X' can comprise a benzyl, phenethyl, pyridylmethyl, diphenylmethyl group, or the like, wherein the aryl or heteroaryl ring in any of these embodiments may be optionally substituted.

In further embodiments, X and/or X' comprises a 5-membered heteroaromatic ring which is a thienyl, furanyl, pyrrolyl, pyrazolyl, thiazolyl, isothiazolyl, oxazolyl, isoxazolyl, imidazolyl, triazolyl, thiadiazolyl, oxadiazolyl, or tetrazolyl ring, each of which may be optionally substituted.

Preferred substituents when present on an aryl or heteroaryl ring that is part of X or X' include C1-C4 alkyl, C1-4 heteroalkyl, C1-C4 alkenyl, C1-4 heteroalkenyl, C1-C4 alkynyl, C1-4 heteroalkynyl, OR, $NR_2$, SR, $S(O)R$, $SO_2R$, $C(O)R$, C5-12 aryl, C5-12 heteroaryl, C5-12 arylalkyl, C5-12 heteroarylalkyl, and halo, where each R is independently H, or C1-C4 alkyl, C1-C4 heteroalkyl, C5-C12 aryl, C5-C12 heteroaryl, C5-C12 arylalkyl, or C5-C12 heteroarylalkyl, each of which may be further substituted with groups suitable for its structure; and wherein any alkyl or arylalkyl substituent may be optionally fluorinated on the alkyl portion.

For compounds of formula (2), m, Q, W, X, Y and Z are as described for formula (1), and the compound contains two of the amino acid-derived binding domains that have the same formula, but may differ in stereochemistry. Frequently, m is 0 or 1, and where m is 1, Y is often carbonyl, C1-C4 alkyl or C1-C4 alkoxy. For compounds of formula (2), Q is preferably —$CH_2$—, —CH(OR)—, —CH(R)—, —$CH_2$O—, —CH(R)O—, or —$(CH_2)_4$NH—, wherein R is H, or $C_1$-$C_4$ alkyl or $C_1$-$C_4$ heteroalkyl. In many embodiments, Q is —$CH_2$— or —CH(Me)-. In certain embodiments, Q is a bond where L comprises a ring. Any of the groups described for L in formula (1) is suitable for L in compounds of formula (2). In preferred embodiments of formula (2), L represents a $C_2$-$C_8$ alkylene, C5-C12 arylene, or C5-C20 arylalkylene linker, or a heteroform of one of these, each of which may be optionally substituted and may be saturated or unsaturated. In some of these embodiments, X—W— represents X—NH—C(=O)—.

In compounds of formula (3), m, W, X and Y are as described above for compounds of formula (1) and/or (2), and L is as described above for compounds of formula (2). $R^4$ can be H, OH or an optionally substituted C1-C8 alkyl or heteroalkyl group. In many embodiments, $R^4$ represents H or methyl. In other embodiments, $R^4$ represents OH.

In certain embodiments, W in formula (3) represents an amide linker, and —W—X represents —C(O)NR(CHR)$_p$—X, where p is 0, 1 or 2 and each R is H or a C1-C4 alkyl group. In some embodiments, —W—X preferably comprises an arylalkyl group such as benzyl, phenethyl, or diphenylmethyl, or X is a tetrahydronaphthyl or indanyl group linked to nitrogen of W through an open valence on the saturated ring of the tetrahydronaphthyl or indanyl ring system. In other embodiments, X represents a 5-membered heteroaryl ring containing 1-4 heteroatoms selected from N, O and S. In preferred embodiments, —W—X represents —C(O)NR(CHR)$_p$—X, where p is 0 or 1, and each R is H or methyl; in some of these embodiments, —W—X represents —C(O)NH—X. In other embodiments, W represents a bond, where X comprises an optionally substituted 5- or 6-membered aryl or heteroaryl ring. In certain embodiments, W is a bond where X is an optionally substituted phenyl, optionally substituted thiazole or optionally substituted tetrazole ring.

$R^3$ in formula (3) can be H or an optionally substituted C1-C8 alkyl or C1-C8 heteroalkyl group, and can optionally cyclize with $R^2$ if an $R^2$ is other than H. In certain embodiments, $R^3$ is H or a C1-C4 alkyl group such as methyl, ethyl or propyl.

Each $R^2$ in formula (3) can be H or a C1-C8 alkyl or heteroalkyl, each of which is optionally substituted as described herein for alkyl groups. If two $R^2$ groups other than H are present on one nitrogen atom, they can optionally cyclize to form an azacyclic group as further described herein, which azacyclic ring is optionally substituted and can contain one or two additional heteroatoms selected from N, O and S.

Compounds of formula (4) represent monomers useful for the preparation of dimer and dimer-like compounds, such as, e.g., the compounds of formulas (1)-(3), (8), (11) or (15). A suitable monomer is a molecule that can be readily covalently linked to a second monomer molecule which may be identical or different, to form a dimer or dimer-like Smac mimetic compound as described above. Monomers may be linked directly to form dimers, or may be linked through reaction with a third molecule containing at least two reactive centers, as further described herein. Accordingly, compounds encompassed in the present invention include both dimer and dimer-like molecules and monomeric intermediates useful for the synthesis of such dimeric compounds.

For compounds of formula (4), each of J, n, m, $R^1$, W, X, Y and Z are as described herein for compounds of formula (1)-(3). In preferred embodiments, J is H, $R^1$ is H or methyl, n is 1, and m is 0 or 1.

U in monomers of formula (4) represents C1-C8 alkyl, C1-C8 heteroalkyl, C2-C8 alkenyl, C2-C8 heteroalkenyl, C2-C8 alkynyl, C2-C8 heteroalkynyl, C5-C12 aryl, C5-C12 heteroaryl, C5-C20 arylalkyl or C5-C20 heteroarylalkyl, each of which may be optionally substituted, and with the proviso that U is not isopropyl. Optional substituents may include one or more functional groups that can be used for further chemistry.

U in formula (4) preferably comprises at least one functional group that can be used to connect two monomers, which may be the same or different, to form a dimer of formula (I). Thus, U generally comprises at least one functional group such as acyl, alkenyl, alkynyl, azido, amino, hydroxyl, alkoxyl, carboxyl, carbonyl, sulfonyloxy, halo or the like, capable of participating in a chemical reaction so that two monomers, each having a group U with such functional groups present can be linked together using conventional transformations to form a dimer of formula (1). In certain preferred embodiments, U comprises a terminal alkyne, terminal alkene, aminoalkyl, phenol, aryl triflate or aryl halide moiety. In particular embodiments, two monomers of formula (4) are reacted to give dimers of formula (1), (2), or (3).

For example, if each of two monomers of formula (4) comprises a terminal acetylene group, coupling of the two acetylenes can be used to form a dimer, as illustrated herein.

If each of two monomers contains an olefin, preferably a terminal olefin, olefin metathesis can be used to link the monomers to form a dimer. Where each of two monomers contains a free amine as part of U, two monomers can be linked together with a difunctional acylating agent (e.g., succinyl chloride, or a bis-sulfonyl halide, or the like). Where U of each monomer includes an acyl group, two monomers can be linked by a diol or diamine to form a dimer with an ester or amide linkage in Q-L-Q'.

When an unsymmetrical dimer of formula (1) is desired, two monomers having complementary functional groups can be combined. For example, a monomer having a free carboxylate group may be coupled to a monomer having an unprotected amine group using conventional amide forming reactions to provide a dimer wherein the monomers are linked by a bridging group containing an amide. Coupling of a monomer containing a terminal alkyne to a monomer containing an aryl triflate or aryl halide may be used to provide dimers wherein the linker comprises an arylalkyne moiety; coupling of an aryl triflate containing monomer with an aryl boronic acid may be used to provide a biaryl dimer. Cycloaddition of a monomer containing an azide to an alkyne-containing monomer may be used to provide dimers wherein the linker comprises a triazole ring.

Alternatively, two monomers may be brought together by reaction with a third molecule containing at least two reactive centers, such as the reaction of two amine containing monomers with carbonyldimidazole to form a urea-containing linker; the reaction of two hydroxyl containing monomers with 1,4-dichloro-2-butene to form a dimer linked by an alkenyl chain; or the reaction of two alkyne containing monomers with a bis-azide containing molecule to form a dimer wherein the linker comprises two triazole rings.

Dimeric molecules may also undergo further reaction. For example, dimers containing alkenyl or alkynyl bonds may be fully or partially reduced to give alkyl or alkenyl bonds. Acetylene or bis-acetylene containing dimers may undergo cyclization reactions with mono- or bis-azido containing molecules to give polycyclic triazole containing linkers.

In certain embodiments of formula (4), U is an optionally substituted alkynyl or heteroalkynyl group of three to six atoms. In other embodiments of formula (4), U is (CH$_2$)$_r$Ar, where r is 0, 1 or 2 and Ar is a phenyl ring substituted with a functional group that allows convenient coupling to another monomer. In specific embodiments, Ar comprises a phenol, an aryl triflate or an aryl halide.

In some embodiments of formula (4), W is an amide linker, and —W—X represents —C(O)NR—(CHR)$_p$—X, where p is 0, 1 or 2 and each R is H or a C1-C4 alkyl group. In other embodiments, W is a bond where X comprises a 5- or 6-membered aryl or heteroaryl ring. In certain embodiments, X is an optionally substituted phenyl ring, or two phenyl rings attached to the same atom of W, or is a tetrahydronaphthyl or indanyl group linked to nitrogen of W through an open valence on the saturated ring of the tetrahydronaphthyl or indanyl ring system. In other embodiments, X is an optionally substituted 5- or 6-membered aryl or heteroaryl ring containing 1-4 heteroatoms selected from N, O and S. In specific embodiments, X is a pyridyl, pyrimidyl, pyrazinyl, pyridazinyl, triazinyl, thienyl, furanyl, pyrrolyl, pyrazolyl, thiazolyl, isothiazolyl, oxazolyl, isoxazolyl, imidazolyl, triazolyl, thiadiazolyl, oxadiazolyl, or tetrazolyl ring, each of which may be optionally substituted.

In compounds of formula (4), Z is an optionally substituted C1-C6 aminoalkyl which may contain a protected amine group. In some embodiments of formula (4), Z can be a 1-aminoalkyl group, such as a 1-aminomethyl or 1-aminoethyl or 1-aminopropyl, where the amine group is substituted with one or two optionally substituted C1-C8 alkyl groups, and may also be substituted with a C1-C8 acyl or heteroacyl group. In many embodiments of formula (4), the amine is often protected using a typical amine protecting group, to give a carbamate, carboxamide, phthalimide, sulfonamide, or the like. A typical embodiment of Z is 1-aminopropyl, or 1-aminoethyl, or aminomethyl, or 1-methylaminopropyl, or 1-methylaminoethyl, or methylaminomethyl, wherein the amine may be in a protected or unprotected form. Alternatively, Z can be a protected or unprotected 1-ethylaminomethyl or 1-ethylaminoethyl. Where Z has a chiral center adjacent to the carbonyl to which it is connected, the chiral center may have either the (R) or the (S) configuration. For specific embodiments, it is sometimes preferably in the (S) absolute configuration.

In compounds of formula (5), each of V and V' independently represents O or S, and each of J, J', m, m', Q, Q', $R^1$, $R^{1'}$, W, W', X, X', Y, Y', Z and Z' are as defined herein for compounds of formula (1). In preferred embodiments, J and J' are H; $R^1$ and $R^{1'}$ are H or methyl; and m and m' are 0 or 1. For compounds of formula (5), L represents a linker as already described for compounds of formula (1)-(3). In preferred embodiments, L is a C3-C8 alkynylene linker, a C5-C12 arylene linker or C5-C20 arylalkylene linker.

Each of W, W', X and X' in compounds of formula (5) may be independently selected, so they can be the same or different; in some embodiments, each of —W—X and —W'—X' are the same. In certain embodiments, each W and W' can be represented by a group of the form —C(O)NR—(CHR)$_p$—, where p is 0, 1 or 2 and each R is H or a C1-C4 alkyl group. In specific embodiments, W and W' are —C(O)NR—, where R is H or methyl.

In certain embodiments of formula (5), X and/or X' comprises an optionally substituted 5-membered heteroaryl ring containing 1-4 heteroatoms selected from N, O and S. In specific embodiments, X comprises an optionally substituted thienyl, furanyl, pyrrolyl, pyrazolyl, thiazolyl, isothiazolyl, oxazolyl, isoxazolyl, imidazolyl, triazolyl, thiadiazolyl, oxadiazolyl, or tetrazolyl ring. Optional substituents for X or X' in compounds of formula (5) include those described herein as preferred substituents when present on an aryl or heteroaryl ring that is part of X or X'. In preferred embodiments, X comprises a 5-membered heteroaryl ring as described above, optionally substituted with at least one C5-C12 aryl or C5-C12 heteroaryl group. In more preferred embodiments, X comprises a 5-membered heteroaryl ring substituted with at least one phenyl or naphthyl ring, which phenyl or naphthyl ring may itself be further substituted by one or more substituents selected from halo, $NO_2$, $CF_3$, CN, COOR, $CONR_2$, OR and SR, where R is H, C1-C4 alkyl or C1-C4 heteroalkyl.

In other embodiments of formula (5), W can be a bond where X comprises an optionally substituted C5-C6 aryl or heteroaryl ring, and/or W' can be a bond where X' comprises an optionally substituted C5-C6 aryl or heteroaryl ring. In specific embodiments, W and/or W' is a bond where X and/or X' comprises an optionally substituted thiazole ring. In preferred embodiments, the thiazole ring is substituted by at least one optionally substituted C5-C12 aryl ring or C5-C20 arylalkyl substituent, or a heteroform of one of these. In particularly preferred embodiments, the thiazole ring is substituted by at least one phenyl, naphthyl, benzofuranyl, benzothienyl, benzisoxazolyl, quinolinyl, isoquinolinyl, thienyl, isoxazolyl ring, each of which may be further substituted; or is substituted by a diphenylmethyl, benzyl, phenethyl or dimethylbenzyl group.

In other embodiments of formula (5), each of W and W' is —C(O)NR—(CHR)$_p$—, where p is 0, 1 or 2, and each R is independently H or a C1-C4 alkyl group, as already described, and X and X' are independently a phenyl ring, or two phenyl rings, or a tetrahydronaphthyl or indanyl ring system, each of which may be optionally substituted, as described for compounds of formula (1).

For compounds of formulas (6), each of L, m, Q, V, W, X, Y, and Z is as defined for compounds of formula (5).

For compounds of formula (7), each of J, m, $R^1$, V, W, X, Y, Z are as defined for compounds of formula (5). U in formula (7) is as defined for compounds of formula (4). In preferred embodiments, U is a C2-C8 alkynyl, C2-C8 heteroalkynyl, C2-C8 alkenyl, C2-C8 heteroalkenyl, optionally substituted C5-C12 aryl, or optionally substituted C5-C20 arylalkyl group.

For compounds of formula (8), each of L, m, m', n, n', Q, Q', $R^1$, $R^{1'}$, V', W, W', X, X', Y, Y' Z and Z' is as defined for compounds of formula (1)-(2) or (5)-(6).

For compounds of formula (9), each of J, J', L, Q, Q', $R^1$, $R^{1'}$, W, W', X, X', Z and Z' is as defined for compounds of formula (1)-(2) or (5)-(6). Each of $R^6$ and $R^{6'}$ is independently H, C1-C4 alkyl, or C1-C4 heteroalkyl. In preferred embodiments, $R^6$ and $R^{6'}$ are the same, and each of $R^6$ and $R^{6'}$ is H or methyl. In some embodiments of formula (9), —W—X and —W'—X' represents a group of the formula —N($R^5$)C(O)—Ar or —N($R^5$)C(S)—Ar, where $R^5$ is H or C1-C4 alkyl, and Ar represents an optionally substituted C5-C12 aryl or C5-C12 heteroaryl group. For example, Ar can be a phenyl, biphenyl, naphthyl, pyridyl, indolyl, indoline, indazolyl, benzofuranyl, benzothienyl, benzimidazole, benztriazole, benzoxadiazole, or quinolinyl ring, or the like.

In other embodiments, W and/or W' represents a C2-C6 alkylene or heteroalkylene group, preferably substituted with a carbonyl oxygen (=O). In certain embodiments, W and/or W' is a C2-C6 heteroalkylene of the formula —N($R^5$)C(O)(C$R^7_2$)$_p$—, where p is 0, 1 or 2 and each $R^5$ and $R^7$ is independently H or C1-C4 alkyl. In some such embodiments, X and/or X' comprises an optionally substituted phenyl ring; or two phenyl rings attached to the same atom of W or W', where either phenyl group can be further substituted. In further embodiments, W and/or W' is a C2-C6 heteroalkylene represented as —N($R^5$)C(O)N($R^7$)—, where each of $R^5$ and $R^7$ is independently H or C1-C4 alkyl; in specific embodiments, each of $R^5$ and $R^7$ is H or methyl, and X and/or X' comprises an optionally substituted phenyl ring or pyridyl ring.

For compounds of formula (10), each of J, $R^1$, $R^6$, W, X, Y, and Z is as defined for compounds of formula (9). U in formula (7) is as defined for compounds of formula (4). In preferred embodiments, U is a C2-C8 alkynyl, C2-C8 heteroalkynyl, C2-C8 alkenyl, C2-C8 heteroalkenyl, C1-C6 aminoalkyl, optionally substituted C5-C12 aryl, or optionally substituted C5-C20 arylalkyl group.

For compounds of formula (11), each of L, m, n, Q, Q', $R^1$, $R^{1'}$, W, W', X, X', Z and Z' is as defined for compounds of formulas (1)-(2) and (9), and $R^{6'}$ is as defined for compounds of formula (9).

For compounds of formula (12), each of L, Q, Q', $R^1$, $R^{1'}$, V, W, W', X, X', Y, Z and Z' is as defined for compounds of formulas (5)-(6) and (9), and $R^{6'}$ is as defined for compounds of formula (9).

For compounds of formula (13), each of =B and =B' independently represents =O, =S, $F_2$ or $H_2$, and each q and q' is independently 1-4. In compounds of formula (13), each of J, J', L, n, n', Q, Q', $R^1$, W, W', X, X', Z and Z' is as defined for compounds of formulas (1)-(2) and (5)-(6). In preferred embodiments, n and n' are 1; each q and q' is 1 or 2 or 3; J and J' are H; and each $R^1$ and $R^{1'}$ is H or methyl. In certain embodiments, W and/or W' is a C2-C6 alkylene group, where X and/or X' is an optionally substituted phenyl ring or two phenyl rings attached to the same atom of W or W'; in other embodiments, W and/or W' is a bond, and X is a tetrahydronaphthyl or indanyl ring system. In preferred embodiments, —W—X and/or —W—X' represent a phenethyl group.

For compounds of formula (14), each of J, L, n, Q, $R^1$, W, X and Z are as defined in compounds of formulas (1)-(2), (5)-(6) and (13). Each of =B and q are as defined for compounds of formula (13), and U is as defined for compounds of formula (4).

For compounds of formula (15), each of B', L, m, n, n', q', Q, Q', $R^1$, W, W', X, X', Y, Z and Z' are as described for compounds of formulas (1)-(2), (5)-(6) and (13).

For compounds of formula (16), each of B', L, m, n', q', Q, Q', $R^1$, $R^{1'}$, V, W, W', X, X', Y, Z and Z' are as described for compounds of formulas (1)-(2), (5)-(6) and (13).

For compounds of formula (17), each of B', L, n', q', Q, Q', $R^1$, $R^{1'}$, W, W', X, X', Y, Z and Z' are as described for compounds of formulas (1)-(2), (9) and (13), and $R^6$ is as defined for compounds of formula (9).

The compounds of the invention typically contain one or more chiral centers. The invention expressly includes each diastereomer, as well as each enantiomer of each diastereomer of the compounds described and mixtures thereof, particularly racemic mixtures of single diastereomers such as the ones described, and highly enriched enantiomers having an enantiomeric excess (e.e.) of greater than 90% or greater than about 95%. Substituent groups may also include one or more chiral centers, and each enantiomer and diastereomer of these substituents as well as mixtures thereof are all included within the scope of the invention. Similarly, where double bonds are present, the compounds can exist in some cases as either cis or trans isomers; the invention includes each isomer individually as well as mixtures of isomers.

Merely as examples of selected compounds of the invention, Table 2 illustrates a number of compounds of formula (1). These represent selected preferred species, and other species that include combinations of the features in the compounds specifically depicted are also preferred.

The compounds of the invention may be isolated as salts where an ionizable group such as a basic amine or a carboxylic acid is present. The invention includes the salts of these compounds that have pharmaceutically acceptable counterions. Such salts are well known in the art, and include, for example, salts of acidic groups formed by reaction with organic or inorganic bases, and salts of basic groups formed by reaction with organic or inorganic acids, as long as the counterions introduced by the reaction are acceptable for pharmaceutical uses. Examples of inorganic bases with alkali metal hydroxides (e.g., sodium hydroxide, potassium hydroxide, etc.), alkaline earth metal hydroxides (e.g., of calcium, magnesium, etc.), and hydroxides of aluminum, ammonium, etc.

Examples of organic bases that could be used include trimethylamine, triethylamine, pyridine, picoline, ethanolamine, diethanolamine, triethanolamine, dicyclohexylamine, N,N'-dibenzylethylenediamine, etc. Examples of inorganic acids that could be used include hydrochloric acid, hydrobromic acid, nitric acid, sulfuric acid, phosphoric acid, etc. Examples of organic acids include formic acid, oxalic acid, acetic acid, tartaric acid, methanesulfonic acid, benzenesulfonic acid, malic acid, methanesulfonic acid, benzenesulfonic acid, p-toluenesulfonic acid, etc. Also included are salts with basic amino acids such as arginine, lysine, ornithine, etc., and salts with acidic amino acids such as aspartic acid, glutamic acid, etc.

The compounds of the invention can be used to prepare pharmaceutical compositions containing at least one compound of any of formulas (1)-(3), (5)-(6), (8)-(9), (11)-(13) and (15)-(17), and at least one pharmaceutically acceptable excipient. Such compositions can be optimized for various conditions and routes of administration using guidance that is widely relied on for such purposes including Remington's *Pharmaceutical Sciences*, latest edition, Mack Publishing Co., Easton, Pa., which is incorporated herein by reference. The compositions comprise a compound of the invention admixed with at least one pharmaceutically acceptable excipient, and preferably with at least one such excipient other than water or a solvent such as DMSO.

The compounds of the invention are suitable to treat a wide variety of cancers. In particular, they are suitable to treat neuroblastoma, glioblastoma, breast carcinoma, melanoma, prostate carcinoma, pancreatic carcinoma, hepatocellular carcinoma, colon carcinoma, and small-cell and non-small cell lung carcinoma.

The compounds of the invention are also suitable to treat various autoimmune disorders, particularly rheumatoid arthritis, lupus, vasculitis, glomerulonephritis, type-I diabetes, pernicious anemia, myasthenia gravis, Guillain-Barre syndrome, and infections with autoimmune effects such as AIDS, malaria, Chagas disease, and Lyme disease.

The compounds of the invention are not on their own very cytotoxic: they depend for their activity on potentiation of the effects of other effectors, which may be natural, endogenous substances, or they may be additional therapeutic substances. For example, Smac mimics have been shown to strongly potentiate the activity of TRAIL or etoposide when co-administered. Accordingly, the compounds of the invention may be used in conjunction with or in combination with an additional therapeutic having anticancer effects. Such additional therapeutic can be a drug, or it can be a radiation treatment. Where an additional drug is administered, it is typically one known to have cytostatic, cytotoxic or antineoplastic activity. These agents include, for example, antimetabolites such as cytarabine, fludaragine, 5-fluoro-2'-deoxyuridine, gemcitabine, hydroxyurea, methotrexate; DNA active agents such as bleomycin, chlorambucil, cisplatin, cyclophosphamide, intercalating agents such as adriamycin and mitoxantrone; protein synthesis inhibitors such as L-asparaginase, cycloheximide, puromycin; topoisomerase I inhibitors such as camptothecin or topotecan; topoisomerase II inhibitors such as etoposide and teniposide; microtubule inhibitors such as colcemid, colchicines, paclitaxel, vinblastine and vincristine; and kinase inhibitors such as flavopiridol, staurosporin, and hydroxystaurosporine. Preferred additional drugs for co-administration with the compounds of the invention include those that affect Hsp90 (heat-shock protein 90). Suitable Hsp90 inhibitors include ansamycin derivatives such as geldanomycin and geldanomycin derivatives including 17-(allylamino)-17-desmethoxygeldanamycin (17-AAG), its dihydro derivative, 17-AAGH$_2$, and 17-amino derivatives of geldanamycin such as 17-dimethylaminoethylamino-17-demethoxy-geldanamycin (17-DMAG), 11-oxogeldanamycin, and 5,6-dihydrogeldanamycin, which are disclosed in U.S. Pat. Nos. 4,261,989; 5,387,584; and 5,932,566, each of which is incorporated herein by reference. Other suitable Hsp90 inhibitors include radicicol and oximes and other analogs thereof, disclosed in Soga, et al., *Curr. Cancer Drug Targets*, 3, 359-69 (2003), and in Yamamoto, et al., *Angew. Chem.*, 42, 1280-84 (2003); and in Moulin, et al., *J. Amer.*

*Chem. Soc.*, vol 127, 6999-7004 (2005); purine derivatives such as PU3, PU24FCI and PUH64 (see Chiosis et al., *ACS Chem. Biol.* Vol. 1(5), 279-284 (2006) and those disclosed in PCT Application No. WO 2002/0236075; related heterocyclic derivatives disclosed in PCT Application No. WO 2005/028434; and 3,4-diarylpyrazole compounds disclosed in Cheung, et al., *Bioorg. Med. Chem. Lett.*, vol. 15, 3338-43 (2005). Antibodies or antibody fragments that selectively bind to Hsp90 may also be administered as drugs to cause inhibition of Hsp90, and can be used in combination with the compounds of the invention.

Natural effectors such as TRAIL, a TRAIL receptor antibody, and TNF-α and TNF-β can also be administered as drugs for this purpose, and are also preferred, as are active fragments of these peptides.

Where a compound of the invention is utilized to potentiate the effects of another therapeutic, the two agents may be co-administered, or they may be administered separately where their administration is timed so the two agents act concurrently or sequentially. Accordingly, the compositions of the invention include at least one compound of formula (I), (1)-(3), (5)-(6), (8)-(9), (11)-(14) or (15)-(17), and can optionally include one or more additional cytotoxic or cytostatic therapeutic such as, but not limited to, those disclosed above. Similarly, the methods of the invention include methods wherein a subject diagnosed as in need of treatment for inflammation and/or cancer is treated with at least one compound or composition of the invention, and is simultaneously or concurrently treated with one or more of the additional therapeutic agents described above, particularly TRAIL, a TRAIL receptor antibody, TNF-α or TNF-β.

Formulations of the compounds and compositions of the invention may be prepared in a manner suitable for systemic administration or topical or local administration. Systemic formulations include those designed for injection (e.g., intramuscular, intravenous or subcutaneous injection) and those prepared for transdermal, transmucosal, or oral administration. The formulation will generally include a diluent as well as, in some cases, adjuvants, buffers, preservatives and the like. The compounds can be administered also in liposomal compositions or as microemulsions.

Injection methods are sometimes appropriate routes for administration of the compounds for systemic treatments and sometimes also for localized treatments. These include methods for intravenous, intramuscular, subcutaneous, and other methods for internal delivery that bypass the mucosal and dermal barriers to deliver the composition directly into the subject's living tissues.

For injection, formulations can be prepared in conventional forms as liquid solutions or suspensions or as solid forms suitable for solution or suspension in liquid prior to injection or as emulsions. Suitable excipients include, for example, water, saline, dextrose, glycerol and the like. Such compositions may also contain amounts of nontoxic auxiliary substances such as wetting or emulsifying agents, pH buffering agents and the like, such as, for example, sodium acetate, sorbitan monolaurate, and so forth.

Various sustained release systems for drugs have also been devised and can be utilized with the compounds of the invention. See, for example, U.S. Pat. No. 5,624,677. The present compositions can be utilized in such controlled-release delivery systems where appropriate.

Systemic administration may also include relatively non-invasive methods such as the use of suppositories, transdermal patches, transmucosal delivery and intranasal administration. Oral administration is also suitable for compounds of the invention, which are more robust than the Smac peptide itself and are thus advantageously more orally bioavailable. Suitable forms include syrups, capsules, tablets, and the like as in understood in the art.

Selection of a particular route of administration for a given subject and indication is well within the ordinary level of skill in the art. For example, rectal delivery as a suppository is often appropriate where the subject experiences nausea and vomiting that precludes effective oral delivery. Transdermal patches are commonly capable of delivering a controlled-release dosage over several days or to a specific locus, and are thus suitable for subjects where these effects are desired.

Transmucosal delivery is also appropriate for some of the compositions and methods of the invention. Thus the compositions of the invention may be administered transmucosally using technology and formulation methods that are known in the art.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

For administration to animal or human subjects, the dosage of a compound of the invention is typically 10-2400 mg per administration. However, dosage levels are highly dependent on the nature of the condition, the condition of the patient, the judgment of the practitioner, and the frequency and mode of administration. Selection of a dosage of such compounds is within the skill of an ordinary artisan, and may be accomplished by starting at a relatively low dosage and increasing the dosage until an acceptable effect is achieved.

Frequency of administration of the compounds of the invention can also be readily determined by one skilled in the art using well known techniques. For example, the patient may be administered a low dosage of a compound or composition of the invention at a low frequency such as once per day or less often; and the dosage and/or frequency of administration may be systematically increased until a desired effect is achieved in the patient.

The compounds of the invention can be prepared by combining methods known in the art for preparing related compounds. For example, published patent applications US 2006/0025347, US 2005/0197403, WO 2006/069063, US 2006/0014700, WO 2005/094818, and WO 2005/097791, each of which is incorporated herein by reference in its entirety, each disclose methods for making monomeric precursors for the compounds of the invention. Many suitable monomers are readily prepared by known methods, including the extensive body of literature describing synthesis of peptides and peptide mimetics. Examples of the synthesis of certain monomers are included herein. Representative monomers are shown in Table 3. Preparation of the compounds of the invention from such precursors can be achieved using methods known in the art. Accordingly, synthesis of these compounds is within the ordinary skill in the art. Synthetic methods for making selected compounds of the invention are also provided herein.

A preferred method for making the compounds of formula (1) involves dimerization of monomers of formula (4). Thus, the invention includes monomers of formula (4) and methods of using such monomers to make compounds of formulas (1)-(3). For example, compounds of formula (1) that are symmetric and have a diacetylenic group for the linker L can be made, as described by Harran, et al., US 2005/0197403, by dimerizing two acetylenic monomers in the presence of a copper salt. This reaction is illustrated in Scheme 1, using a fluorenyloxymethyl carbonyl (Fmoc) protecting group on nitrogen, which is removed with piperidine after the copper-mediated coupling reaction is completed. The following examples illustrate the use of a different protecting group; any suitable protecting group may be used as is understood in the art. This method enables the preparation of compounds such as the acetylenic compounds shown in Table 2 (compounds no. 1, 3, 5, 7, 9, 13, 15, and 16).

be incorporated into a monomer of formula (4), which can undergo cycloaddition with an acetylene containing monomer to form a dimer containing a triazole ring as part of the linker, or two azide containing monomers could react with a bis-acetylene moiety to form a dimer having two triazole rings as part of the linker.

A wide variety of methods for forming such dimeric compounds are known in the art, and may be employed with suitably functionalized monomers. For example, hydroxyl substituted aryl or arylalkyl groups may be modified to form aryl triflates or other suitable functional groups, which may undergo cross-coupling reactions, for example with alkynes, to form dimeric structures such as, e.g., compounds no. 25, 26, 28, 32, 35, 36, 37, 39, and 40. One of skill in the art would recognize that such compounds may undergo further chemical transformations, for example, partial or complete hydrogenation to form alkenyl or saturated linkers, such as, e.g., compounds no. 28, 30, 31, 33, 34, 38, and 41 in Table 2.

Additionally, hydroxyl substituted monomers may be alkylated, for example with allylic halides, to form other linkers or other functionalized monomers. Examples of such compounds are shown in Table 2, compounds no. 44 and 46; hydrogenation of compound no. 44 provides compound no. 45.

Scheme 1.

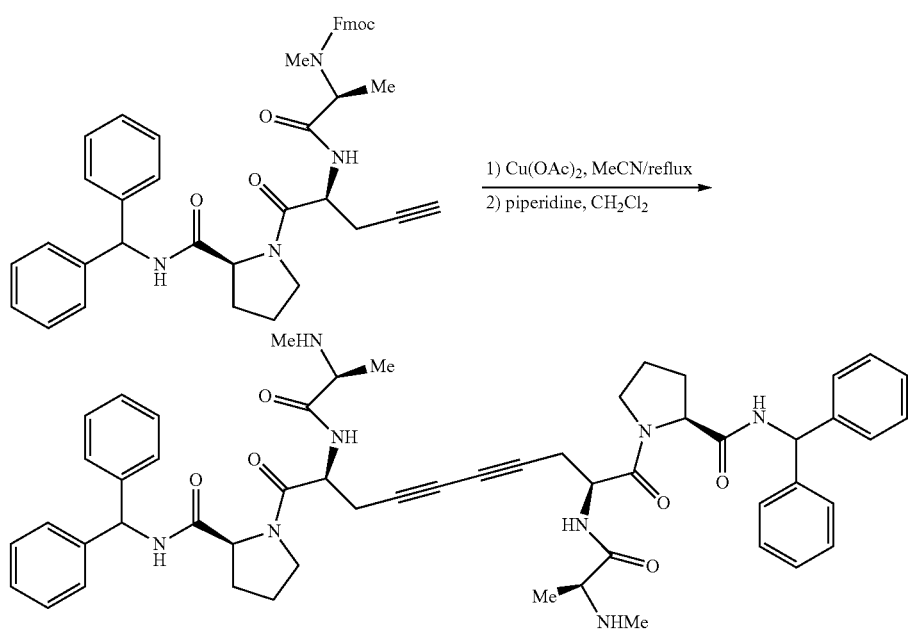

The acetylenic linking groups can be readily modified to produce other linkers; for example, catalytic hydrogenation of such bis-acetylenic compounds would provide the partially or fully saturated-linker compounds in Table 2 (compounds no. 2, 4, 6, 8, 10, 11, 12, and 14).

The acetylenic linking groups may also undergo cycloaddition reactions. For example, cycloaddition reactions of a bis-acetylenic dimer of formula (1) with an alkyl bis-azide provides fused triazoles such as compounds no. 18, 19, 21, and 23.

In addition, two alkynyl monomers of formula (4) may undergo dimerization concomitantly with cycloaddition with an alkyl bis-azide, to form triazole-containing linkers such as compounds no. 17, 20, 22 and 24. Alternatively, an azide may Alkylamine monomers may undergo dimerization by further reaction at the amine center, for example by N-alkylation, acylation, or carbamoylation, or the like, to produce dimers such as, e.g., compounds no. 47, 48, 49, and 50 in Table 2. In addition, alkylamine monomers may undergo reaction to provide additional monomers containing functional groups suitable for dimerization, for example, by azidonation to provide azide containing monomers, or alkylation with propargyl halides to provide additional acetylene containing monomers.

The in vitro and in vivo activities of the compounds of the invention may be determined using techniques that are known in the art. For example, Bockbrader, et al., *Oncogene* vol. 24, 7381-88 (2005) discloses assays for determination of the effect of Smac mimics using cell culture assays and in vitro assays for caspase activation. Accordingly, in addition to guidance from symptomology, treatment with the compounds, compositions and methods of the invention can be monitored by methods known in the art for determining the effects of Smac mimetic compounds.

The following examples are provided to illustrate the invention and are not intended to represent or limit its scope. The Examples provide representative chemical syntheses, as well as assays for determining the bioactivity of Smac mimetics, e.g. as measured by IAP binding, procaspase-3 activation or promotion of apoptosis. These assays may also be used to screen for agents (e.g. antagonists) which potentiate such mimetic activity.

Example 1

(S)—N—((R)-1,2,3,4-tetrahydronaphthalen-1-yl)pyrrolidine-2-carboxamide 2,2,2-trifluoroacetate

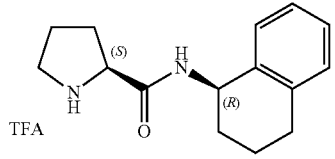

Boc-L-Pro-OH (41.7 g, 0.17 mol), R-tetrahydronapthylamine (31.8 g, 0.22 mol), and hydroxybenzotriazole (28.4 g, 0.18 mol) was dissolved in dimethylformamide (300 mL) and cooled to 0° C. To this cooled reaction mixture was added EDC (41.7 g, 0.22 mol) followed by DiPEA (30.1 mL, 0.17 mol). Reaction was allowed to slowly warm to room temperature and was stirred overnight. Reaction mixture was then partitioned between ethyl acetate and water. The aqueous layer was discarded and the organic layer was washed sequentially with sat. NaHCO₃, 0.5 N HCl, and brine. Dried over Na₂SO₄. Reaction was clean by TLC (50% ethyl acetate/hexanes). Took crude on to next step. Dissolved crude in CH₂Cl₂ (200 mL) and TFA (200 mL). Within 15 minutes, reaction was baseline by TLC (50% ethyl acetate/hexanes). Removed most of solvent via rotary evaporation. Upon addition of diethyl ether, a white solid crashes out. Filtered solid and washed with diethyl ether. Dried solid under vacuum. Obtained 63 g of desired compound (95% yield over 2 steps). ¹H NMR (CD₃OH): consistent with proposed structure.

Example 2 tert-butyl(S)-1-oxo-1-((S)-2-(R)-1,2,3,4-tetrahydronaphthalen-1-ylcarbamoyl)pyrrolidin-1-yl)pent-4-yn-2-ylcarbamate

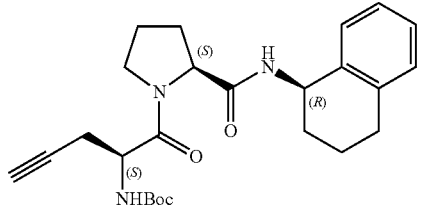

Boc-L-Propargylglycine-OH (700 mg, 3.28 mmol) was dissolved in DMF (13 mL) and cooled to 0° C. To this was added HOBt (608 mg, 3.94 mmol) and DiPEA (1.37 mL, 7.87 mmol). After 5 mins., EDC (755 mg, 3.94 mmol) was added. After another 5 mins., the title compound of Example 1 (1.23 g, 3.61 mmol) was added. The reaction mixture was then allowed to warm to room temperature and was stirred overnight. Reaction mixture was then partitioned between ethyl acetate and 0.5 N HCl. Aqueous layer was discarded. Organic layer was then washed sequentially with sat. NaHCO₃, water, and brine. Organic layer was then dried over Na₂SO₄. Upon rotary evaporation, a white solid crashed out of ethyl acetate. The white solid was filtered and rinsed with hexanes. Solid was dried under vacuum to afford 1.3 g of the title compound (90% yield). ¹H NMR (CD₃OH): consistent with proposed structure. MS (m/z): 439.3.

Example 3 tert-butyl methyl((S)-1-oxo-1-((S)-1-oxo-1-((S)-2-((R)-1,2,3,4-tetrahydronaphthalen-1-ylcarbamoyl)pyrrolidin-1-yl)pent-4-yn-2-ylamino)propan-2-yl)carbamate

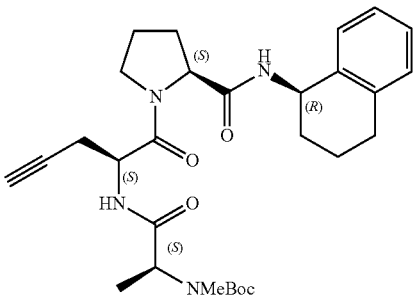

The title compound of Example 2 (1.3 g, 2.96 mmol) was dissolved in 4N HCl in dioxane (ca. 20 mL) at room temperature. The reaction was stirred for about 15 mins. By TLC (100% ethyl acetate) UV active spot was baseline. Excess 4N HCl in dioxane was removed by rotary evaporation and reduced pressure vacuum pump application. This residue was taken directly to the next step without further purification. Boc-NMe-Ala-OH (662 mg, 3.26 mmol) was dissolved in DMF (12 mL) and cooled to 0° C. To this was added HOBt (548 mg, 3.55 mmol) and DiPEA (1.55 mL, 8.88 mmol). After 5 mins., EDC (681 mg, 3.55 mmol) was added. After another 5 mins., sh-10-50 (1.3 g, 2.96 mmol) was added. The reaction mixture was then allowed to warm to room temperature and was stirred overnight. Reaction mixture was then partitioned between ethyl acetate and 0.5 N HCl. Aqueous layer was discarded. Organic layer was then washed sequentially with sat. NaHCO₃, water, and brine. Organic layer was then dried over Na₂SO₄. Crude oil was purified via flash column chromatography to afford 1.4 g of off-white solid (90% yield). By TLC (100% ethyl acetate) desired compound is not very UV active—used silica gel impregnated with iodine to visualize desired compound. ¹H NMR (CDCl₃): consistent with proposed structure.

Example 4

(S)-1-((S)-2-((S)-2-(methylamino)propanamido)pent-4-ynoyl)-N—((R)-1,2,3,4-tetrahydronaphthalen-1-yl)pyrrolidine-2-carboxamide hydrochloride

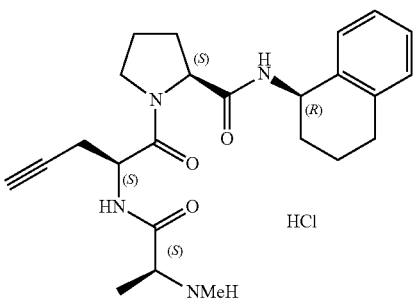

The title compound of Example 3 (33 mg) was dissolved in 4N HCl in dioxane (2 mL). This was stirred for approximately 15 mins. By TLC (100% ethyl acetate), UV spot was baseline. Excess 4N HCl in dioxane was removed via vacuum. For final compounds, material was left on vacuum pump overnight. For batch 2, material was dissolved in HPLC grade water, filtered through a 0.45 micron filter, and lyophilized overnight to give the title compound as a white semi-fluffy solid. $^1$H NMR (CD$_3$OH): consistent with proposed structure. MS (m/z): 424.3.

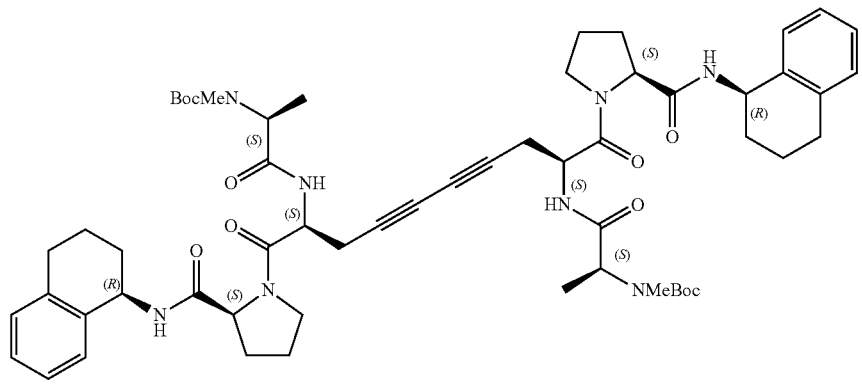

The title compound of Example 3 (600 mg, 1.14 mmol) and Cu(OAc)$_2$ (1.05 g, 5.76 mmol) were dissolved in CH$_3$CN (7.6 mL). This was refluxed for 20 mins. By TLC (10% MeOH/CH$_2$Cl$_2$), starting material was still present, so the mixture was refluxed for an additional 20 mins. By TLC, starting material had been consumed. Removed CH$_3$CN via rotary evaporation and vacuum pump. Residue was then partitioned between ethyl acetate and water. Aqueous phase was discarded and organic phase was washed with brine and dried over Na$_2$SO$_4$. Oily residue was purified via flash column chromatography (a gradient of 100% ethyl acetate to 5% MeOH/CH$_2$Cl$_2$ to 10% MeOH/CH$_2$Cl$_2$) to afford the title compound as a white solid. $^1$H NMR (CD$_3$OH): consistent with proposed structure. MS (m/z): 1047.3.

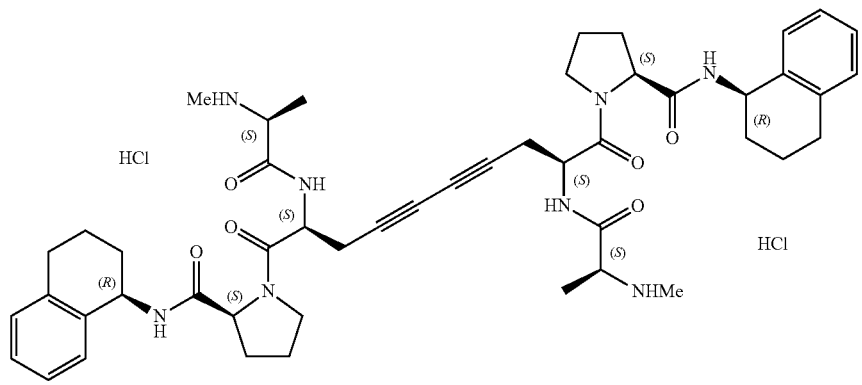

The compound of Example 5 (246 mg) was dissolved in 4N HCl in dioxane (10 mL) at room temperature. A precipitate crashed out right away. This was filtered and rinsed with Et$_2$O to give a pale yellow solid which was dried via vacuum pump overnight before submitting for biological testing. For other batches, the bis-hydrochloride salt was dissolved in HPLC grade water, filtered through a 45 micron filter, and lyophilized to give the title compounds as a fluffy light beige material. $^1$H NMR (CD$_3$OH): consistent with proposed structure. MS (m/z): 846.5.

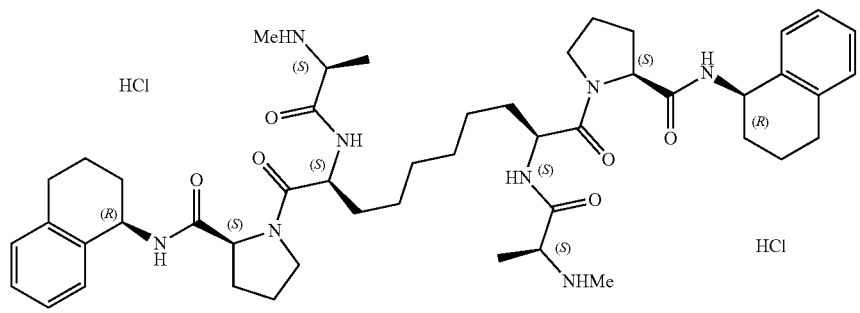

The compound of Example 6 (50 mg) was dissolved in MeOH (3 mL) at room temperature. The reaction flask was purged with nitrogen before adding 10% Pd/C to the reaction. A hydrogen balloon with a 3 way stopcock was then connected to the round bottom. Nitrogen gas was evacuated via vacuum and re-filled with hydrogen gas three times before allowing the reaction to stir under a hydrogen balloon atmosphere (1 atm) overnight. The reaction mixture is then filtered through a 45 micron filter, rinsed with MeOH, and concentrated in vacuo to give a white solid that was left on the vacuum pump overnight. For batch 2 of JP 1060, material was dissolved in HPLC grade water, filtered through 45 micron filter, and lyophilized to give a fluffy white material. $^1$H NMR (CD$_3$OH): consistent with proposed structure.

Example 8 allyl(2S,3R)-1-oxo-3-(prop-2-ynyloxy)-1-((S)-2-((R)-1,2,3,4-tetrahydronaphthalen-1-ylcarbamoyl)pyrrolidin-1-yl)butan-2-ylcarbamate

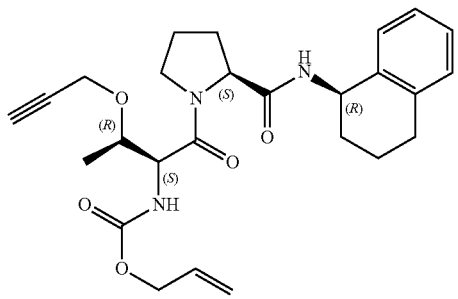

(2S,3R)-2-(allyloxycarbonylamino)-3-(prop-2-ynyloxy)butanoic acid (200 mg, 3.28 mmol) was dissolved in dimethylformamide (7.5 mL) and cooled to 0° C. To this was added the title compound of Example 1 (356 mg). Diisopropylethylamine (0.47 mL) was then added followed by HATU (378 mg). The reaction mixture was stirred for 3 hours. Reaction mixture was then partitioned between diethyl ether and saturated aqueous sodium bicarbonate solution. Organic layer was then washed sequentially with 1N HCl, water, and brine. Organic layer was then dried over Na$_2$SO$_4$, and evaporated at reduce pressure. A yellow oil was obtained which was chromatographed on silica gel, eluting with 1:1 ethyl acetate-hexanes. The title compound was obtained as a white foam (70% yield). $^1$H NMR (CDCl$_3$): consistent with proposed structure.

Example 9 tert-butyl methyl((S)-1-oxo-1-((2S,3R)-1-oxo-3-(prop-2-ynyloxy)-1-((S)-2-((R)-1,2,3,4-tetrahydronaphthalen-1-ylcarbamoyl)pyrrolidin-1-yl)butan-2-ylamino)propan-2-yl)carbamate

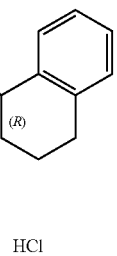

Boc-N-Me-Ala-OH (3.5 grams) was dissolved in methylene chloride (77 mL) and to this was added 1-hydroxybenzotriazole (2.34 grams). Cooled to 0 and added EDC (3.32 grams) in two portions over 5 minutes. The mixture was stirred for 1 hour, then warmed to room temperature and stirred for an additional hour. To this solution was added palladium tetrakis(triphenylphosphine) (0.67 grams). The title compound of Example 8 (2.7 grams) was then added as a solution in methylene chloride (29 mL), followed by DABCO (9.72 grams). The reaction was stirred for 15 minutes, then concentrated under reduced pressure to an orange syrup. This crude material was purified via flash column chromatography, eluting with 1:1 ethyl acetate-hexanes to afford a white foam (3.3 grams, 100% yield). $^1$H NMR (CDCl$_3$): consistent with proposed structure.

Example 10 tert-butyl(S)-1-(4-hydroxyphenyl)-2-oxo-2-((S)-2-((R)-1,2,3,4-tetrahydronaphthalen-1-ylcarbamoyl)pyrrolidin-1-yl)ethylcarbamate

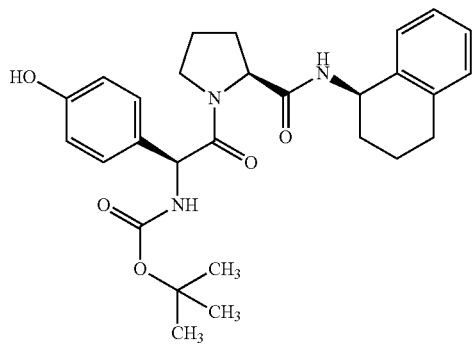 [SMILES: CC(C)(C)OC(=O)N[C@H](C(=O)N1CCC[C@H]1C(=O)N[C@@H]1CCCc2ccccc21)c1ccc(O)cc1]

Boc-p-hydroxyphenylglycine was coupled to the title amine of Example 1, using the same procedure that was used to prepare the title compound of Example 1. $^1$H NMR (CDCl$_3$): consistent with proposed structure.

Example 11 tert-butyl(S)-1-(S)-1-(4-hydroxyphenyl)-2-oxo-2-((S)-2-((R)-1,2,3,4-tetrahydronaphthalen-1-ylcarbamoyl)pyrrolidin-1-yl)ethylamino)-1-oxopropan-2-yl(methyl)carbamate

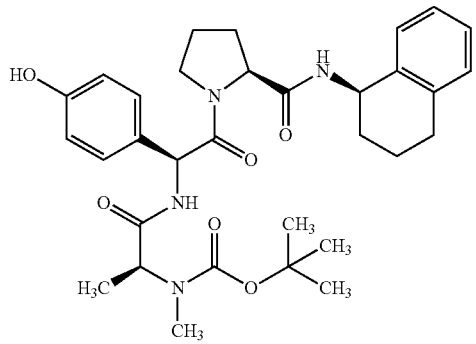 [SMILES: C[C@@H](C(=O)N[C@H](C(=O)N1CCC[C@H]1C(=O)N[C@@H]1CCCc2ccccc21)c1ccc(O)cc1)N(C)C(=O)OC(C)(C)C]

The title compound of Example 10 was treated with 4N HCl-dioxane and the solvent was removed under reduced pressure. The resulting hydrochloride was coupled to Boc-N-Me-Ala-OH using the same procedure as was used to prepare the title compound of Example 1. The crude product was chromatographed on silica gel, eluting with 1:1 ethyl acetate-hexanes to give the pure title compound as a white solid. $^1$H NMR (CD$_3$OH): consistent with proposed structure.

Example 12

4-((S)-1-((S)-2-(tert-butoxycarbonyl(methyl)amino)propanamido)-2-oxo-2-((S)-2-((R)-1,2,3,4-tetrahydronaphthalen-1-ylcarbamoyl)pyrrolidin-1-yl)ethyl)phenyl trifluoromethanesulfonate

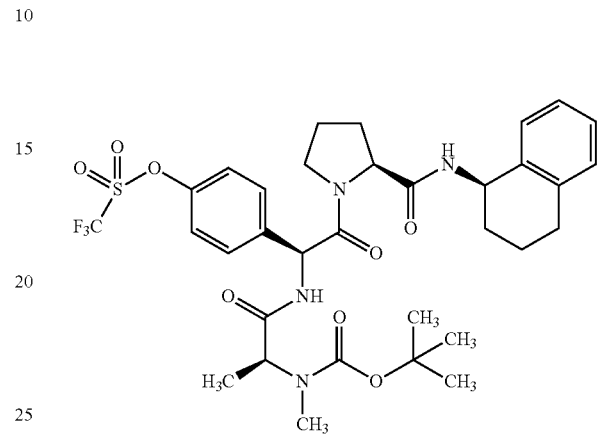

The title compound of Example 11 (830 mg, 1.4 mmol) was dissolved in methylene chloride (5 mL) at 0. To this was added pyridine (350 microliters), followed by triflic anhydride (350 microliters, 2.1 mmol, d=1.7). After 15 minutes the dark yellow solution was poured into saturated sodium bicarbonate solution and extracted with ether. The organic phase was washed with 1N HCl, saturated sodium bicarbonate, water, dried over sodium sulfate and evaporated to dryness under reduced pressure. The residue was chromatographed on silica gel, eluting with 1:1 ethyl acetate-hexanes to give the title compound as a yellow foam. NMR (CDCl$_3$): consistent with proposed structure.

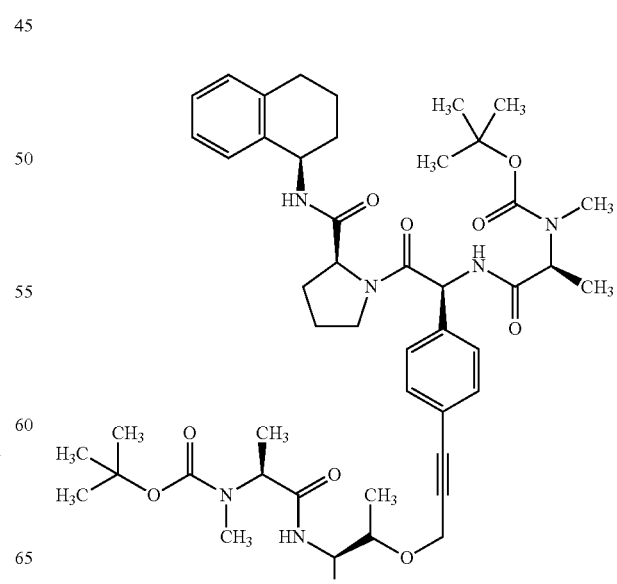

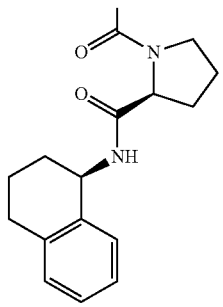

The title compound of Example 12 ("triflate", 85 mg, 0.197 mmol), was mixed with the title compound of Example 9 ("acetylene", 72 mg, 0.126 mmol), triethylamine (80 uL, 0.8 mmol), tetrakis(triphenylphosphine)palladium(0) (15 mg, 0.013 mmol), and CuI (5 mg, 0.026 mmol) in dimethylformamide (5 mL). This mixture was stirred at room temperature for 2 hours, then 85° C. for 3.5 hours, then room temperature for 16 hours. The solvent was evaporated and the residue chromatographed on silica gel to yield the title compound. NMR (CDCl$_3$): consistent with proposed structure.

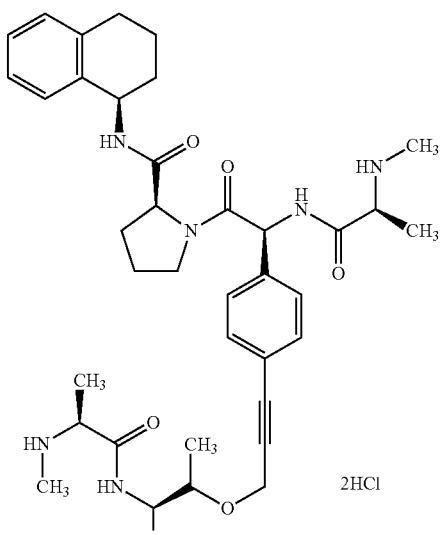

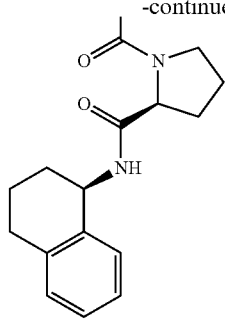

The title compound of Example 13 was dissolved in 4N HCl dioxane and the solution was allowed to stand at room temperature for 20 minutes. The solvent was evaporated and the residue taken up in minimum amount of methanol. Diethyl ether was added and the mixture was stirred for 20 minutes. The resulting precipitate was collected to yield the title compound as a powder (55 mg). Mass spectrum (ESI): m/z=929 (M+1).

Example 15 tert-butyl(S)-3-(4-hydroxyphenyl)-1-oxo-1-((S)-2-((R)-1,2,3,4-tetrahydronaphthalen-1-ylcarbamoyl)pyrrolidin-1-yl)propan-2-ylcarbamate

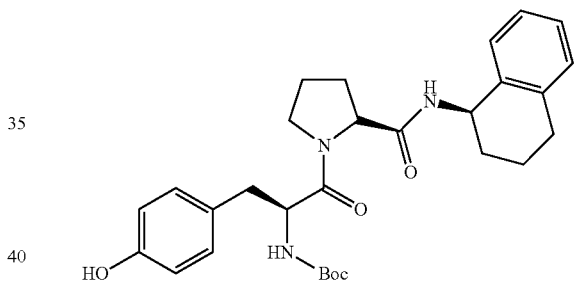

Boc-L-tyrosine (7.00 g, 0.025 mol, 1.00 equiv), the title compound of Example 1 (10.26 g, 0.029 mol, 1.15 equiv), HOBt (4.04 g, 0.030 mol, 1.20 equiv), and EDCI (5.79 g, 0.030 mol, 1.20 equiv) were combined together at room temperature, and the system was quickly cycled with vacuum/N$_2$(g) 2×'s, leaving under N$_2$(g). The reaction solution was then placed on ice water bath and allowed to stir for 10 minutes, after which DIPEA (12.34 mL, 0.075 mol, 3.00 equiv, 0.782 g/mL) was charged dropwise over 5 minutes. The solution was allowed to stir while warming to room temperature from an ice-water bath overnight. The resulting solution was diluted with EtOAc and poured onto ice in a separatory funnel. An extraction was performed, and the aqueous layer was back extracted with EtOAc three times. The organic layers were combined and washed with 1.0N HCl in H$_2$O then with sat'd NaHCO$_3$. The aqueous layer was acidified to pH ~7 and extracted with EtOAc three times. The organic layers were combined and washed with brine. The resulting solution was dried over MgSO$_4$, filtered, and concentrated to yield a yellow oil. The oil was dried via high vacuum over the weekend to give a white solid. This solid was recrystallized from EtOH/Hexanes to give 9.49 g of the title compound in 75.1% isolated yield. The product was 100% pure by LC-MS and TLC. TLC Conditions: 100% EtOAc, Iodine Stain. Product Rf=0.74.

Example 16

(S)-1-((S)-2-amino-3-(4-hydroxyphenyl)propanoyl)-N—((R)-1,2,3,4-tetrahydronaphthalen-1-yl)pyrrolidine-2-carboxamide hydrochloride

Example 17 tert-butyl(S)-1-((S)-3-(4-hydroxyphenyl)-1-oxo-1-((S)-2-((R)-1,2,3,4-tetrahydronaphthalen-1-ylcarbamoyl)pyrrolidin-1-yl)propan-2-ylamino)-1-oxo-propan-2-yl(methyl)carbamate

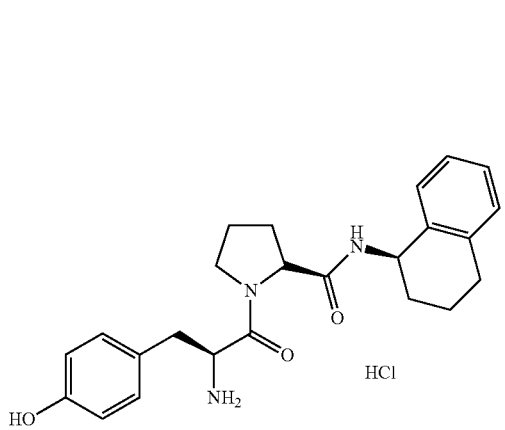

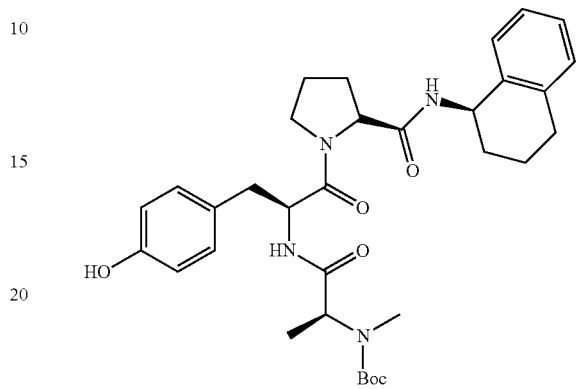

The title compound of Example 15 (9.49 g, 0.0.19 mol, 1.00 equiv) was dissolved in 1,4-dioxane (16.0 mL). At room temperature, 4.0N HCl in dioxane solution (60.0 mL) was charged, and the reaction solution was allowed to stir open to the air for 30 minutes (virtually clear solution). The reaction was confirmed to be complete via TLC (100% EtOAc, Iodine Stain, Rf 5=0.0). All solvents were concentrated off to give white solids. These solids were taken up in $CH_2Cl_2$ and concentrated down to white solids again. The resulting solids were rinsed with MTBE, and the MTBE was decanted. This solid was dried via vacuum pump for 30 minutes to yield the title compound.

The title compound of Example 16 (8.30 g, 0.019 mol, 1.00 equiv), Boc-NMe-L-alanine (4.37 g, 0.021 mol, 1.15 equiv), HOBt (3.04 g, 0.022 mol, 1.20 equiv), and EDCI (4.30 g, 0.022 mol, 1.20 equiv) were combined together at room temperature, and the system was quickly cycled with vacuum/$N_2$(g) twice to provide an inert atmosphere, and was left under $N_2$(g). The reaction solution was then placed in an ice-water bath and allowed to stir for 15 minutes, after which DIPEA (9.58 mL, 0.058 mol, 3.00 equiv, 0.782 g/mL) was charged dropwise over 5 minutes. The solution was allowed to stir to room temperature in an ice-water bath overnight. The resulting solution was diluted with EtOAc and poured onto ice in a separatory funnel. An extraction was performed, and the aqueous layer was back extracted with EtOAc three times. The organic layers were combined and washed with 1.0N HCl in $H_2O$, sat'd $NaHCO_3$, and then brine. The resulting solution was dried over $MgSO_4$, filtered, and concentrated to yield a yellow oil. The crude product was purified via column (50-50 Hex-EtOAc to 100% EtOAc gradient) to give a light yellow oil. This oil was taken up in $CH_2CL_2$, concentrated, and then dried via high vacuum to yield 11.07 g of the title compound as a easily breakable foamy white solid in 99.9% yield. Purity was confirmed by LC-MS and TLC. TLC Conditions: 100% EtOAc, Iodine Stain. Product Rf=0.63.

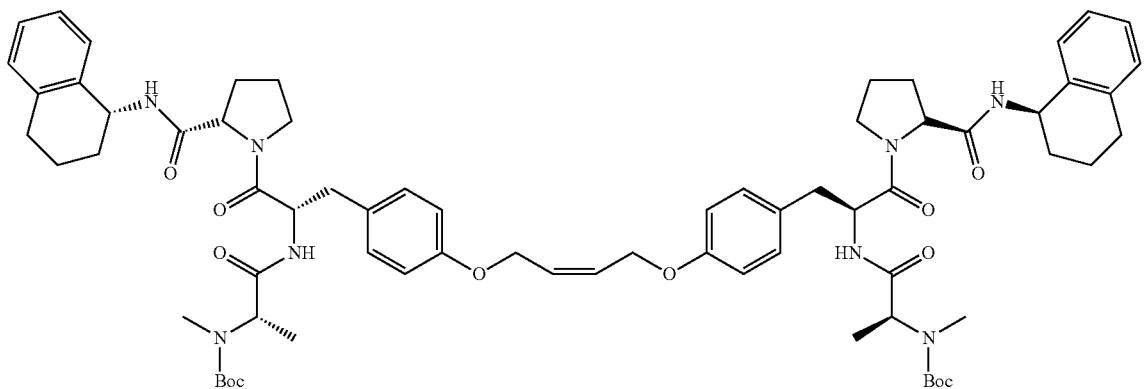

In an oven dried 25 ml round bottom flask, the title compound of Example 17 (200 mg, 0.335 mmol, 1.0 equiv.) was dissolved in DMF under N₂ at room temperature. To this solution was added K₂CO₃ (139 mg, 1.00 mmol, 3.0 equiv.) followed by cis-1,4-Dichloro-2-butene (17 µl, 0.167 mmol, 0.5 equiv.). A color change from colorless to light orange was observed upon addition of cis-1,4-Dichloro-2-butene. The resulting solution was stirred for 72 hours. Water (30 ml) was added to the reaction mixture and the resulting solution was extracted with EtOAc (three 30 ml aliquots). The combined organic extract was washed with brine (two 50 ml aliquots) and dried with Na₂SO₄. The resulting solution was evaporated to produce a white solid which was purified on silica with a gradient of 50/50 Hexanes/EtOAc to 100% EtOAc. Fractions containing purified product were pooled and evaporated to produce a white solid which was dried on high vacuum to yield 158 mg of the title compound as a white solid in 76% isolated yield. TLC Conditions: 100% EtOAc. Product Rf=0.20.

In a 25 ml round bottom flask, the title compound of Example 19 (70 mg, 0.063 mmol, 1.0 equiv.) was slurried with 10% palladium on carbon (35 mg) in methanol (10 ml). The resulting mixture was charged with H₂ and allowed to stir overnight at room temperature. The reaction mixture was filtered through a syringe filter and evaporated to a white solid which was dried on high vacuum to yield 65 mg of the title compound in quantitative yield.

The compounds of Examples 6, 7, 14, 19 and 20 will mimic the activity of Smac, and are thus useful in the treatment of disorders that can be treated with Smac or a Smac mimetic, such as those disorders discussed herein.

Example 21

In Vitro IAP (BIR) Binding/Interaction Assay

Interaction between mimetics and IAPs was examined by GST-mediated pull-down assays. Approximately 0.4 mg of a

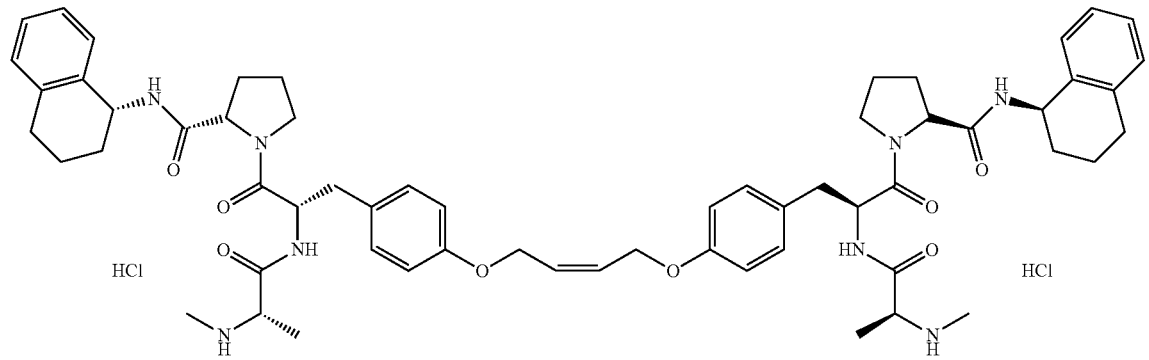

In a 25 ml round bottom flask, the title compound of Example 18 (158 mg, 0.128 mmol, 1.0 equiv.) was dissolved in 4.0 ml 4.0 N HCl in dioxane. The resulting solution was stirred at room temperature for 30 minutes. The reaction mixture was evaporated to an oil, which was dried on high vacuum to yield 148 mg of the title compound in quantitative yield as a white solid.

The 'trans' isomer of this compound is readily prepared by the method described above, by using trans-1,4-dichloro-2-butene instead of the cis isomer in the step described in Example 18.

recombinant IAP fragment (second and third BIR motifs of XIAP) is bound to 200 ml of glutathione resin as a GST-fusion protein and incubated with 0.5 mg of radiolabeled mimetics at room temperature. After extensive washing with an assay buffer containing 25 mM Tris, pH 8.0, 150 mM NaCl, and 2 mM dithiothreitol (DTT), the complex is eluted with 5 mM reduced glutathione and visualized by SDS-PAGE with Coomassie staining.

This assay demonstrates that the tested mimetics specifically bind IAP.

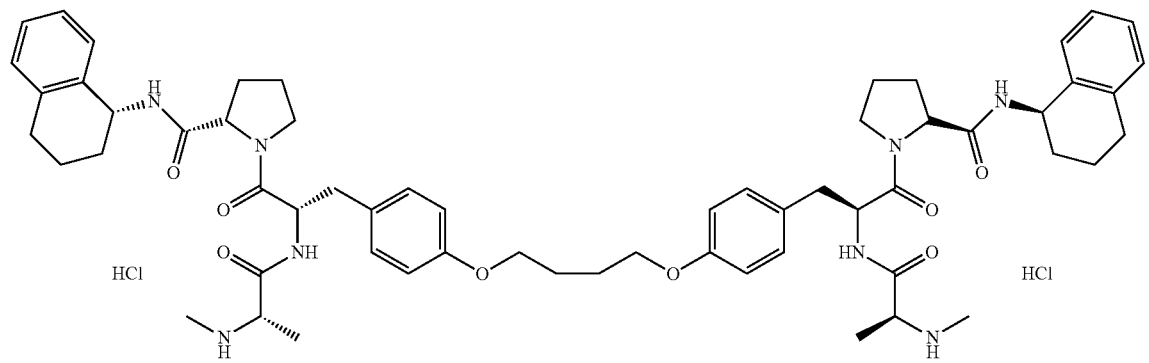

Example 22

Fluorescent Polarization Assay

Increasing concentrations of Smac compounds are incubated with 2 nM of labeled peptide (fluorescein labeled 10 mer peptide with AVPI 4 amino acids at its N terminus-Alexa Fluor 488) and truncated XIAP containing only BIR1, BIR2, and BIR3 domains at room temperature for 1 hour. Fluorescence reading, indicative of the bound portion of the labeled peptide, is measured in milipolarization units (mP). The more compound added, less fluorescein labeled peptide bind to the protein due to the competitive binding and less fluorescence signal is released.

Based on this principle, we obtain the Ki value that evaluates compound's binding affinity.

Example 23

In-Vitro Caspase-3 Activation Assay

Caspase3 in most cell extracts can be activated by the addition of 1 mM dATP through the mitochondria caspase pathway. Hela S3 cells we use to make cell extract express higher XIAP, hence after addition of dATP in Hela S100, the induced caspase3 is blocked by IAPB. Taking advantage of this feature, we use 100 nM of synthetic Smac mimetic compound to test its ability to eliminate IAPB in the Hela S100 and fully induce Caspase3 activity. The In Vitro Caspase3 assay is carried out at 30° C., incubating 100 nM compounds with 30 ug of Hela S100, 1 mM dATP, 10 uM Caspase3 fluorogenic substrate (Caspase3 Substrate II, Fluorogenic, #235425 from Calbiochem). The readout is caspase-3 activity represented by relative fluorogenic unit, which is recorded kinetically. The slope in linear region of the curve for each compound is calculated.

The ratio of each synthetic compound's slope versus the slope of control reflects in vitro caspase-3 activation ability of compounds.

Example 24

Cell Viability Assay in HCC461 Cells

HCC461 cells plated in 96 well plates at $5 \times 10^4$/ml cell density are treated with 50× synthetic Smac mimetic compounds (final concentration range between 30 uM and 0.001 uM). After 48 hrs incubation at 37° C. and 5% $CO_2$, viability of the cells are measured using Cell Proliferation Reagent WST-1 assay kit (Roche Cat #11 644 807 001).

WST-1 Assay Principle

The tetrazolium salts are cleaved to formazan by cellular enzymes. An expansion in the number of viable cells results in an increase in the overall activity of mitochondrial dehydrogenases in the samples. This augmentation in the enzyme activity leads to an increase in the amount of formazan dye formed, which directly correlates to the number of metabolically active cells in the culture. Quantification of the formazan dye produced by metabolically active cells by using a microplate (ELISA) reader at 420-480 nm.

Example 25

Synergism of TRAIL and Smac Mimetic Compounds in PANC-1 Cells

PANC-1 cells plated in 96 well plates at $5 \times 10^4$/ml cell density are pre-treated with 100 nm compounds for 4 hrs at 37° C. and 5% $CO_2$. The cells are then treated with 50× TRAIL (final concentration range between 2400 ng/ml and 0.08 ng/ml). After 48 hrs incubation at 37° C. and 5% $CO_2$, viability of the cells are measured using Cell Proliferation Reagent WST-1 assay kit (Roche Cat #11 644 807 001). Comparison between viability of cells when treated with TRAIL alone versus when treated with TRAIL +100 nm Smac mimetic compound gives us synergism picture.

WST-1 Assay Principle:

The tetrazolium salts are cleaved to formazan by cellular enzymes. An expansion in the number of viable cells results in an increase in the overall activity of mitochondrial dehydrogenases in the samples. This augmentation in the enzyme activity leads to an increase in the amount of formazan dye formed, which directly correlates to the number of metabolically active cells in the culture. Quantification of the formazan dye produced by metabolically active cells by using a microplate (ELISA) reader at 420-480 nm.

Example 26

Cell-Based Assay: Smac Peptides Potentiate Apoptosis Induced by UV or Etoposide in Cultured HeLa Cells $0.75 \times 105$ of HeLa—S cells/well are plated in 48-well tissue culture plate. Cells are incubated with 1 mM inactive Smac peptide or with 1 mM N-terminal 4-amino acid Smac peptide, with selected mimetics, or with vehicle only (Control) for 12 hr. The cells are then treated with either 320,000 microjoules of UV irradiation using a Stratalinker or with 100 mM chemotherapeutic Etoposide. Cells are then stained with 1 mg/ml Hoechst 33342 dye at different time points and apoptotic cells are counted as those with condensed nuclear chromatin under a fluorescent microscopy. Mimetics, including wild-type Smac peptides, show significant increases in apoptotic induction at 2, 4 and 6 hrs (for UV insult) and at 10 and 20 hr (for etoposide).

Example 27

In Vivo Metastasis Assay

Immunosuppressed mice (athymic nude/nude SCID females from Harlan Sprague Dawley) are housed in autoclaved cages with microisolator tops, and all manipulations of the animals are done in a laminar flow hood after wiping down both the hood, gloves and cages with ABQ sterilant. The mice are fed sterile Pico Lab Chow (Purina) and autoclaved St. Louis tap water. Mimetics are administered intra-gastrically daily to the mice in sterile water containing 2% carboxymethyl cellulose via sterile, disposable animal feeding needles (Poper & Sons Cat #9921; 20 g×1.5"), seven days a week between 7:00 and 8:00 am. The compounds and control (sterile water plus 2% carboxymethyl cellulose) are kept stored at −80° C. wrapped in aluminum foil to prevent any light induced changes, and each day's supply is thawed just prior to use.

Compounds are tested for their effects on the metastatic potential of C8161 cells injected intravenously via the tail vein: at 40 and 100 mg/kg, compared to the control. The concentration of the compounds in the vials used to give the 100 mg/kg doses are 2.5 times that in the 40 mg/kg dose so that approximately the same volume is used in both cases, approximately 0.5 mL/animal. The experiments start with nine animals per group at day −4. On day zero, $2 \times 10^5$ C8161 cells in cold Hank's Balanced Salt Solution (HBSS) are injected intravenously via tail vein inoculation. The protocol is continued for an additional 24 days, at which time the animals are sacrificed and their lungs removed and fixed in a solution of Bouins/formaldehyde (5 parts:1 part). Tumors are quantified on the entire surface of the lungs by rotating the lungs and counting the tumors on each lobe using a 6× magnifying glass. Statistical analysis is performed using the statistical package of Microsoft's Excel spreadsheet software.

The effects of test mimetics, at two different concentrations, on the metastatic potential of C8161 cells in SCID mice are evaluated: oral gavaging of the animals with mimetics significantly reduces the number of lung metastases in the SCID mouse population.

Example 28

In Vivo Combination Therapy: B.I.D. & Q.I.D.

The effect of in vivo combination therapy of mimetics (20 or 80 mpk/dosing p.o. or i.p.) with chemotherapies paclitaxel (5 or 20 mpk), 5-Fu (50 mpk), vincristine (1 mpk) or cytoxan (100 mpk, BID, ip) on HTB 177 xenografts (NCI-H460, a human lung large cell carcinoma) using two and four times a day dosing is demonstrated in athymic nu/nu female mice, 5-6 weeks old. On Day 0, HTB 177 cells, $3 \times 10^6$, are injected s.c. into the flank of 220 mice and the mice divided into treatment and control groups:

Mimetics are dissolved in 20% hydroxyl-propyl-betacyclodexatrin (Vehicle I); 0.2 ml of mimetic solution is the dosing volume. Paclitaxel is dissolved in a diluted ethanol/cremophor EL solution (Vehicle II) and the i.p. dosing volume for paclitaxel is 0.1 ml. Cytoxan, 5-FU, and Vincristine are dissolved in sterile water. The 80 mpk dosing mimetic solution is made by adding 17 ml of 20% HPBCD to a 50 ml tube containing 136 mg of mimetic to dissolve. The mixture is sonicated until a complete solution was made. The 20 mpk dosing solution is made by placing 2 ml of the 80 mpk solution into a 15 ml tube, adding 6 ml of 20% HPBCD, and vortexing the solution to mix it.

Tumor cells are inoculated into mice in the morning of Day 0, and the mice weighed, randomized, and ear-marked afterwards. Drug treatment begins at 7:30 am on Day 4. The animals are dosed with mimetic or vehicle I solution, at 7:30 am, and 7:30 pm, 7 days a week. Tumor growth is quantitated by measuring tumor volume on Day 7 and Day 14.

Both mimetic and chemotherapies demonstrate inhibition; combination therapies provide enhanced inhibition over either therapy alone.

Example 29

In Vivo Therapy in the WAP-RAS Transgenic Model

Mimetic and Paclitaxel combination efficacy is also evaluated in the Wap-ras transgenic model. This model is used in a therapeutic mode in which treatments are initiated after mice had well developed tumors.

Mimetics (20 mpk/dosing po) are dissolved in 20% hydroxyl-propyl-betacyclodextrin (Vehicle I). 0.2 ml of mimetic solution is the oral dosing volume. Paclitaxel (5 mpk/dosing ip) is dissolved in a diluted ethanol/cremophor EL solution (vehicle II) and the i.p. dosing volume for paclitaxel is 0.1 ml.

The mice are weighed, randomized, and ear-marked on Day 0. Mimetic treatment and Vehicle I treatment is begun on Day 1 and continued every 12 hours until Day 21. Paclitaxel and Vehicle II treatments are started on Day 4 and continued daily on Day 5, 6, and 7.

Wap-ras tumors do not respond to treatment with Paclitaxel but do respond to mimetic treatment at 20 mpk alone and combined therapy enhances efficacy.

Example 30

Representative Biological Activity Data

TABLE 1

Representative Bioassay Data

| Compound No. | Bioassay data | | | |
|---|---|---|---|---|
| | Bir binding (μM) | HCC461 cell (μM) | Caspase % | Notes |
| 1 (Example 6) | 0.07 | 0.004 | 100 | Caspase std. |
| 2 (Example 7) | 0.15 | 0.01 | 105 | |
| 3 | 0.12 | 0.026 | 48 | |
| 4 | 0.11 | 0.025 | 55 | |
| 6 | 0.2 | 2.1 | 82 | |
| 7 | 0.144 | 0.373 | 101 | |
| 8 | 0.27 | 0.07 | 93 | |
| 9 | 0.196 | 0.009 | 108 | |
| 10 | 0.2 | 0.02 | 105 | |
| 11 | 0.172 | 0.012 | 94 | |
| 13 | 0.188 | 0.07 | 105 | |
| 14 | 0.158 | 0.62 | 104 | |
| 15 | 0.638 | 0.08 | 87 | |
| 16 | 0.22 | 0.025 | 107 | |
| 17 | 0.136 | 0.69 | 98 | |
| 18 | 0.176 | 0.76 | 88 | |
| 19 | 0.14 | 0.24 | 98 | |
| 20 | 0.18 | 0.52 | 99 | |
| 21 | 1.13 | 2.2 | 70 | |
| 22 | 0.13 | 0.81 | 106 | |
| 23 | 0.13 | 0.49 | 109 | |
| 24 | 1.5 | 1.4 | 81 | |
| 26 | 0.235 | 0.1 | 106 | |
| 28 | 0.2 | 0.07 | 102 | |
| 32 | 0.08 | 0.005 | 109 | |
| 36 | 0.19 | 0.05 | 98 | |
| 37 | 0.3 | 0.2 | 59 | |
| 38 | 0.2 | 0.07 | 102 | |
| 39 | 0.18 | 0.16 | 102 | |
| 40 | 0.15 | 0.03 | 85 | |
| 41 | 0.3 | 0.02 | 99 | |
| 42 | 0.2 | 0.24 | 109 | |
| 43 | 0.2 | 0.1 | 104 | |
| 44 (Example 19) | 0.18 | 0.003 | 104 | |
| 45 (Example 20) | 0.15 | 0.002 | 136 | |
| 47 | 0.19 | 0.02 | 99 | |
| 48 | 0.2 | 0.056 | 103 | |
| 49 | 0.19 | 0.02 | 113 | |
| 50 | 0.2 | 0.02 | 97 | |

Using methods similar to those described for the foregoing Examples, the compounds of Table 2 can readily be prepared and shown to be Smac mimetics.

TABLE 2
Representative Dimers
| Compound No. | Structure |
|---|---|
| 1 (Example 6) | 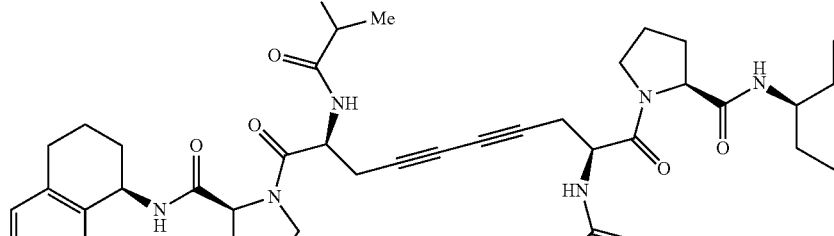 |
| 2 (Example 7) | 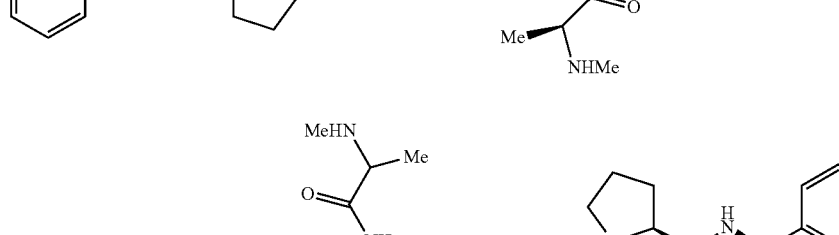 |
| 3 | 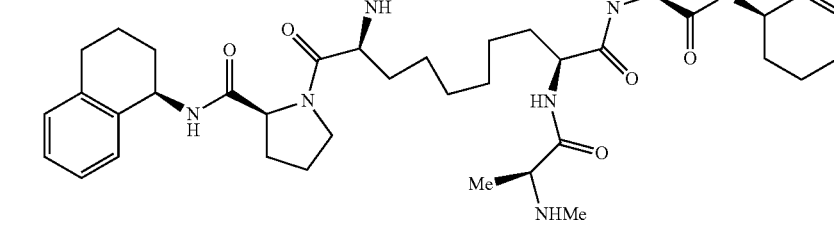 |
| 4 | 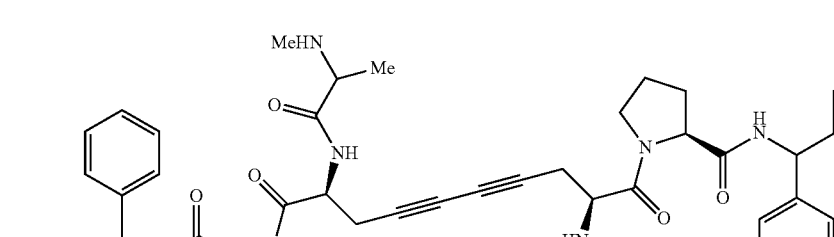 |

TABLE 2-continued

Representative Dimers

| Compound No. | Structure |
| --- | --- |
| 5 | (chemical structure) |
| 6 | (chemical structure) |
| 7 | (chemical structure) |
| 8 | (chemical structure) |

TABLE 2-continued

Representative Dimers

| Compound No. | Structure |
|---|---|
| 9 | 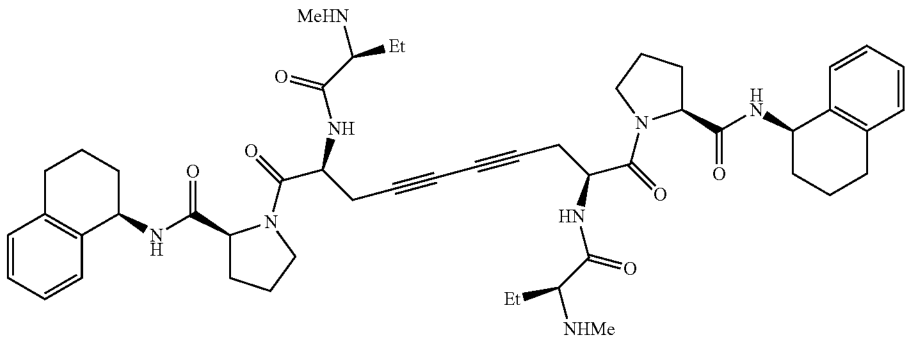 [SMILES: CC[C@H](NC)C(=O)N[C@@H](CC#CC#CC[C@H](NC(=O)[C@H](CC)NC)C(=O)N1CCC[C@H]1C(=O)N[C@@H]1CCCc2ccccc21)C(=O)N1CCC[C@H]1C(=O)N[C@@H]1CCCc2ccccc21] |
| 10 | 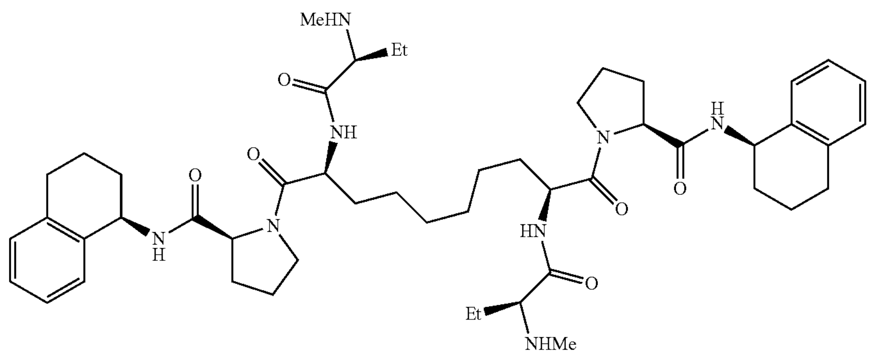 [SMILES: CC[C@H](NC)C(=O)N[C@@H](CCCCCC[C@H](NC(=O)[C@H](CC)NC)C(=O)N1CCC[C@H]1C(=O)N[C@@H]1CCCc2ccccc21)C(=O)N1CCC[C@H]1C(=O)N[C@@H]1CCCc2ccccc21] |
| 11 | 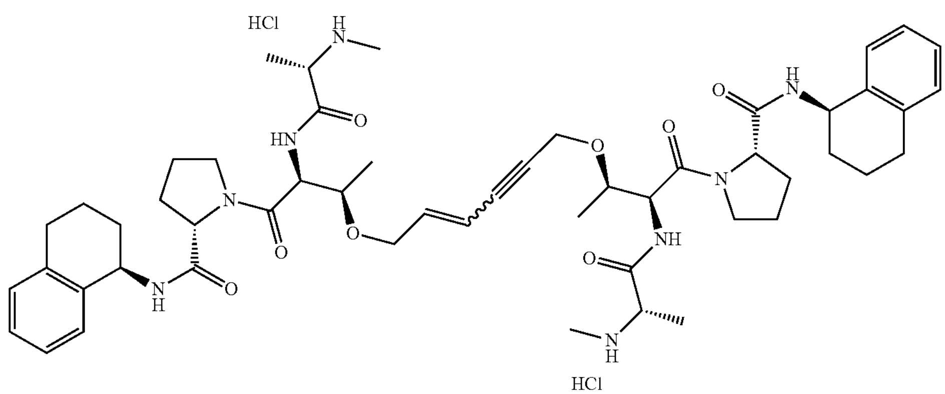 [SMILES: Cl ; CN[C@@H](C)C(=O)N[C@H](C(=O)N1CCC[C@H]1C(=O)N[C@@H]1CCCc2ccccc21)[C@@H](C)OCC#CC=CCO[C@H](C)[C@H](NC(=O)[C@H](C)NC)C(=O)N1CCC[C@H]1C(=O)N[C@@H]1CCCc2ccccc21 ; Cl] |
| 12 | 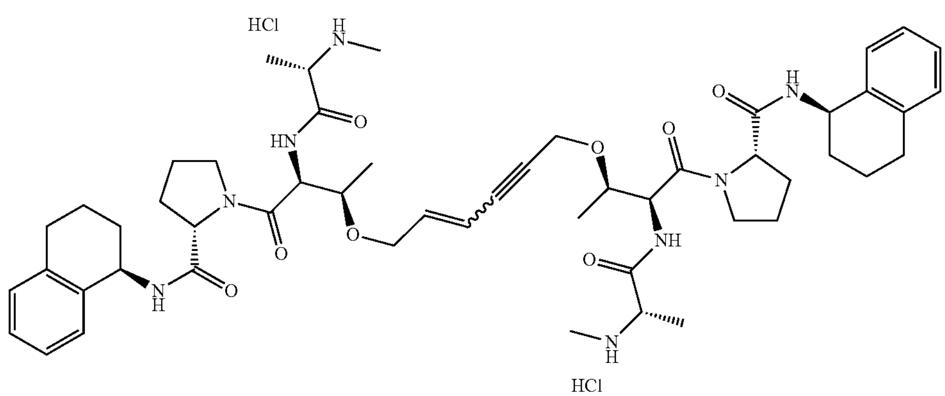 [SMILES: Cl ; CN[C@@H](C)C(=O)N[C@H](C(=O)N1CCC[C@H]1C(=O)N[C@@H]1CCCc2ccccc21)[C@@H](C)OCC#CC=CCO[C@H](C)[C@H](NC(=O)[C@H](C)NC)C(=O)N1CCC[C@H]1C(=O)N[C@@H]1CCCc2ccccc21 ; Cl] |

TABLE 2-continued
Representative Dimers
| Compound No. | Structure |
|---|---|
| 13 | 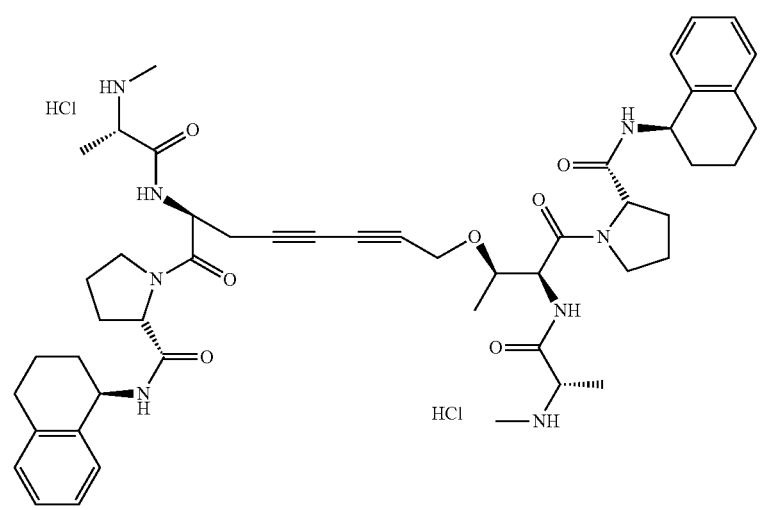 |
| 14 | 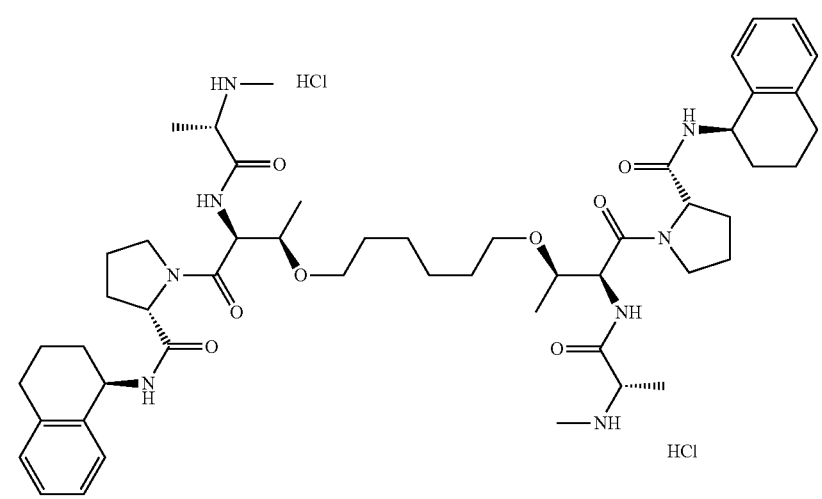 |
| 15 | 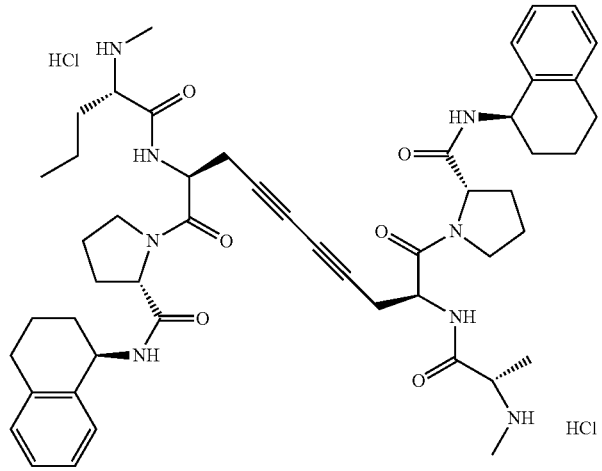 [SMILES: CCC[C@H](NC)C(=O)N[C@@H](CC#CC#CC[C@H](NC(=O)[C@H](C)NC)C(=O)N1CCC[C@H]1C(=O)N[C@@H]1CCCc2ccccc21)C(=O)N1CCC[C@H]1C(=O)N[C@@H]1CCCc2ccccc21 ; Cl ; Cl] |

TABLE 2-continued
Representative Dimers
| Compound No. | Structure |
| --- | --- |
| 16 | 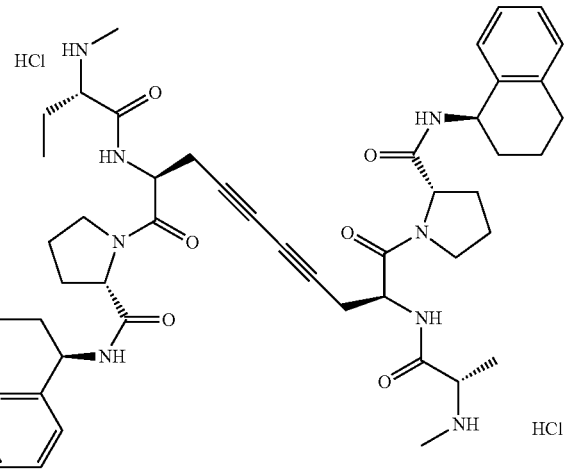 |
| 17 | 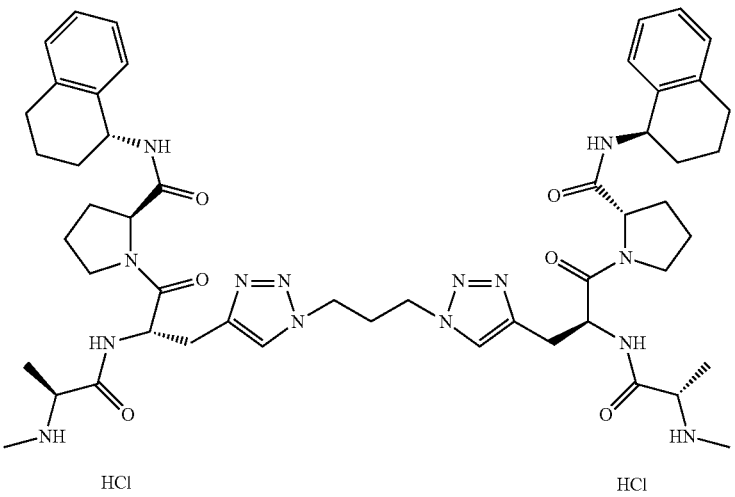 |
| 18 | 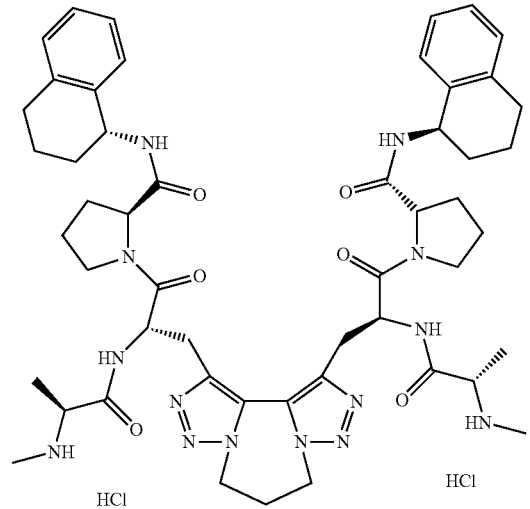 |

TABLE 2-continued
Representative Dimers
| Compound No. | Structure |
|---|---|
| 19 | 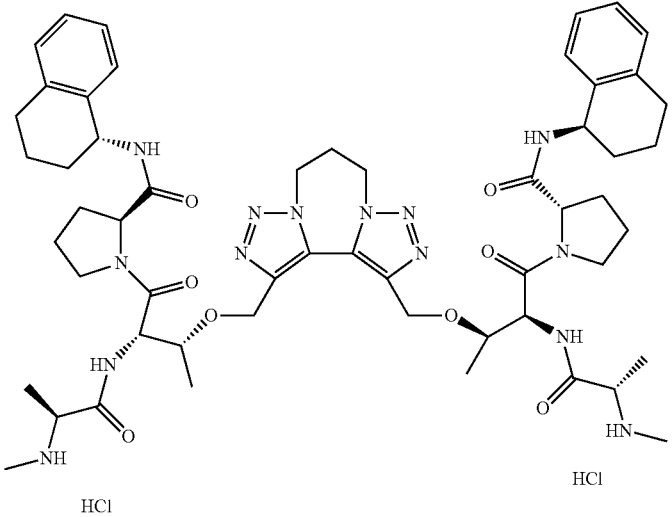 |
| 20 | 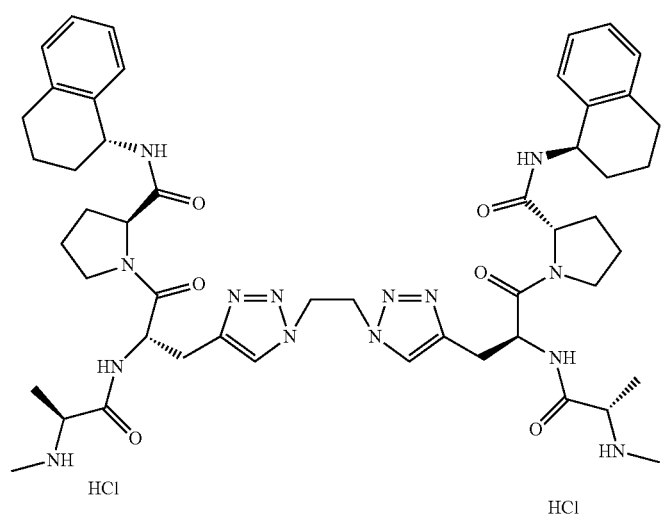 |
| 21 | 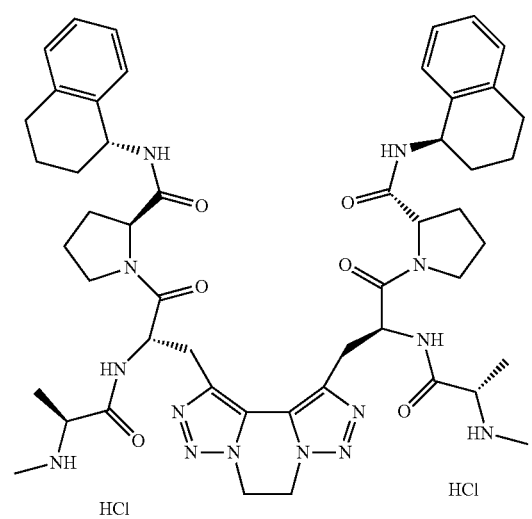 |

US 8,586,542 B2
TABLE 2-continued
Representative Dimers
| Compound No. | Structure |
|---|---|
| 22 | 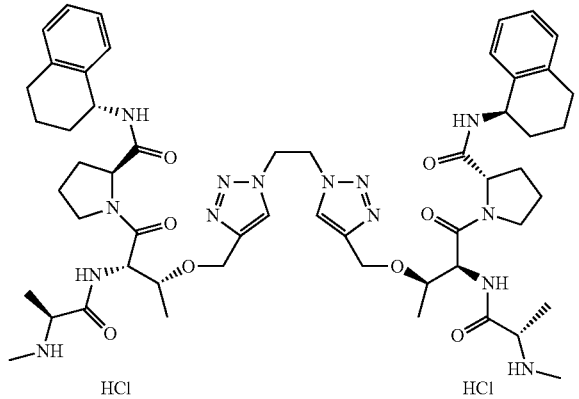 [SMILES: CN[C@@H](C)C(=O)N[C@H](C(=O)N1CCC[C@H]1C(=O)N[C@@H]1CCCc2ccccc21)[C@@H](C)OCc1cn(CCn2cc(CO[C@H](C)[C@H](NC(=O)[C@H](C)NC)C(=O)N3CCC[C@H]3C(=O)N[C@@H]3CCCc4ccccc43)nn2)nn1 ; Cl ; Cl] |
| 23 | 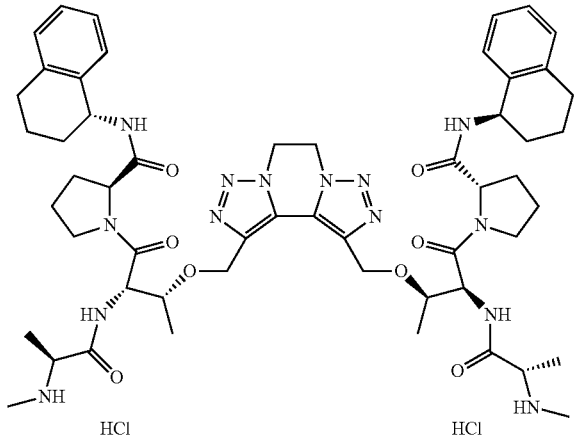 [SMILES: CN[C@@H](C)C(=O)N[C@H](C(=O)N1CCC[C@H]1C(=O)N[C@@H]1CCCc2ccccc21)[C@@H](C)OCc1nnn2c1-c1c(CO[C@H](C)[C@H](NC(=O)[C@H](C)NC)C(=O)N3CCC[C@H]3C(=O)N[C@@H]3CCCc4ccccc43)nnn1CC2 ; Cl ; Cl] |
| 24 | 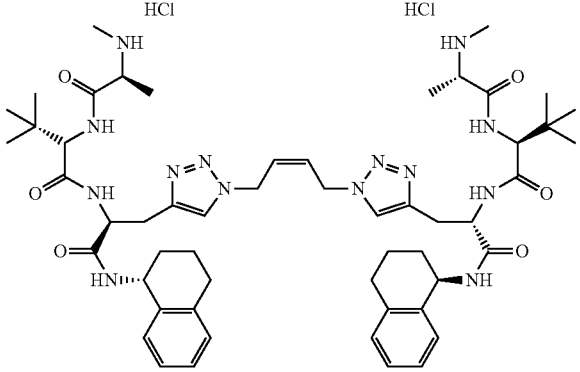 |

TABLE 2-continued

Representative Dimers

| Compound No. | Structure |
|---|---|
| 25 | 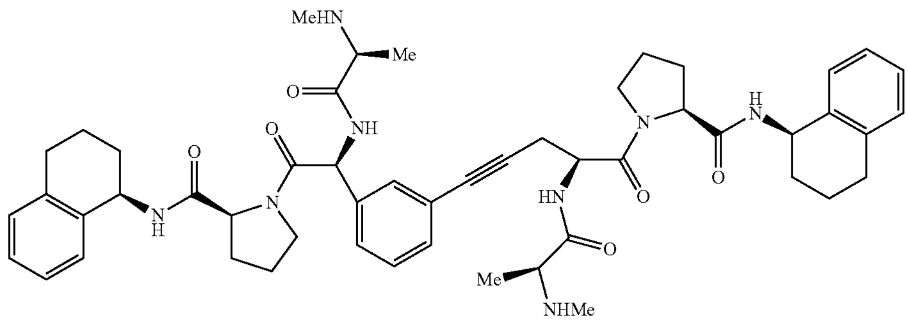 [SMILES: CN[C@@H](C)C(=O)N[C@@H](CC#Cc1cccc([C@H](NC(=O)[C@H](C)NC)C(=O)N2CCC[C@H]2C(=O)N[C@@H]2CCCc3ccccc32)c1)C(=O)N1CCC[C@H]1C(=O)N[C@@H]1CCCc2ccccc21] |
| 26 | 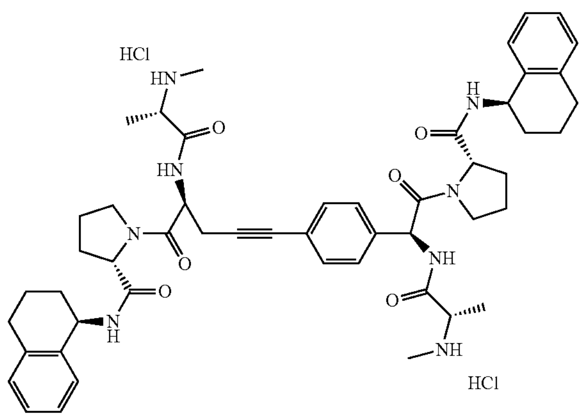 [SMILES: CN[C@@H](C)C(=O)N[C@@H](CC#Cc1ccc([C@H](NC(=O)[C@H](C)NC)C(=O)N2CCC[C@H]2C(=O)N[C@@H]2CCCc3ccccc32)cc1)C(=O)N1CCC[C@H]1C(=O)N[C@@H]1CCCc2ccccc21 ; Cl ; Cl] |
| 27 | 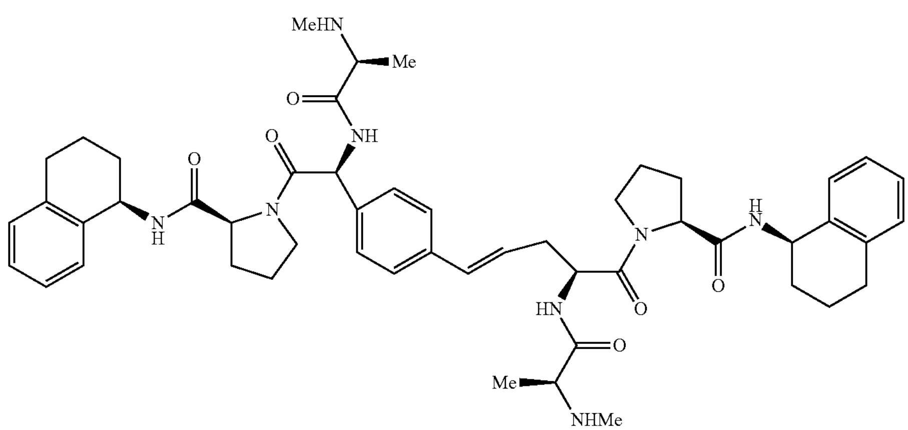 [SMILES: CN[C@@H](C)C(=O)N[C@@H](C/C=C/c1ccc([C@H](NC(=O)[C@H](C)NC)C(=O)N2CCC[C@H]2C(=O)N[C@@H]2CCCc3ccccc32)cc1)C(=O)N1CCC[C@H]1C(=O)N[C@@H]1CCCc2ccccc21] |

TABLE 2-continued

Representative Dimers

| Compound No. | Structure |
| --- | --- |
| 28 | 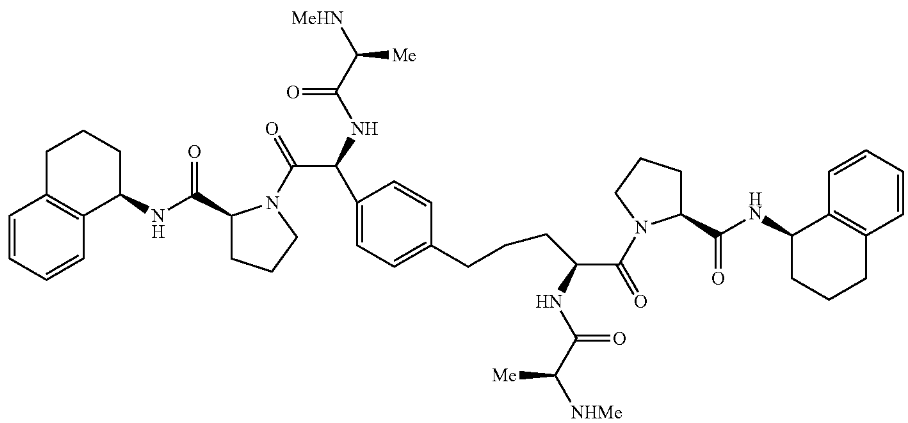 [SMILES: CN[C@@H](C)C(=O)N[C@@H](CCCc1ccc([C@H](NC(=O)[C@H](C)NC)C(=O)N2CCC[C@H]2C(=O)N[C@@H]2CCCc3ccccc32)cc1)C(=O)N1CCC[C@H]1C(=O)N[C@@H]1CCCc2ccccc21] |
| 29 | 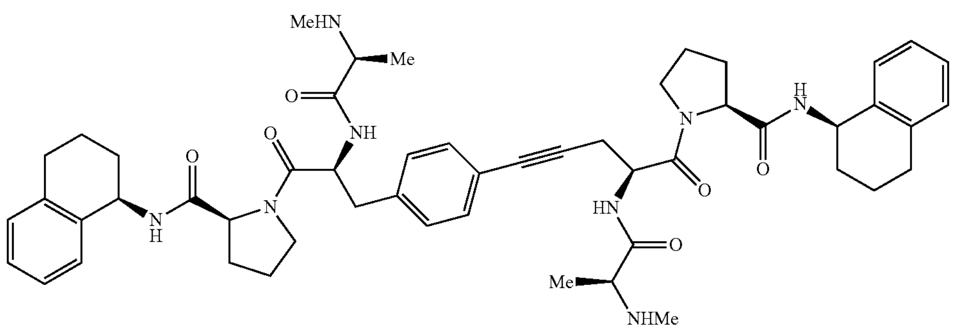 [SMILES: CN[C@@H](C)C(=O)N[C@@H](CC#Cc1ccc(C[C@H](NC(=O)[C@H](C)NC)C(=O)N2CCC[C@H]2C(=O)N[C@@H]2CCCc3ccccc32)cc1)C(=O)N1CCC[C@H]1C(=O)N[C@@H]1CCCc2ccccc21] |
| 30 | 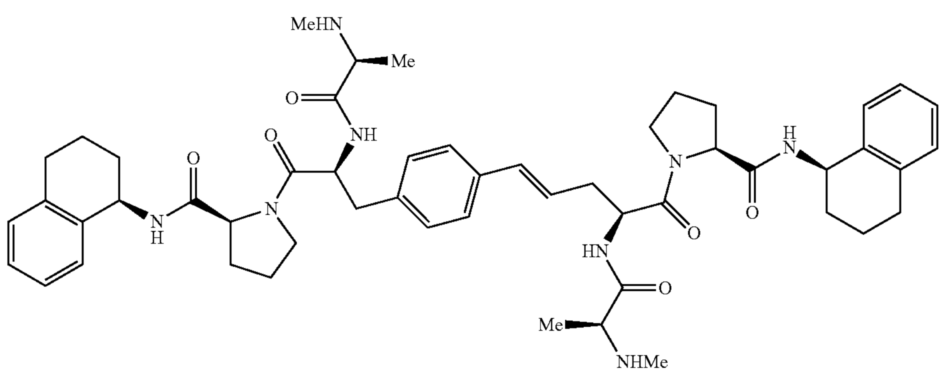 [SMILES: CN[C@@H](C)C(=O)N[C@@H](C/C=C/c1ccc(C[C@H](NC(=O)[C@H](C)NC)C(=O)N2CCC[C@H]2C(=O)N[C@@H]2CCCc3ccccc32)cc1)C(=O)N1CCC[C@H]1C(=O)N[C@@H]1CCCc2ccccc21] |
| 31 | 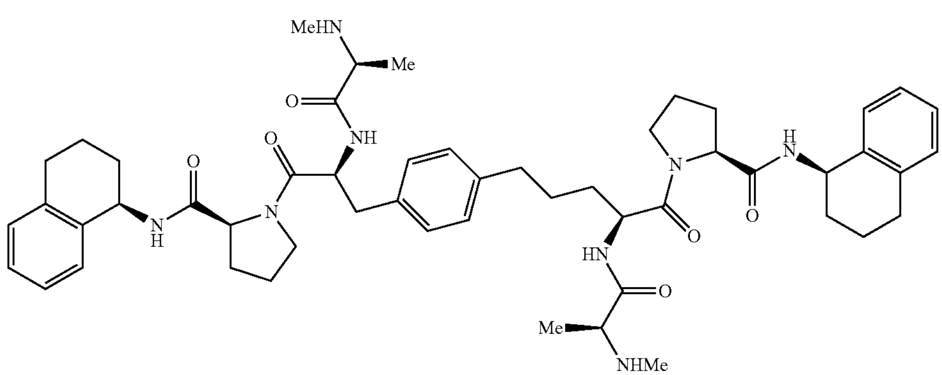 [SMILES: CN[C@@H](C)C(=O)N[C@@H](CCCc1ccc(C[C@H](NC(=O)[C@H](C)NC)C(=O)N2CCC[C@H]2C(=O)N[C@@H]2CCCc3ccccc32)cc1)C(=O)N1CCC[C@H]1C(=O)N[C@@H]1CCCc2ccccc21] |

TABLE 2-continued

Representative Dimers

| Compound No. | Structure |
|---|---|
| 32 (Example 14) | 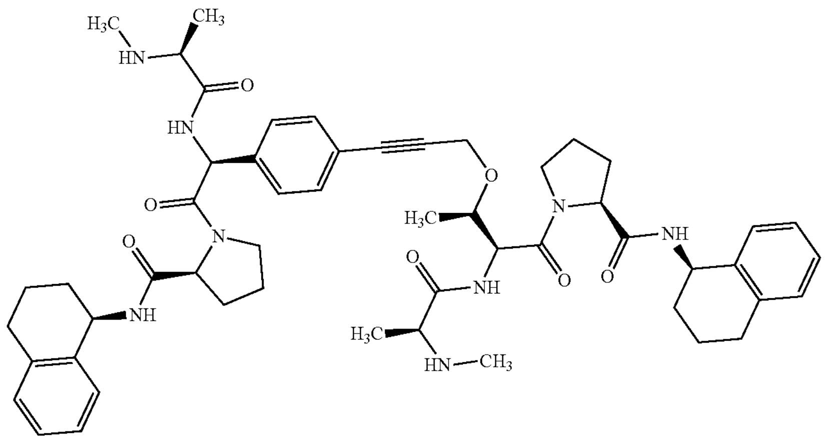 [SMILES: CN[C@@H](C)C(=O)N[C@H](C(=O)N1CCC[C@H]1C(=O)N[C@@H]1CCCc2ccccc21)c1ccc(C#CCO[C@H](C)[C@H](NC(=O)[C@H](C)NC)C(=O)N2CCC[C@H]2C(=O)N[C@@H]2CCCc3ccccc32)cc1] |
| 33 | 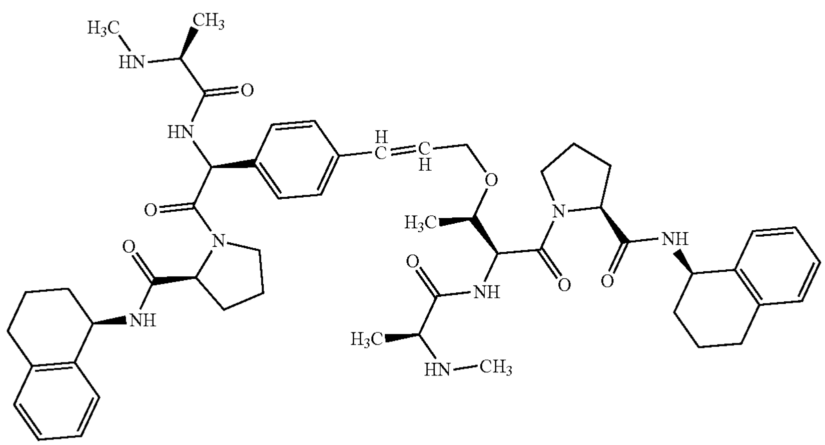 [SMILES: CN[C@@H](C)C(=O)N[C@H](C(=O)N1CCC[C@H]1C(=O)N[C@@H]1CCCc2ccccc21)c1ccc(C=CCO[C@H](C)[C@H](NC(=O)[C@H](C)NC)C(=O)N2CCC[C@H]2C(=O)N[C@@H]2CCCc3ccccc32)cc1] |
| 34 | 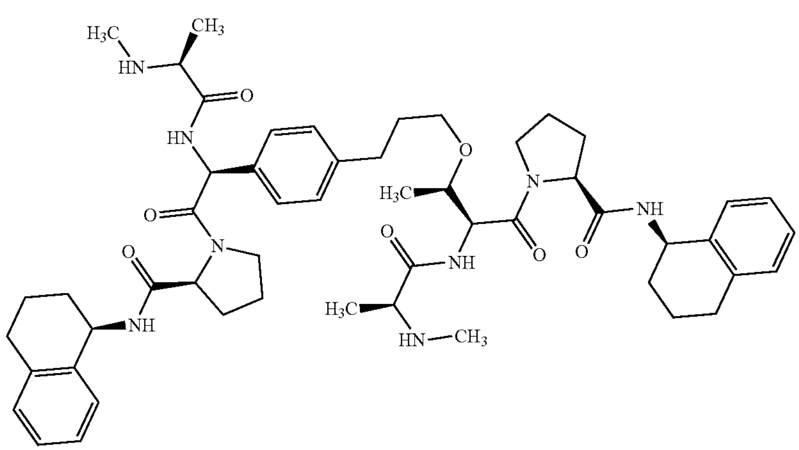 [SMILES: CN[C@@H](C)C(=O)N[C@H](C(=O)N1CCC[C@H]1C(=O)N[C@@H]1CCCc2ccccc21)c1ccc(CCCO[C@H](C)[C@H](NC(=O)[C@H](C)NC)C(=O)N2CCC[C@H]2C(=O)N[C@@H]2CCCc3ccccc32)cc1] |

TABLE 2-continued
Representative Dimers
| Compound No. | Structure |
|---|---|
| 35 | 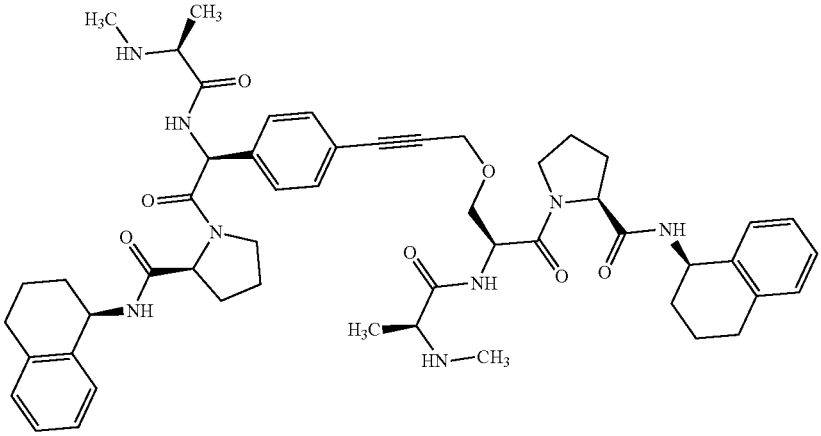 [SMILES: CN[C@@H](C)C(=O)N[C@@H](COCC#Cc1ccc([C@H](NC(=O)[C@H](C)NC)C(=O)N2CCC[C@H]2C(=O)N[C@@H]2CCCc3ccccc32)cc1)C(=O)N1CCC[C@H]1C(=O)N[C@@H]1CCCc2ccccc21] |
| 36 | 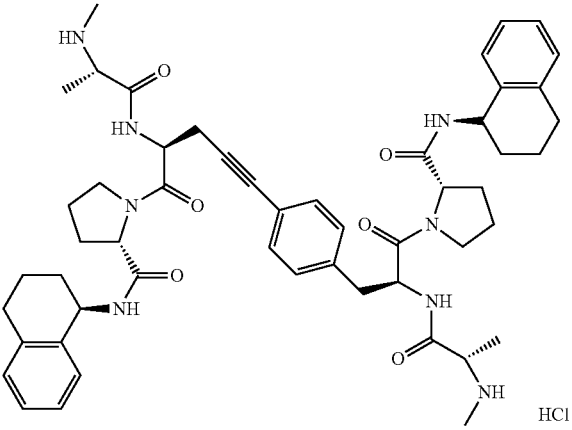 |
| 37 | 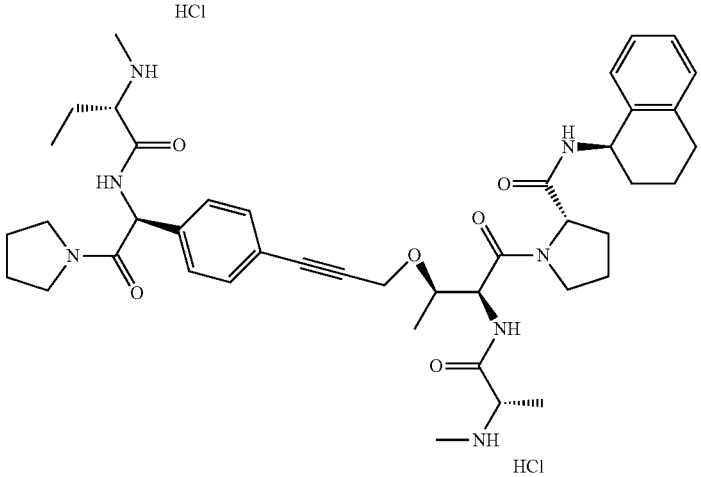 [SMILES: Cl ; CC[C@H](NC)C(=O)N[C@H](C(=O)N1CCCC1)c1ccc(C#CCO[C@H](C)[C@H](NC(=O)[C@H](C)NC)C(=O)N2CCC[C@H]2C(=O)N[C@@H]2CCCc3ccccc32)cc1 ; Cl] |

TABLE 2-continued
Representative Dimers
| Compound No. | Structure |
|---|---|
| 38 | 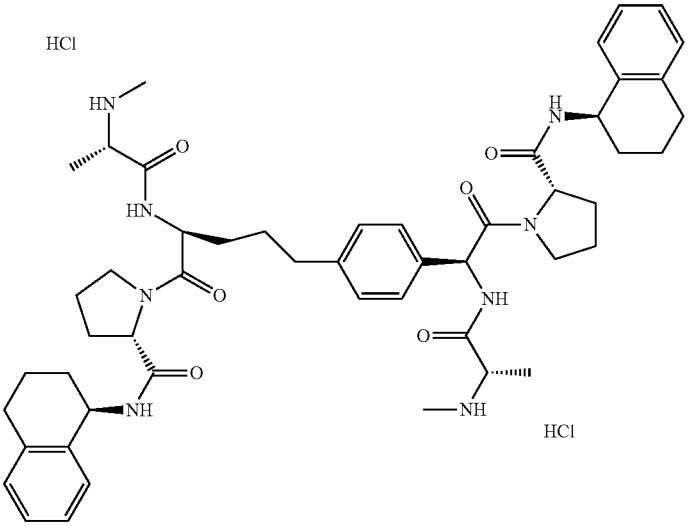 [SMILES: CN[C@@H](C)C(=O)N[C@@H](CCCc1ccc([C@H](NC(=O)[C@H](C)NC)C(=O)N2CCC[C@H]2C(=O)N[C@@H]2CCCc3ccccc32)cc1)C(=O)N1CCC[C@H]1C(=O)N[C@@H]1CCCc2ccccc21 ; Cl ; Cl] |
| 39 | 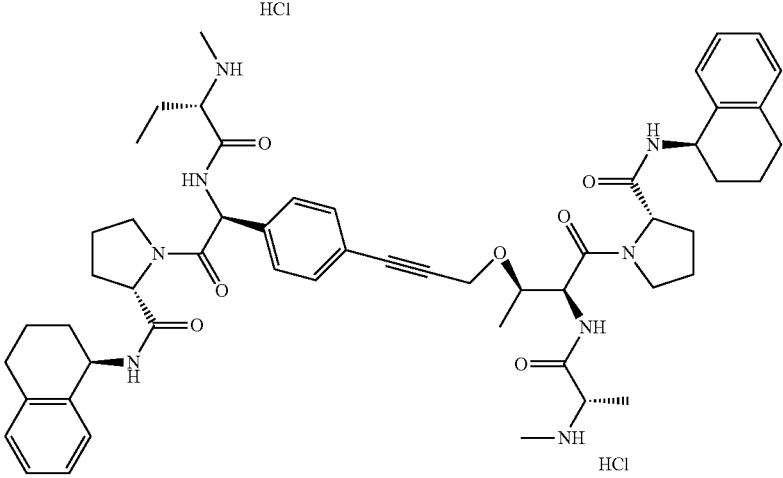 [SMILES: Cl ; CC[C@H](NC)C(=O)N[C@H](C(=O)N1CCC[C@H]1C(=O)N[C@@H]1CCCc2ccccc21)c1ccc(C#CCO[C@H](C)[C@H](NC(=O)[C@H](C)NC)C(=O)N2CCC[C@H]2C(=O)N[C@@H]2CCCc3ccccc32)cc1 ; Cl] |
| 40 | 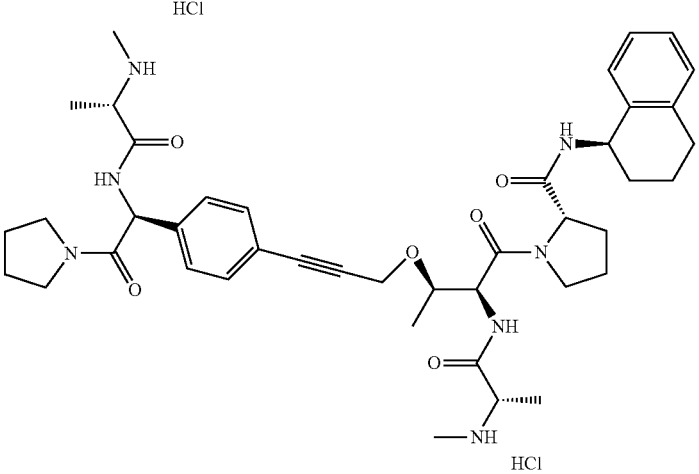 [SMILES: Cl ; CN[C@@H](C)C(=O)N[C@H](C(=O)N1CCCC1)c1ccc(C#CCO[C@H](C)[C@H](NC(=O)[C@H](C)NC)C(=O)N2CCC[C@H]2C(=O)N[C@@H]2CCCc3ccccc32)cc1 ; Cl] |

TABLE 2-continued
Representative Dimers
| Compound No. | Structure |
|---|---|
| 41 | 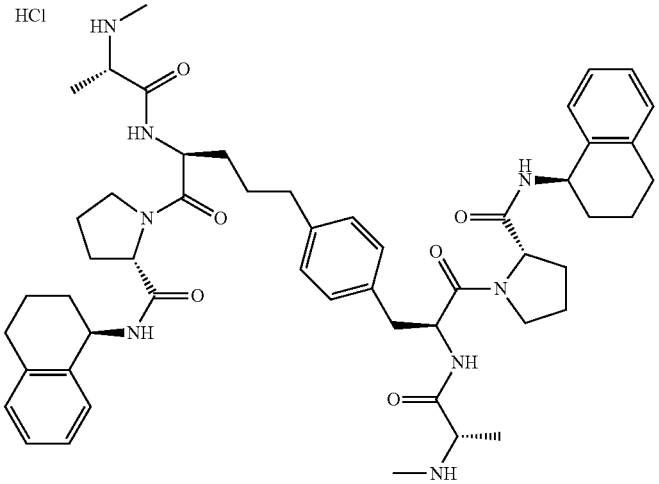 |
| 42 | 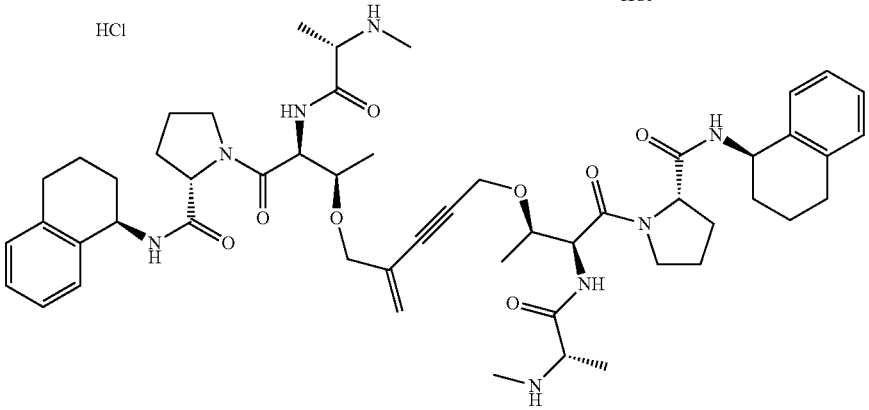 |
| 43 | 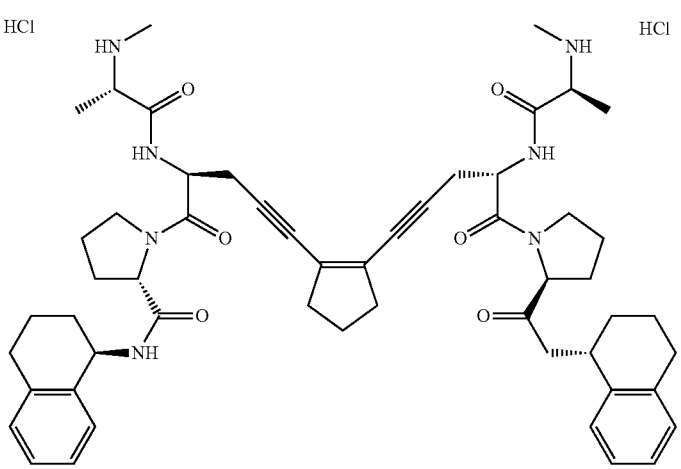 |

TABLE 2-continued

Representative Dimers

| Compound No. | Structure |
|---|---|
| 44 (Example 19) | 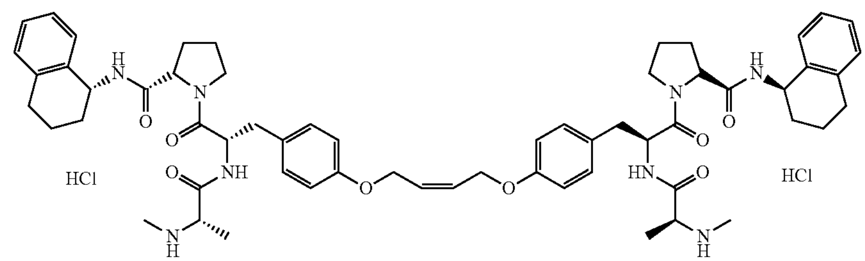 |
| 45 (Example 20) | 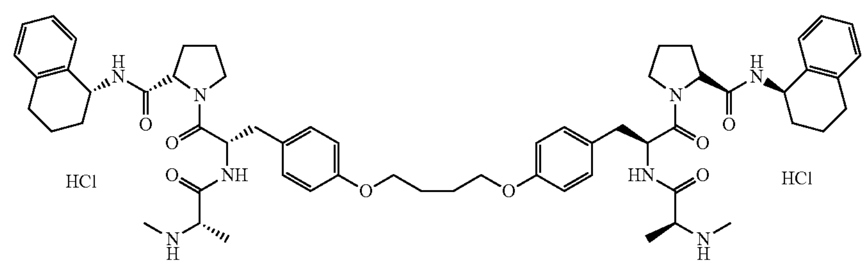 |
| 46 | 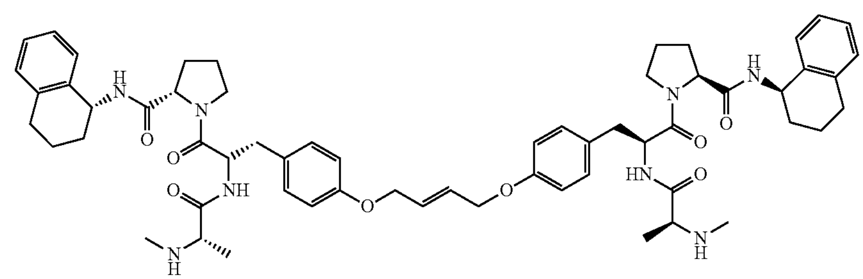 |
| 47 | 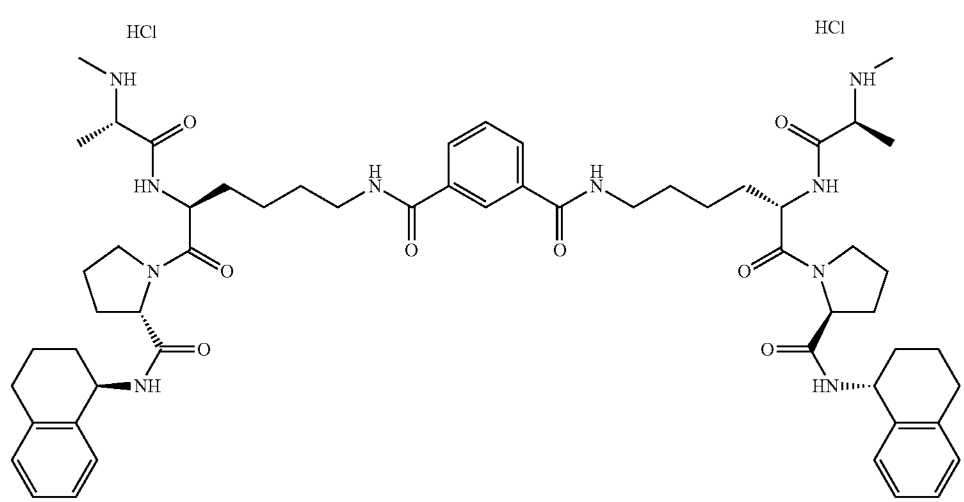 [SMILES: Cl ; Cl ; CN[C@@H](C)C(=O)N[C@@H](CCCCNC(=O)c1cccc(C(=O)NCCCC[C@H](NC(=O)[C@H](C)NC)C(=O)N2CCC[C@H]2C(=O)N[C@@H]2CCCc3ccccc32)c1)C(=O)N1CCC[C@H]1C(=O)N[C@@H]1CCCc2ccccc21] |

TABLE 2-continued
Representative Dimers
| Compound No. | Structure |
|---|---|
| 48 | 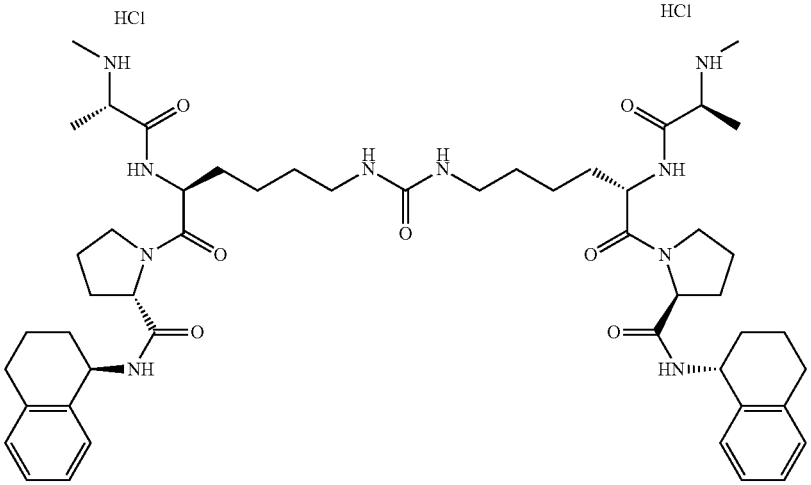 [SMILES: Cl ; Cl ; CN[C@@H](C)C(=O)N[C@@H](CCCCNC(=O)NCCCC[C@H](NC(=O)[C@H](C)NC)C(=O)N1CCC[C@H]1C(=O)N[C@@H]1CCCc2ccccc21)C(=O)N1CCC[C@H]1C(=O)N[C@@H]1CCCc2ccccc21] |
| 49 | 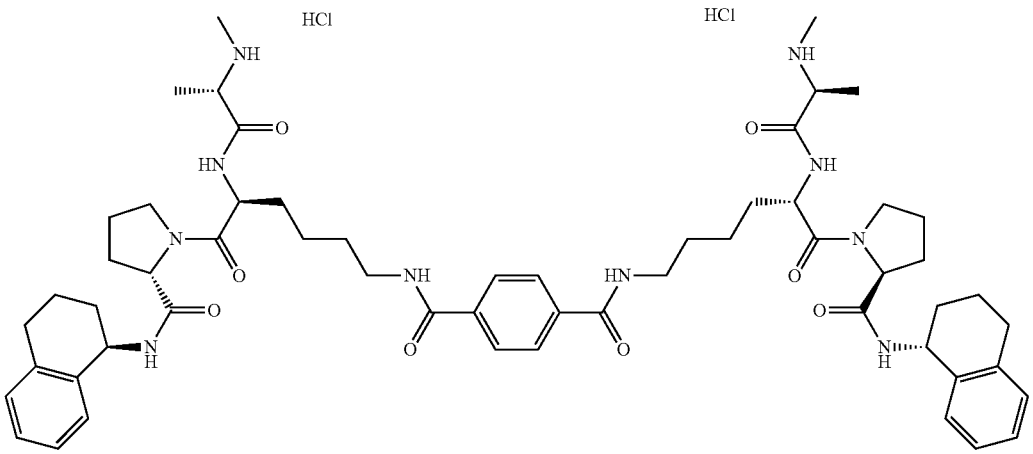 [SMILES: Cl ; CN[C@@H](C)C(=O)N[C@@H](CCCCNC(=O)c1ccc(C(=O)NCCCC[C@H](NC(=O)[C@H](C)NC)C(=O)N2CCC[C@H]2C(=O)N[C@@H]2CCCc3ccccc32)cc1)C(=O)N1CCC[C@H]1C(=O)N[C@@H]1CCCc2ccccc21 ; Cl] |
| 50 | 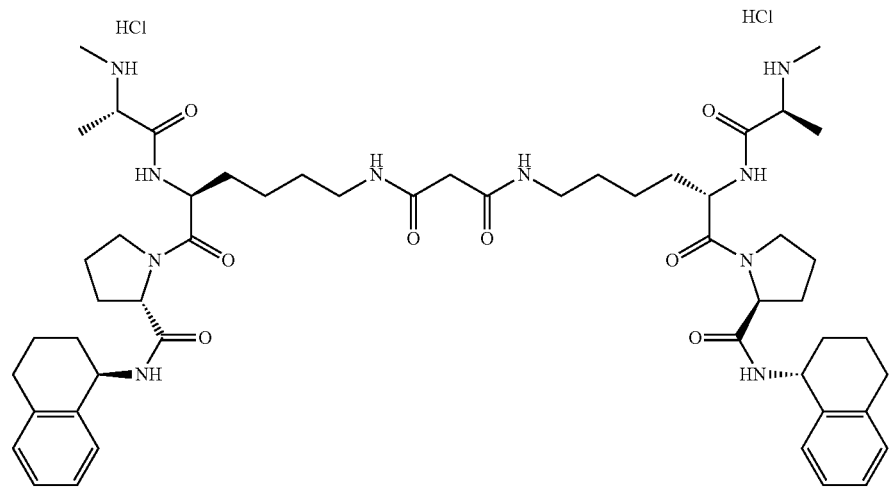 [SMILES: Cl ; Cl ; CN[C@@H](C)C(=O)N[C@@H](CCCCNC(=O)CC(=O)NCCCC[C@H](NC(=O)[C@H](C)NC)C(=O)N1CCC[C@H]1C(=O)N[C@@H]1CCCc2ccccc21)C(=O)N1CCC[C@H]1C(=O)N[C@@H]1CCCc2ccccc21] |

TABLE 3

Representative Monomers

| Compound No. | Structure |
|---|---|
| 51 (Example 1) | 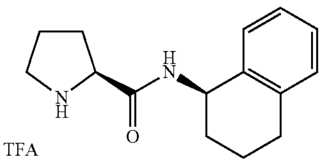 [SMILES: O=C(N[C@@H]1CCCc2ccccc21)[C@@H]1CCCN1] |
| 52 (Example 2) | 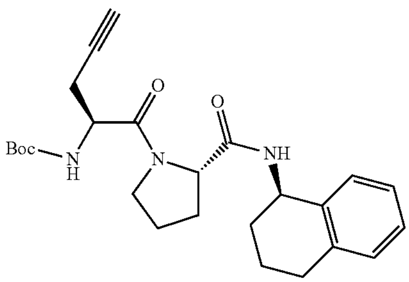 [SMILES: C#CC[C@H](NC(=O)OC(C)(C)C)C(=O)N1CCC[C@H]1C(=O)N[C@@H]1CCCc2ccccc21] |
| 53 (Example 3) | 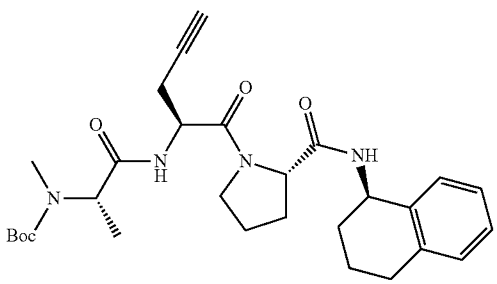 [SMILES: C#CC[C@H](NC(=O)[C@H](C)N(C)C(=O)OC(C)(C)C)C(=O)N1CCC[C@H]1C(=O)N[C@@H]1CCCc2ccccc21] |
| 54 (Example 4) | 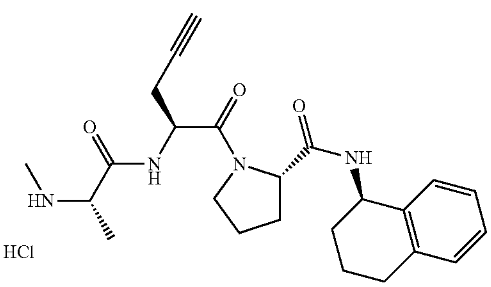 [SMILES: Cl ; C#CC[C@H](NC(=O)[C@H](C)NC)C(=O)N1CCC[C@H]1C(=O)N[C@@H]1CCCc2ccccc21] |
| 55 | 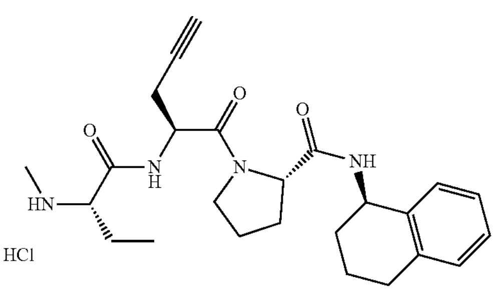 [SMILES: Cl ; C#CC[C@H](NC(=O)[C@H](CC)NC)C(=O)N1CCC[C@H]1C(=O)N[C@@H]1CCCc2ccccc21] |
| 56 | |
| 57 | |
| 58 | |
| 59 | |
| 60 | |

TABLE 3-continued
Representative Monomers
| Compound No. | Structure |
|---|---|
| 61 (Example 8) | 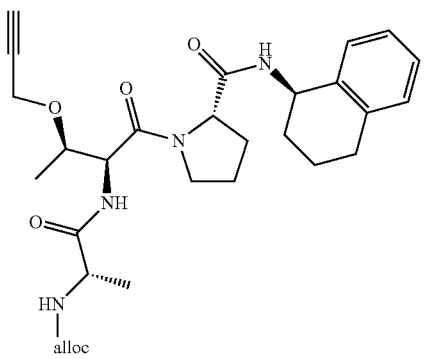 |
| 62 (Example 9) | 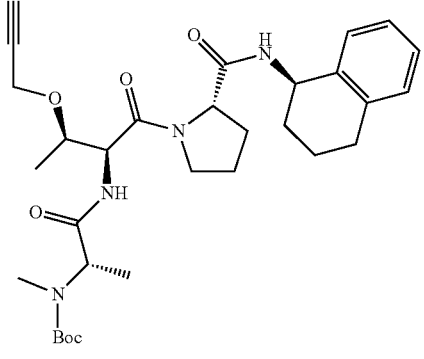 [SMILES: C#CCO[C@H](C)[C@H](NC(=O)[C@H](C)N(C)C(=O)OC(C)(C)C)C(=O)N1CCC[C@H]1C(=O)N[C@@H]1CCCc2ccccc21] |
| 63 | 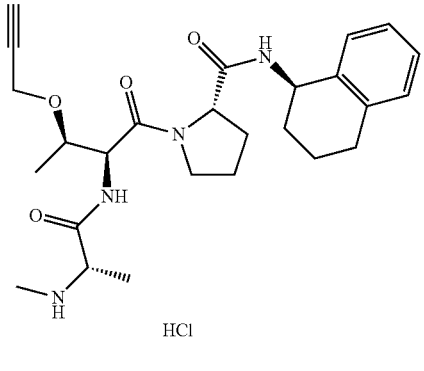 [SMILES: C#CCO[C@H](C)[C@H](NC(=O)[C@H](C)NC)C(=O)N1CCC[C@H]1C(=O)N[C@@H]1CCCc2ccccc21 ; Cl] |
| 64 | 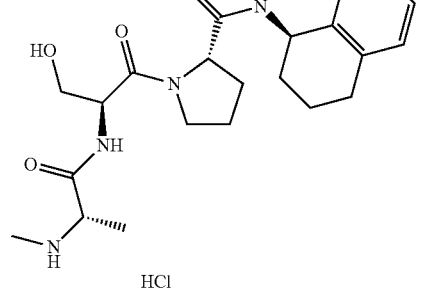 |
| 65 | 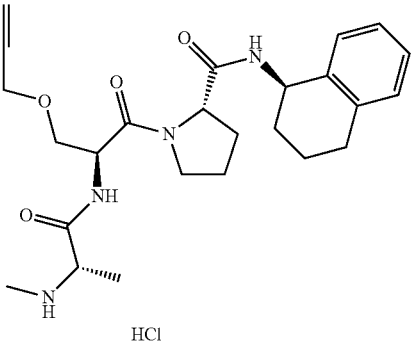 |
| 66 | 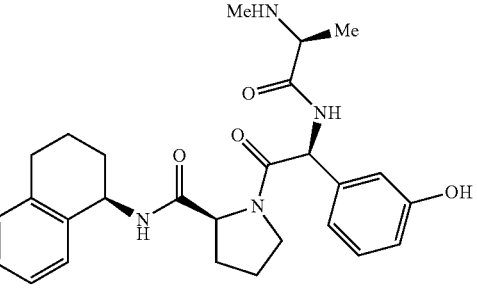 |
| 67 | 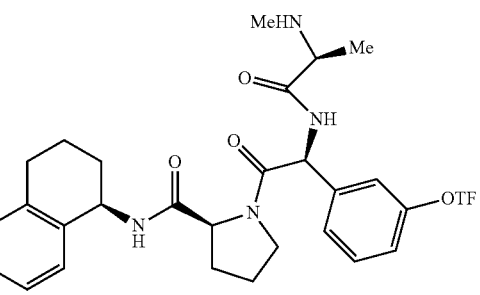 |
| 68 (Example 10) | 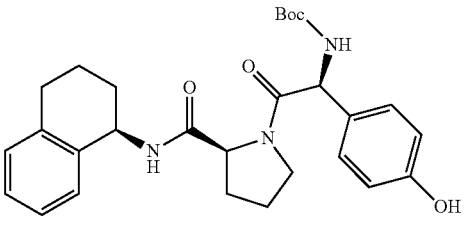 [SMILES: CC(C)(C)OC(=O)N[C@H](C(=O)N1CCC[C@H]1C(=O)N[C@@H]1CCCc2ccccc21)c1ccc(O)cc1] |
| 69 (Example 11) | 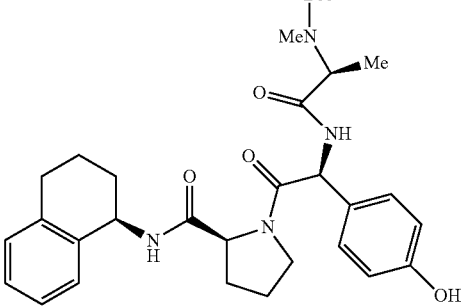 |

TABLE 3-continued
Representative Monomers
| Compound No. | Structure |
|---|---|
| 70 (Example 12) | 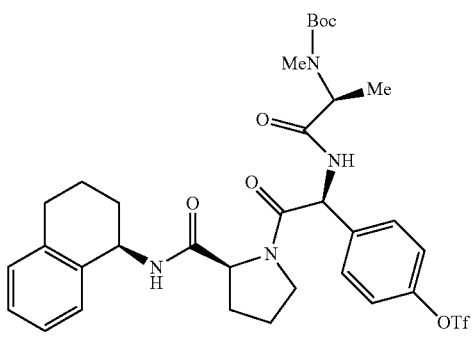 [SMILES: C[C@@H](C(=O)N[C@H](C(=O)N1CCC[C@H]1C(=O)N[C@@H]1CCCc2ccccc21)c1ccc(OS(=O)(=O)C(F)(F)F)cc1)N(C)C(=O)OC(C)(C)C] |
| 71 | 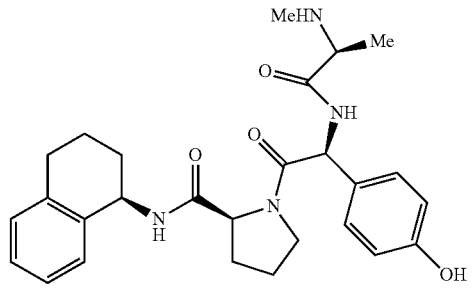 [SMILES: CN[C@@H](C)C(=O)N[C@H](C(=O)N1CCC[C@H]1C(=O)N[C@@H]1CCCc2ccccc21)c1ccc(O)cc1] |
| 72 | 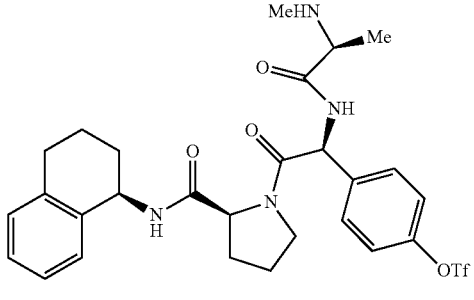 [SMILES: CC[C@H](NC)C(=O)N[C@H](C(=O)N1CCC[C@H]1C(=O)N[C@@H]1CCCc2ccccc21)c1ccc(OS(=O)(=O)C(F)(F)F)cc1] |
| 73 | 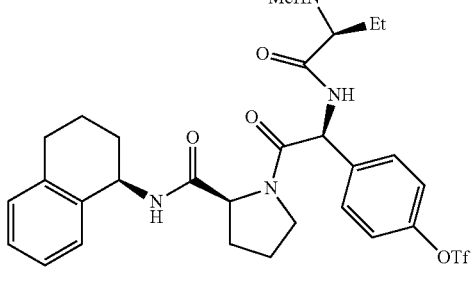 |
| 74 | 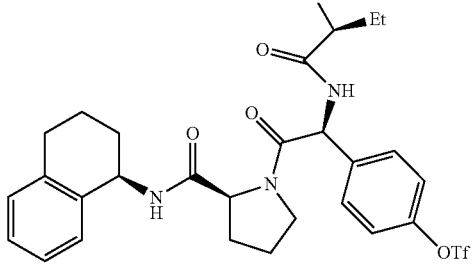 |
| 75 (Example 15) | 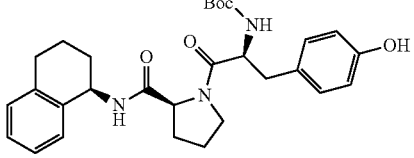 |
| 76 (Example 16) | 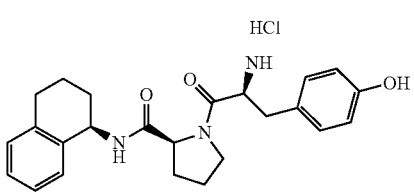 [SMILES: Cl ; N[C@@H](Cc1ccc(O)cc1)C(=O)N1CCC[C@H]1C(=O)N[C@@H]1CCCc2ccccc21] |
| 77 (Example 17) | 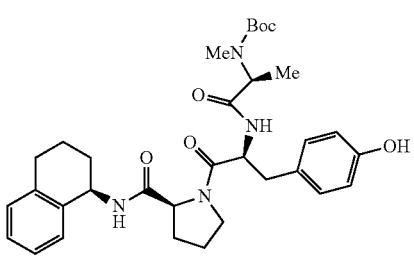 [SMILES: C[C@@H](C(=O)N[C@@H](Cc1ccc(O)cc1)C(=O)N1CCC[C@H]1C(=O)N[C@@H]1CCCc2ccccc21)N(C)C(=O)OC(C)(C)C] |
| 78 | 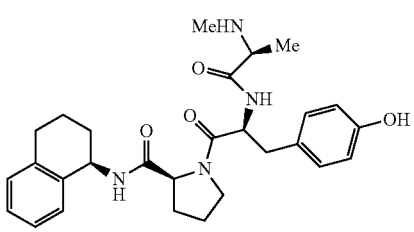 [SMILES: CN[C@@H](C)C(=O)N[C@@H](Cc1ccc(O)cc1)C(=O)N1CCC[C@H]1C(=O)N[C@@H]1CCCc2ccccc21] |
| 79 | 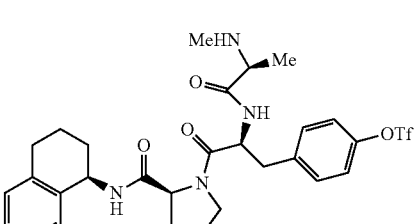 |
| 80 | 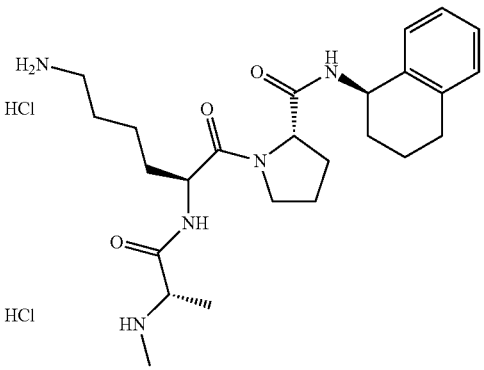 [SMILES: Cl ; Cl ; CN[C@@H](C)C(=O)N[C@@H](CCCCN)C(=O)N1CCC[C@H]1C(=O)N[C@@H]1CCCc2ccccc21] |

TABLE 3-continued

Representative Monomers

| Compound No. | Structure |
|---|---|
| 81 | 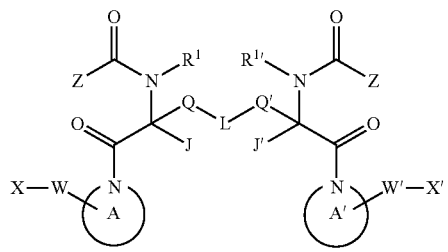 |

All publications and patent applications cited in this specification and all references cited therein are herein incorporated by reference as if each individual publication or patent application or reference were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The invention claimed is:

1. A compound of formula (I):

(I)

[Structure of formula I]

or a pharmaceutically acceptable salt or hydrate form thereof; and including any stereoisomeric forms thereof;
wherein each of ring A and ring A' independently represents a saturated 3-8 membered monocyclic azacyclic ring or a saturated 8-12 membered fused polycyclic azacyclic ring, each of which may contain 0-2 additional heteroatoms selected from N, O, S as ring members; and wherein ring A is substituted with a group represented as —W—X, and ring A' is substituted with a group represented as W'—X', and each of ring A and ring A' may be optionally substituted with from 1-4 additional substituents suitable for its structure;
each J and J' is independently H, CN, C1-C4 alkyl or C1-C4 alkyloxycarbonyl;
each W and W' independently represents C=O, C=S, or an optionally substituted $C_2$-$C_6$ alkylene or $C_2$-$C_6$ heteroalkylene; or W and/or W' can be a bond where X and/or X' comprises an optionally substituted 5-membered or 6-membered aryl or heteroaryl ring;
each X and X' independently represents an optionally substituted C5-C20 ring system comprising at least one aromatic ring and up to four heteroatoms selected from N, O and S, and can represent either a single 5-15 membered cyclic group or two 5-10 membered cyclic groups that are both attached to the same atom of W or W', provided that each X and X' comprises at least one aryl or heteroaryl ring;
each Q and Q' independently represents —$CH_2$—, —CH (OR)—, —CH(R)—, —($CH_2$)$_r$A-, —CH(R)A-, or —CR=CR— or —C≡C—, wherein r is 1-4, each A is independently O, NR, or S, and wherein each R is independently H, $C_1$-$C_8$ alkyl or $C_1$-$C_8$ heteroalkyl; or one or both of Q and Q' can be a bond where L comprises a ring;
each $R^1$ and $R^{1'}$ is independently H or optionally substituted C1-C4 alkyl;
each Z and Z' is independently an optionally substituted C1-C6 aminoalkyl; and
L represents a linker that is a C2-C20 hydrocarbyl group, optionally containing from 1-6 heteroatoms selected from N, O and S, which linker is 2 to 10 atoms in length when counted along the shortest path between Q and Q', and which may be optionally substituted;
with the proviso that L does not comprise a disulfide bond.

2. The compound of claim 1, wherein each of ring A and ring A' is independently selected from the following group:

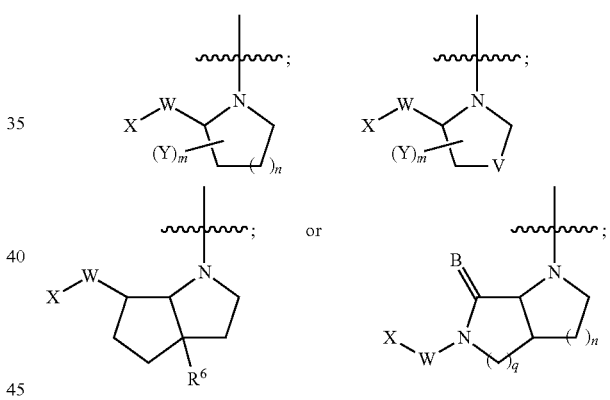

wherein each Y independently represents optionally substituted C1-C8 alkyl, C5-C12 aryl, C5-C20 arylalkyl, or a heteroform of one of these; or is =O, OR, SR, S(O)R, $SO_2R$, $SO_2NR_2$, $NR_2$, OC(O)R, NRC(O)R, NRCOOR, NRC(O)$NR_2$, $NRSO_2R$, CN, C(O)$NR_2$, C(O)R, COOR, $NO_2$ or halo, wherein each R is independently H, $C_1$-$C_8$ alkyl, C5-C12 aryl or C5-C20 arylalkyl, or a heteroform of one of these; or is any other substituent suitable for an alkyl group; and wherein two Y groups on the same ring can cyclize to form a 3-6 membered ring that can be saturated, unsaturated or aromatic, and which ring may include a heteroatom selected from O, S and N as a ring member and may be substituted;
m is 0-4;
n is 0-3;
V is O or S;
$R^6$ is independently H or C1-C4 alkyl;
=B represents =O, =S, $H_2$ or $F_2$; and
q is 1-4.

3. The compound of claim 1, wherein each J and J' is H, and each $R^1$ and $R^{1'}$ is H.

4. The compound of claim 1, wherein each Z and Z' is a 1-aminoalkyl group represented by the formula —CH(R)NR$_2$, where each R is independently H or C1-C4 alkyl.

5. The compound of claim 2, wherein each J and J' is H, and each R$^1$ and R$^{1'}$ is H, and wherein each Z and Z' is a 1-aminoalkyl group represented by the formula —CH(R)NR$_2$, where each R is independently H or C1-C4 alkyl.

6. The compound of claim 1, wherein each X and X' independently comprises a phenyl, pyridyl, pyrimidyl, pyrazinyl, pyridazinyl, or triazinyl ring, each of which may be optionally substituted, or a thienyl, furanyl, pyrrolyl, pyrazolyl, thiazolyl, isothiazolyl, oxazolyl, isoxazolyl, imidazolyl, triazolyl, thiadiazolyl, oxadiazolyl, or tetrazolyl ring, each of which may be optionally substituted.

7. The compound of claim 5, wherein each X and X' independently comprises a phenyl, pyridyl, pyrimidyl, pyrazinyl, pyridazinyl, or triazinyl ring, each of which may be optionally substituted, or a thienyl, furanyl, pyrrolyl, pyrazolyl, thiazolyl, isothiazolyl, oxazolyl, isoxazolyl, imidazolyl, triazolyl, thiadiazolyl, oxadiazolyl, or tetrazolyl ring, each of which may be optionally substituted.

8. The compound of claim 1, wherein:
each W and W' is substituted with a carbonyl oxygen (=O);
each W and W' represents —C(O)NR(CHR)$_p$—, where p is 0, 1 or 2, and each R independently represents H, C1-C4 alkyl or C1-C4 heteroalkyl;
each W and W' comprises a C2-C6 alkylene or C2-C6 heteroalkylene represented by the formula —(CH$_2$)$_p$—, —CH$_2$—O—(CH$_2$)$_p$—, —CH$_2$S(CH$_2$)$_p$—, —CH$_2$S(O)(CH$_2$)$_p$—, —CH$_2$SO$_2$(CH$_2$)$_p$—, —CH$_2$NR(CH$_2$)$_p$—, or —CH$_2$NRSO$_2$(CH$_2$)$_p$— where p is 0, 1, or 2, and each R is independently H, or optionally substituted C1-C8 alkyl or C5-C12 arylalkyl; or
each W and W' represents a bond where each X and X' comprises an optionally substituted 5- or 6-membered aryl or heteroaryl ring.

9. The compound of claim 5, wherein:
each W and W' is substituted with a carbonyl oxygen (=O);
each W and W' represents —C(O)NR(CHR)$_p$—, where p is 0, 1 or 2, and each R independently represents H, C1-C4 alkyl or C1-C4 heteroalkyl;
each W and W' comprises a C2-C6 alkylene or C2-C6 heteroalkylene represented by the formula —(CH$_2$)$_p$—, —CH$_2$—O—(CH$_2$)$_p$—, —CH$_2$S(CH$_2$)$_p$—, —CH$_2$S(O)(CH$_2$)$_p$—, —CH$_2$SO$_2$(CH$_2$)$_p$—, —CH$_2$NR(CH$_2$)$_p$—, or —CH$_2$NRSO$_2$(CH$_2$)$_p$— where p is 0, 1, or 2, and each R is independently H, or optionally substituted C1-C8 alkyl or C5-C12 arylalkyl; or
each W and W' represents a bond where each X and X' comprises an optionally substituted 5- or 6-membered aryl or heteroaryl ring.

10. The compound of claim 1, wherein L comprises:
a symmetric C2-C8 alkynylene;
a 1,4-buta-1,3-diynylene linker represented by the formula —C≡C—C≡C—; or
at least one ring that is part of or is fused to the linker which forms the shortest path between Q and Q' or;
at least one triazole ring.

11. The compound of claim 5, wherein L comprises:
a symmetric C2-C8 alkynylene;
a 1,4-buta-1,3-diynylene linker represented by the formula —C≡C—C≡C—; or
at least one ring that is part of or is fused to the linker which forms the shortest path between Q and Q' or;
at least one triazole ring.

12. The compound of claim 1, wherein each Q and each Q' is selected from a bond where L comprises a ring, and —CH$_2$—, or Q-L-Q' represents —CH(R)—O-L-O—CH(R)—, where each R is independently H or methyl.

13. The compound of claim 5, wherein each Q and each Q' is selected from a bond where L comprises a ring, and —CH$_2$—, or Q-L-Q' represents —CH(R)—O-L-O—CH(R)—, where each R is independently H or methyl.

14. The compound of claim 1, wherein:
Q-L-Q' represents a group selected from:

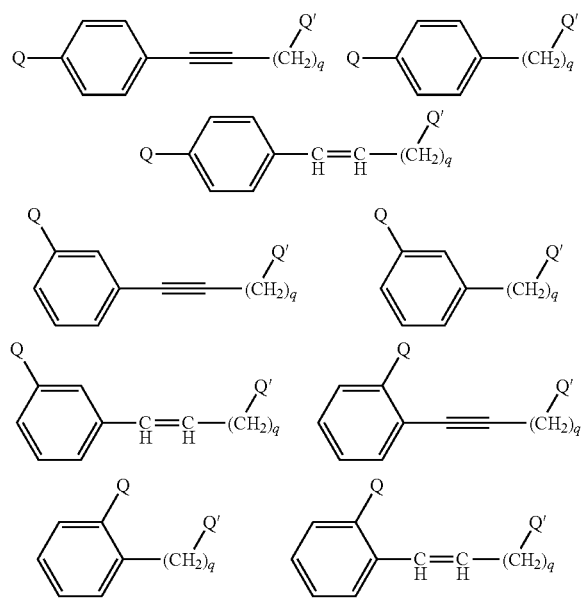

wherein each q is independently 0-4, and each phenyl ring is optionally substituted with 1-2 groups selected from C1-C4 alkyl, C1-C4 alkoxy, CF$_3$, and halo; or Q-L-Q' represents a group selected from:

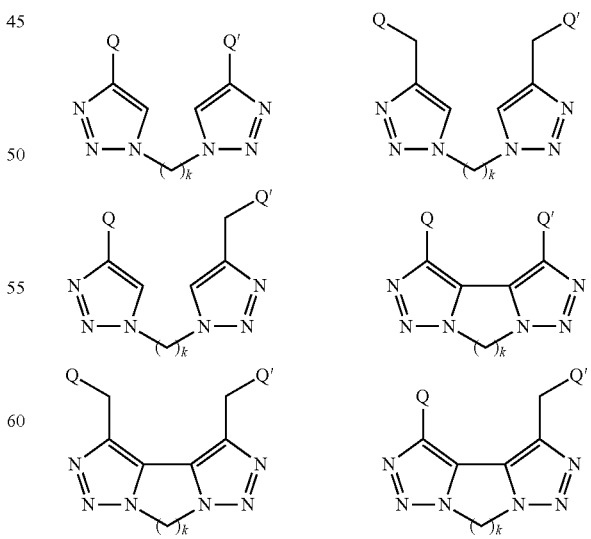

wherein each k is independently 1-4.

15. The compound of claim 5, wherein:

Q-L-Q' represents a group selected from:

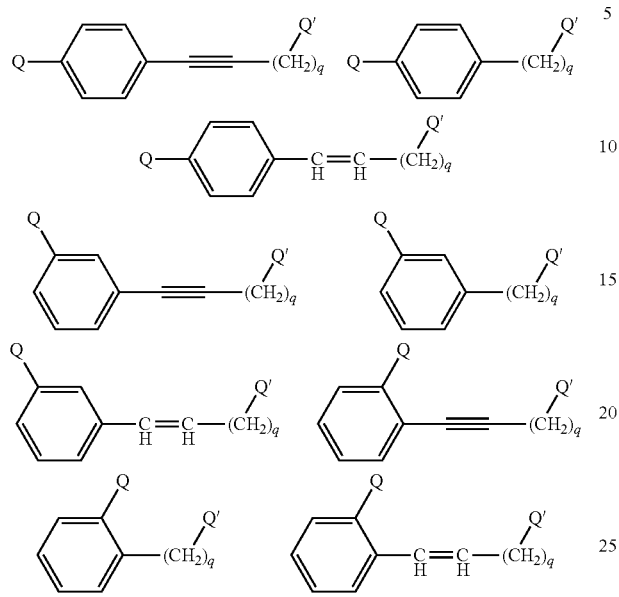

wherein each q is independently 0-4, and each phenyl ring is optionally substituted with 1-2 groups selected from C1-C4 alkyl, C1-C4 alkoxy, $CF_3$, and halo; or Q-L-Q' represents a group selected from:

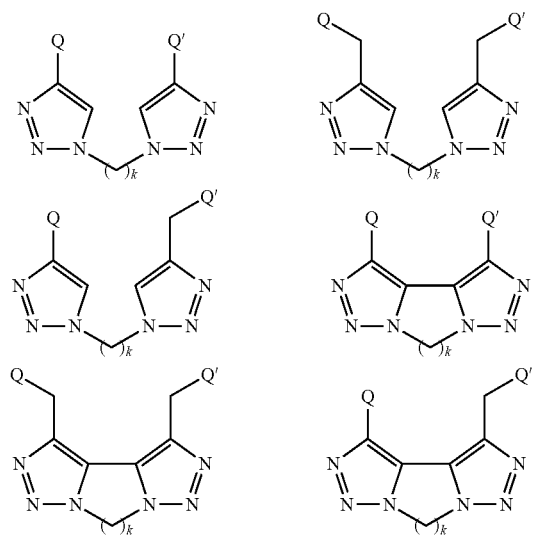

wherein each k is independently 1-4.

16. A compound of formula (II):

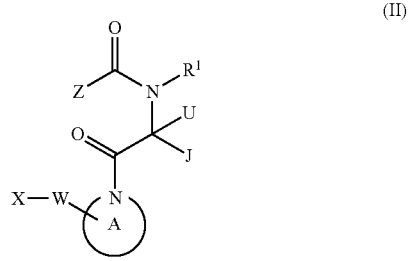

(II)

or a pharmaceutically acceptable salt or hydrate form thereof; and including any stereoisomeric forms thereof; wherein J is H, CN, C1-C4 alkyl or C1-C4 alkyloxycarbonyl;

W represents C=O, C=S, or an optionally substituted $C_2$-$C_6$ alkylene or $C_2$-$C_6$ heteroalkylene; or W can be a bond where X comprises an optionally substituted 5-membered or 6-membered aryl or heteroaryl ring;

X represents an optionally substituted C5-C20 ring system comprising at least one aromatic ring and up to four heteroatoms selected from N, O and S, and can represent either a single 5-15 membered cyclic group or two 5-10 membered cyclic groups that are both attached to the same atom of W, provided that each X comprises at least one aryl or heteroaryl ring;

U represents C1-C8 alkyl, C1-C8 heteroalkyl, C2-C8 alkenyl, C2-C8 heteroalkenyl, C2-C8 alkynyl, C2-C8 heteroalkynyl, C1-C6 aminoalkyl, C5-C12 aryl, C5-C12 heteroaryl, C5-C20 arylalkyl or C5-C20 heteroarylalkyl, each of which may be optionally substituted; with the proviso that U is not isopropyl;

$R^1$ is H or optionally substituted C1-C4 alkyl; and

Z is an optionally substituted C1-C6 aminoalkyl wherein the amine may be in a protected or unprotected form.

17. A dimer comprising two compounds of claim 16 linked through their respective U moieties.

18. A pharmaceutical composition comprising a compound of claim 1 and at least one pharmaceutically acceptable excipient, further comprising at least one additional therapeutic agent, wherein the additional therapeutic agent is selected from the group consisting of TRAIL, etoposide, a TRAIL receptor antibody, an Hsp90 inhibitor, TNF-α, and TNF-β.

19. A method to treat a disease comprising administering to a subject diagnosed with said disease an effective amount of a compound of claim 1, wherein the disease is cancer, inflammation or an autoimmune disorder.

20. A method of making a compound of claim 1 comprising reacting a first monomer of formula (II) with a second monomer of formula (II) wherein for each of said first monomer and said second monomer, U comprises at least one functional group that can be used to connect said first monomer and said second monomer to provide a compound of formula (I), which may be symmetrical or unsymmetrical.

* * * * *